(12) United States Patent
Schubert et al.

(10) Patent No.: US 11,360,106 B2
(45) Date of Patent: *Jun. 14, 2022

(54) CARTRIDGE DEVICE FOR A MEASURING SYSTEM FOR MEASURING VISCOELASTIC CHARACTERISTICS OF A SAMPLE LIQUID, A CORRESPONDING MEASURING SYSTEM, AND A CORRESPONDING METHOD

(71) Applicant: C A Casyso GmbH, Basel (CH)

(72) Inventors: Axel Schubert, Munich (DE); Jose J. Romero-Galeano, Markt Schwaben (DE); Max Kessler, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/372,637

(22) Filed: Jul. 12, 2021

(65) Prior Publication Data
US 2021/0341499 A1 Nov. 4, 2021

Related U.S. Application Data

(63) Continuation of application No. 17/182,502, filed on Feb. 23, 2021, now Pat. No. 11,061,038, which is a
(Continued)

(51) Int. Cl.
*G01N 33/86* (2006.01)
*B01L 3/00* (2006.01)
(Continued)

(52) U.S. Cl.
CPC ............. *G01N 33/86* (2013.01); *B01L 3/502* (2013.01); *B01L 3/52* (2013.01); *G01N 11/00* (2013.01);
(Continued)

(58) Field of Classification Search
CPC .......... G01N 11/00; G01N 33/86; B01L 3/502
See application file for complete search history.

(56) References Cited

U.S. PATENT DOCUMENTS 2,555,937 A 6/1951 Rosenthal
2,995,425 A 8/1961 Hans
(Continued)

FOREIGN PATENT DOCUMENTS

AU 2011237383 B2 10/2012
CN 101195112 6/2006
(Continued)

OTHER PUBLICATIONS

Straub, Andreas, et al. "Using reagent-supported thromboelastometry (ROTEMW) to monitor haemostatic changes in congenital heart surgery employing deep hypothermic circulatory arrest" European Journal of Cardio-thoracic Surgery 34 (2008) 641-647. (Year: 2008).*
(Continued)

*Primary Examiner* — Paul M. West
(74) *Attorney, Agent, or Firm* — Burns & Levinson LLP

(57) ABSTRACT

The present invention is directed to a cartridge device for a measuring system for measuring viscoelastic characteristics of a sample liquid, in particular a blood sample, comprising a cartridge body having at least one measurement cavity formed therein and having at least one probe element arranged in said at least one measurement cavity for performing a test on said sample liquid; and a cover being attachable on said cartridge body; wherein said cover covers at least partially said at least one measurement cavity and forms a retaining element for retaining said probe element in a predetermined position within said at least one measurement cavity. The invention is directed to a measurement system and a method for measuring viscoelastic characteristics of a sample liquid.

29 Claims, 11 Drawing Sheets

Related U.S. Application Data continuation of application No. 16/520,004, filed on Jul. 23, 2019, now Pat. No. 10,996,230, which is a continuation of application No. 16/146,333, filed on Sep. 28, 2018, now Pat. No. 10,746,750, which is a continuation of application No. 15/869,782, filed on Jan. 12, 2018, now abandoned, which is a continuation of application No. 15/357,492, filed on Nov. 21, 2016, now Pat. No. 9,915,671, which is a continuation of application No. 15/066,605, filed on Mar. 10, 2016, now Pat. No. 9,739,789, which is a continuation of application No. 13/895,034, filed on May 15, 2013, now Pat. No. 9,285,377, which is a continuation of application No. 12/640,376, filed on Dec. 17, 2009, now Pat. No. 8,448,499.

(60) Provisional application No. 61/140,344, filed on Dec. 23, 2008.

(51) Int. Cl.
  G01N 11/00 (2006.01)
  G01N 33/49 (2006.01)
  G01N 11/14 (2006.01)

(52) U.S. Cl.
  CPC .......... *G01N 11/14* (2013.01); *G01N 33/4905* (2013.01); *B01L 2200/10* (2013.01); *B01L 2300/0627* (2013.01); *B01L 2300/0636* (2013.01); *B01L 2300/087* (2013.01); *B01L 2300/0861* (2013.01); *B01L 2400/0475* (2013.01); *G01N 2011/0046* (2013.01); *G01N 2333/96458* (2013.01); *G01N 2800/224* (2013.01)

(56) References Cited

U.S. PATENT DOCUMENTS

| | | |
|---|---|---|
| 3,714,815 A | 2/1973 | Hartert |
| 3,803,903 A | 4/1974 | Lin |
| 3,903,903 A | 9/1975 | Matsumura |
| 4,112,740 A | 9/1978 | Brandestini |
| 4,148,216 A | 4/1979 | Do et al. |
| 4,193,293 A | 3/1980 | Cavallari |
| D260,428 S | 8/1981 | Fekete |
| 4,319,194 A | 3/1982 | Cardinal |
| 4,443,408 A | 4/1984 | Mintz |
| 4,558,589 A | 12/1985 | Hemmes et al. |
| 4,599,219 A | 7/1986 | Cooper |
| 4,671,939 A | 6/1987 | Mintz |
| 4,695,956 A | 9/1987 | Leveen et al. |
| 4,705,756 A | 11/1987 | Spillert et al. |
| 4,726,220 A | 2/1988 | Feier et al. |
| 4,753,776 A | 6/1988 | Hillman et al. |
| 4,756,884 A | 7/1988 | Hillman et al. |
| 4,765,180 A | 8/1988 | Clifton |
| 4,767,600 A | 8/1988 | Vicario |
| 4,814,247 A | 3/1989 | Spillert et al. |
| D302,294 S | 7/1989 | Hillman |
| 4,849,340 A | 7/1989 | Oberhardt |
| 4,852,577 A | 8/1989 | Smith et al. |
| 4,868,129 A | 9/1989 | Gibbons et al. |
| D305,360 S | 1/1990 | Fechtner |
| 4,900,679 A | 2/1990 | Spillert et al. |
| 4,948,961 A | 8/1990 | Hillman et al. |
| 4,956,089 A | 9/1990 | Hurst |
| 4,963,498 A | 10/1990 | Hillman et al. |
| 5,009,316 A | 4/1991 | Klein |
| 5,016,469 A | 5/1991 | Henderson |
| 5,028,142 A | 7/1991 | Ostolch et al. |
| 5,056,357 A | 10/1991 | Dymling et al. |
| 5,077,017 A | 12/1991 | Gorin et al. |
| 5,091,304 A | 2/1992 | La Duca et al. |
| 5,104,813 A | 4/1992 | Besemer et al. |
| 5,104,975 A | 4/1992 | McCormick et al. |
| D327,743 S | 7/1992 | Frenkel |
| 5,164,598 A | 11/1992 | Hillman et al. |
| 5,169,786 A | 12/1992 | Caroll et al. |
| 5,204,525 A | 4/1993 | Hillman et al. |
| 5,205,159 A | 4/1993 | Carr, Jr. |
| 5,207,988 A | 5/1993 | Lucas |
| 5,222,808 A | 6/1993 | Sugarman et al. |
| 5,223,219 A | 6/1993 | Subramanian et al. |
| 5,223,227 A | 6/1993 | Zuckerman |
| 5,234,839 A | 8/1993 | McCormick et al. |
| 5,273,517 A | 12/1993 | Barone et al. |
| 5,287,732 A | 2/1994 | Sekiguchi |
| 5,300,779 A | 4/1994 | Hillman et al. |
| 5,302,348 A | 4/1994 | Cusack et al. |
| D347,067 S | 5/1994 | Schartle et al. |
| 5,311,908 A | 5/1994 | Barone et al. |
| 5,331,964 A | 7/1994 | Trahey et al. |
| 5,372,946 A | 12/1994 | Cusak et al. |
| 5,378,431 A | 1/1995 | Vogler et al. |
| 5,447,440 A | 9/1995 | Davis et al. |
| 5,473,536 A | 12/1995 | Wimmer |
| 5,487,387 A | 1/1996 | Trahey et al. |
| RE35,171 E | 3/1996 | McCormick et al. |
| 5,504,011 A | 4/1996 | Gavin et al. |
| 5,531,102 A | 7/1996 | Brookfield et al. |
| 5,534,226 A | 7/1996 | Gavin et al. |
| 5,591,403 A | 1/1997 | Gavin et al. |
| 5,602,037 A | 2/1997 | Ostgaard et al. |
| 5,605,154 A | 2/1997 | Ries et al. |
| 5,606,971 A | 3/1997 | Sarvazyan et al. |
| 5,628,961 A | 5/1997 | Davis et al. |
| 5,629,209 A | 5/1997 | Braun, Sr. et al. |
| 5,655,535 A | 8/1997 | Friemel et al. |
| 5,657,760 A | 8/1997 | Ying et al. |
| 5,660,993 A | 8/1997 | Cathey et al. |
| 5,673,699 A | 10/1997 | Trahey et al. |
| 5,731,212 A | 3/1998 | Gavin et al. |
| 5,744,898 A | 4/1998 | Smith et al. |
| 5,763,199 A | 6/1998 | Coller |
| 5,777,212 A | 7/1998 | Sekiguchi et al. |
| 5,777,215 A | 7/1998 | Calatzis et al. |
| 5,788,928 A | 8/1998 | Carey |
| 5,800,781 A | 9/1998 | Gavin et al. |
| 5,810,731 A | 9/1998 | Sarvazyan et al. |
| 5,854,005 A | 12/1998 | Coller |
| 5,854,076 A | 12/1998 | Kundu et al. |
| 5,854,423 A | 12/1998 | Venegas |
| 5,888,826 A | 3/1999 | Ostgaard et al. |
| 5,899,861 A | 5/1999 | Friemel et al. |
| 5,902,037 A | 5/1999 | Amrani et al. |
| 5,902,937 A | 5/1999 | Amrani et al. |
| 5,921,928 A | 7/1999 | Greenleaf et al. |
| 5,922,551 A | 7/1999 | Durbin et al. |
| 5,922,591 A | 7/1999 | Anderson et al. |
| 5,952,560 A | 9/1999 | Collings et al. |
| 6,012,712 A | 1/2000 | Bernstein |
| 6,016,712 A | 1/2000 | Warden et al. |
| 6,033,546 A | 3/2000 | Ramsey |
| 6,039,691 A | 3/2000 | Walker et al. |
| 6,046,051 A | 4/2000 | Jina |
| 6,066,243 A | 5/2000 | Anderson et al. |
| 6,083,159 A | 7/2000 | Driscoll, Jr. et al. |
| 6,114,135 A | 9/2000 | Goldstein |
| 6,117,081 A | 9/2000 | Jago et al. |
| 6,135,957 A | 10/2000 | Cohen-bacrie et al. |
| 6,197,595 B1 | 3/2001 | Anderson et al. |
| 6,200,532 B1 | 3/2001 | Wu et al. |
| 6,213,950 B1 | 4/2001 | Cespedes et al. |
| 6,221,672 B1 | 4/2001 | Baugh et al. |
| RE37,171 E | 5/2001 | Busche et al. |
| 6,225,126 B1 | 5/2001 | Cohen et al. |
| 6,232,127 B1 | 5/2001 | Lans et al. |
| 6,242,267 B1 | 6/2001 | Herron et al. |
| 6,264,609 B1 | 7/2001 | Herrington et al. |
| 6,270,459 B1 | 8/2001 | Konofagou et al. |
| 6,277,074 B1 | 8/2001 | Chaturvedi et al. |
| 6,283,917 B1 | 9/2001 | Jago et al. |

(56) References Cited

U.S. PATENT DOCUMENTS

| | | |
|---|---|---|
| 6,318,191 B1 | 11/2001 | Chen |
| 6,371,912 B1 | 4/2002 | Nightinggale et al. |
| 6,402,704 B1 | 6/2002 | McMorrow |
| 6,403,381 B1 | 6/2002 | Mann et al. |
| 6,412,344 B1 | 7/2002 | Danicich et al. |
| 6,413,782 B1 | 7/2002 | Parce et al. |
| 6,429,025 B1 | 8/2002 | Parce et al. |
| 6,436,722 B1 | 8/2002 | Clark et al. |
| 6,448,024 B1 | 9/2002 | Bruegger |
| 6,451,610 B1 | 9/2002 | Gorman et al. |
| 6,454,714 B1 | 9/2002 | Ng et al. |
| 6,479,299 B1 | 11/2002 | Parce et al. |
| 6,494,834 B2 | 12/2002 | Konofagou et al. |
| 6,508,768 B1 | 1/2003 | Hall et al. |
| 6,514,204 B2 | 2/2003 | Alam et al. |
| 6,535,835 B1 | 3/2003 | Rubin et al. |
| 6,537,819 B2 | 3/2003 | Cohen |
| 6,555,381 B2 | 4/2003 | Baugh et al. |
| 6,573,104 B2 | 6/2003 | Carr, Jr. et al. |
| 6,613,286 B2 | 9/2003 | Braun, Sr. et al. |
| 6,613,573 B1 | 9/2003 | Cohen |
| D481,133 S | 10/2003 | Blouin |
| 6,632,678 B2 | 10/2003 | Aiken et al. |
| D482,454 S | 11/2003 | Gebrian |
| 6,662,031 B1 | 12/2003 | Khalil et al. |
| 6,670,133 B2 | 12/2003 | Knapp et al. |
| 6,685,646 B2 | 2/2004 | Cespedes et al. |
| 6,687,625 B2 | 2/2004 | Srinivasan et al. |
| 6,692,439 B1 | 2/2004 | Walker et al. |
| 6,699,718 B1 | 3/2004 | Bruegger |
| 6,716,168 B2 | 4/2004 | Nock et al. |
| 6,726,629 B1 | 4/2004 | Frinking et al. |
| 6,750,053 B1 | 6/2004 | Opalsky |
| 6,764,448 B2 | 7/2004 | Nightingale et al. |
| 6,787,363 B2 | 9/2004 | Cohen et al. |
| 6,797,519 B2 | 9/2004 | Cohen et al. |
| 6,830,936 B2 | 12/2004 | Anderson et al. |
| 6,838,055 B2 | 1/2005 | Sando et al. |
| 6,942,836 B2 | 4/2005 | Freudenthal |
| 6,890,299 B2 | 5/2005 | Cohen et al. |
| 6,951,127 B1 | 10/2005 | Bi |
| 6,951,544 B2 | 10/2005 | Trahey et al. |
| 7,005,857 B2 | 2/2006 | Stiene et al. |
| 7,132,078 B2 | 11/2006 | Rawson et al. |
| 7,179,652 B2 | 2/2007 | Cohen et al. |
| 7,192,726 B1 | 3/2007 | Carr, Jr. et al. |
| 7,202,048 B2 | 4/2007 | Carr, Jr. |
| 7,205,115 B2 | 4/2007 | McHugh et al. |
| 7,207,939 B2 | 4/2007 | Husher |
| 7,247,488 B2 | 7/2007 | Ghai et al. |
| 7,261,861 B2 | 8/2007 | Kautzky |
| 7,285,411 B1 | 10/2007 | Parce et al. |
| 7,374,538 B2 | 5/2008 | Nightingale et al. |
| 7,399,637 B2 | 7/2008 | Wright et al. |
| 7,412,877 B1 | 8/2008 | Bi |
| 7,419,638 B2 | 9/2008 | Saltsman et al. |
| 7,422,905 B2 | 9/2008 | Clague |
| 7,439,069 B2 | 10/2008 | Nippoldt et al. |
| 7,491,175 B2 | 2/2009 | Ruether et al. |
| 7,497,997 B2 | 3/2009 | Glezer et al. |
| 7,524,670 B2 | 4/2009 | Cohen et al. |
| 7,595,169 B2 | 9/2009 | Swaim et al. |
| 7,674,616 B2 | 3/2010 | Farnam, III et al. |
| 7,732,213 B2 | 6/2010 | Cohen et al. |
| 7,745,223 B2 | 6/2010 | Schubert et al. |
| 7,790,362 B2 | 9/2010 | Coller et al. |
| 7,811,792 B2 | 10/2010 | Cohen |
| 7,842,234 B2 | 11/2010 | Lauks et al. |
| 7,892,188 B2 | 2/2011 | Walker et al. |
| 7,897,114 B2 | 3/2011 | Poissy et al. |
| 7,912,661 B2 | 3/2011 | Zeng et al. |
| 7,938,573 B2 | 5/2011 | Gau et al. |
| 7,947,505 B2 | 5/2011 | Kawasaki et al. |
| 7,959,875 B2 | 6/2011 | Zhou et al. |
| 7,972,271 B2 | 7/2011 | Johnson et al. |
| 7,976,795 B2 | 7/2011 | Zhou et al. |
| D645,973 S | 9/2011 | Hoeners |
| 8,017,382 B2 | 9/2011 | Davis et al. |
| 8,058,023 B2 | 11/2011 | Gurbel |
| 8,062,883 B2 | 11/2011 | Woudenberg et al. |
| 8,067,226 B2 | 11/2011 | Woudenberg et al. |
| 8,084,272 B2 | 12/2011 | Campbell et al. |
| 8,110,392 B2 | 2/2012 | Battrell et al. |
| 8,168,442 B2 | 5/2012 | Petersen |
| 8,202,492 B2 | 6/2012 | Linder et al. |
| 8,216,526 B2 | 7/2012 | Locascio et al. |
| 8,222,024 B2 | 7/2012 | Davis et al. |
| 8,283,182 B2 | 10/2012 | Bond et al. |
| 8,318,109 B2 | 11/2012 | Saltsman et al. |
| 8,372,343 B2 | 2/2013 | Goldstein |
| 8,377,392 B2 | 2/2013 | Miller et al. |
| 8,383,045 B2 | 2/2013 | Schubert et al. |
| 8,409,527 B2 | 4/2013 | Linder et al. |
| 8,431,413 B2 | 4/2013 | Dority et al. |
| 8,448,499 B2 | 5/2013 | Schubert et al. |
| 8,475,737 B2 | 7/2013 | Linder et al. |
| 8,548,759 B2 | 10/2013 | Walker et al. |
| 8,574,828 B2 | 11/2013 | Coller et al. |
| 8,591,448 B2 | 11/2013 | Powers et al. |
| 8,591,829 B2 | 11/2013 | Taylor et al. |
| 8,697,009 B2 | 4/2014 | Saltsman et al. |
| 8,709,787 B2 | 4/2014 | Handique |
| 8,740,818 B2 | 6/2014 | Walker et al. |
| 8,765,062 B2 | 7/2014 | Linder et al. |
| 8,802,445 B2 | 8/2014 | Linder et al. |
| 8,857,244 B2 | 10/2014 | Schubert et al. |
| 8,883,510 B2 | 11/2014 | Gehring et al. |
| 8,932,523 B2 | 1/2015 | Linder et al. |
| 9,062,342 B2 | 6/2015 | Carrera Fabra et al. |
| 9,063,121 B2 | 6/2015 | Bru Gilbert et al. |
| 9,068,966 B2 | 6/2015 | Delmenico et al. |
| 9,075,047 B2 | 7/2015 | Linder et al. |
| 9,086,423 B2 | 7/2015 | Schubert et al. |
| 9,110,084 B2 | 8/2015 | Schubert et al. |
| D737,993 S | 9/2015 | Tan |
| 9,238,223 B2 | 1/2016 | Handique |
| 9,272,280 B2 | 3/2016 | Viola et al. |
| 9,285,377 B2 | 3/2016 | Schubert et al. |
| 9,341,637 B2 | 5/2016 | Coller et al. |
| 9,354,243 B2 | 5/2016 | Chapman et al. |
| 9,410,971 B2 | 8/2016 | Viola et al. |
| 9,506,938 B2 | 11/2016 | Coller et al. |
| D777,343 S | 1/2017 | Gorin et al. |
| 9,739,789 B2 | 8/2017 | Schubert et al. |
| 9,915,671 B2 | 3/2018 | Schubert et al. |
| 9,977,039 B2 | 5/2018 | Viola et al. |
| 10,031,144 B2 | 7/2018 | Viola et al. |
| 10,175,225 B2 | 1/2019 | McCluske et al. |
| 10,481,168 B2 | 11/2019 | Viola et al. |
| 10,746,750 B2 | 8/2020 | Schubert et al. |
| 2001/0046685 A1 | 11/2001 | Moskowitz et al. |
| 2002/0013530 A1 | 1/2002 | Cespedes et al. |
| 2002/0040187 A1 | 4/2002 | Alam et al. |
| 2002/0081741 A1 | 6/2002 | Braun, Sr. |
| 2003/0013958 A1 | 1/2003 | Govari et al. |
| 2003/0073244 A1 | 4/2003 | Cohen et al. |
| 2003/0105398 A1 | 6/2003 | Vitek |
| 2003/0113929 A1 | 6/2003 | Baugh et al. |
| 2003/0170883 A1 | 9/2003 | Martin et al. |
| 2003/0171676 A1 | 9/2003 | Trahey et al. |
| 2003/0199082 A1 | 10/2003 | Miller et al. |
| 2003/0204141 A1 | 10/2003 | Nock et al. |
| 2004/0053351 A1 | 3/2004 | Fischer et al. |
| 2004/0065143 A1 | 4/2004 | Husher |
| 2004/0068184 A1 | 4/2004 | Trahey et al. |
| 2004/0072357 A1 | 4/2004 | Stiene et al. |
| 2004/0076546 A1 | 4/2004 | Bissett |
| 2004/0088317 A1 | 5/2004 | Fabrick et al. |
| 2004/0131500 A1 | 7/2004 | Chow |
| 2004/0167403 A1 | 8/2004 | Nightingale et al. |
| 2004/0189311 A1* | 9/2004 | Glezer ............ B01L 3/502715 324/444 |
| 2004/0203163 A1 | 10/2004 | Cohen et al. |
| 2004/0214337 A1 | 10/2004 | Kautzky |

(56) References Cited

U.S. PATENT DOCUMENTS

| | | |
|---|---|---|
| 2005/0004463 A1 | 1/2005 | Chen et al. |
| 2005/0015001 A1 | 1/2005 | Lec et al. |
| 2005/0053305 A1 | 3/2005 | Li et al. |
| 2005/0123447 A1 | 6/2005 | Koike et al. |
| 2005/0148899 A1 | 7/2005 | Walker et al. |
| 2005/0164373 A1 | 7/2005 | Oldham et al. |
| 2005/0215901 A1 | 9/2005 | Anderson et al. |
| 2005/0216987 P1 | 9/2005 | Murakami |
| 2005/0220668 A1 | 10/2005 | Coville |
| 2005/0233460 A1 | 10/2005 | Clague et al. |
| 2005/0233466 A1 | 10/2005 | Wright |
| 2005/0233480 A1 | 10/2005 | Clague et al. |
| 2007/0038095 A1 | 2/2007 | Greenleaf et al. |
| 2007/0059840 A1 | 3/2007 | Cohen et al. |
| 2007/0078631 A1 | 4/2007 | Ariyoshi et al. |
| 2007/0105236 A1 | 5/2007 | Chang et al. |
| 2007/0184508 A1 | 8/2007 | Cohen et al. |
| 2007/0243632 A1 | 10/2007 | Coller et al. |
| 2007/0259348 A1 | 11/2007 | Phadke et al. |
| 2007/0266778 A1 | 11/2007 | Corey et al. |
| 2007/0276236 A1 | 11/2007 | Jong |
| 2008/0026476 A1 | 1/2008 | Howell |
| 2008/0038828 A1 | 2/2008 | Cohen et al. |
| 2008/0160500 A1 | 7/2008 | Fuller |
| 2008/0194967 A1 | 8/2008 | Sliwa et al. |
| 2008/0200343 A1 | 8/2008 | Clemens |
| 2008/0227217 A1 | 9/2008 | Yamamoto et al. |
| 2008/0249408 A1 | 10/2008 | Palmeri et al. |
| 2008/0251383 A1 | 10/2008 | Sobek |
| 2008/0261238 A1 | 10/2008 | Wrabetz et al. |
| 2008/0261261 A1 | 10/2008 | Grimes et al. |
| 2008/0280285 A1 | 11/2008 | Chen et al. |
| 2008/0297169 A1 | 12/2008 | Greenquist |
| 2008/0299587 A1 | 12/2008 | Durbin |
| 2009/0112483 A1 | 4/2009 | Cohen |
| 2009/0130645 A1 | 5/2009 | Schubert et al. |
| 2009/0269837 A1 | 10/2009 | Shevkoplyas et al. |
| 2009/0305315 A1 | 12/2009 | Gandola et al. |
| 2010/0154520 A1 | 6/2010 | Schubert et al. |
| 2010/0184201 A1 | 7/2010 | Schubert et al. |
| 2010/0190193 A1 | 7/2010 | Calatzis et al. |
| 2010/0274130 A1 | 10/2010 | Anand et al. |
| 2011/0034805 A1 | 2/2011 | Walker et al. |
| 2011/0151491 A1 | 6/2011 | Dennis et al. |
| 2011/0172661 A1 | 7/2011 | Designer et al. |
| 2011/0237913 A1 | 9/2011 | Schubert et al. |
| 2011/0252352 A1 | 10/2011 | Viola et al. |
| 2012/0232803 A1 | 9/2012 | Viola et al. |
| 2012/0244392 A1 | 9/2012 | Kleiman |
| 2012/0252127 A1 | 10/2012 | Gregor et al. |
| 2012/0294767 A1 | 11/2012 | Viola et al. |
| 2012/0329082 A1 | 12/2012 | Viola et al. |
| 2013/0190584 A1 | 7/2013 | Walker et al. |
| 2013/0323846 A1 | 12/2013 | Schubert et al. |
| 2013/0323847 A1 | 12/2013 | Schubert et al. |
| 2013/0323848 A1 | 12/2013 | Schubert |
| 2013/0333448 A1 | 12/2013 | Schubert et al. |
| 2014/0004613 A1 | 1/2014 | Goldstein |
| 2014/0234859 A1 | 8/2014 | Coller et al. |
| 2014/0271409 A1 | 9/2014 | Knight |
| 2016/0032355 A1 | 2/2016 | Zaman et al. |
| 2016/0091415 A1 | 3/2016 | Gorin |
| 2016/0091483 A1 | 3/2016 | McCluskey |
| 2016/0091514 A1 | 3/2016 | Gorin et al. |
| 2016/0091515 A1 | 3/2016 | Gorin et al. |
| 2016/0091516 A1 | 3/2016 | Gorin |
| 2016/0091517 A1 | 3/2016 | Gorin |
| 2016/0139159 A1 | 5/2016 | Viola et al. |
| 2016/0195557 A1 | 7/2016 | Schubert et al. |
| 2016/0377638 A1 | 12/2016 | Bels et al. |
| 2017/0097367 A1 | 4/2017 | Schubert et al. |
| 2018/0306774 A1 | 10/2018 | Viola et al. |

FOREIGN PATENT DOCUMENTS

| | | |
|---|---|---|
| CN | 1816306 A | 8/2006 |
| CN | 101195112 | 10/2006 |
| CN | 101035479 A | 9/2007 |
| CN | 1853104 | 10/2016 |
| CN | 103649751 B | 3/2017 |
| DE | 2740932 | 11/1976 |
| DE | 10135569 | 2/2003 |
| DE | 202014002289 | 9/2014 |
| EP | 0404456 | 12/1990 |
| EP | 1162457 | 12/2001 |
| EP | 1347058 A2 | 9/2003 |
| EP | 1367392 B1 | 12/2003 |
| EP | 1394546 | 3/2004 |
| EP | 1627725 | 2/2006 |
| EP | 1827725 | 2/2006 |
| EP | 1684778 | 2/2008 |
| EP | 1901065 | 3/2008 |
| EP | 2208996 | 9/2010 |
| EP | 2202517 | 8/2012 |
| EP | 2555704 B1 | 2/2013 |
| EP | 2676143 A2 | 12/2013 |
| GB | 2257256 | 1/1993 |
| JP | 1971004947 | 11/1971 |
| JP | S55050162 A | 3/1982 |
| JP | H01140047 A | 6/1987 |
| JP | 03031764 | 2/1991 |
| JP | H09504372 A | 4/1997 |
| JP | 2009-159596 | 6/1997 |
| JP | 09159596 | 6/1997 |
| JP | 09507580 | 7/1997 |
| JP | 2001-516880 A | 10/2001 |
| JP | 2006-053142 | 2/2006 |
| JP | 2010-266453 A | 11/2010 |
| JP | 2011-174952 A | 9/2011 |
| JP | 2012-513582 A | 6/2012 |
| JP | 2012515340 | 7/2012 |
| JP | 2015045642 | 3/2015 |
| WO | 1989/006803 | 7/1989 |
| WO | 1997/041432 | 11/1997 |
| WO | 2002/050535 | 6/2002 |
| WO | 2002/063273 | 8/2002 |
| WO | 2005/106467 | 11/2005 |
| WO | 2006/091650 | 8/2006 |
| WO | 2006/126290 | 11/2006 |
| WO | 2007/047961 | 4/2007 |
| WO | 2008/075181 | 6/2008 |
| WO | 2008/093216 | 7/2008 |
| WO | 2009152094 A2 | 12/2009 |
| WO | 2010/072620 | 7/2010 |
| WO | 2011035162 A1 | 3/2011 |
| WO | 2011/117017 | 9/2011 |
| WO | 2011127436 A2 | 10/2011 |
| WO | 2012159021 A2 | 11/2012 |
| WO | 2013105987 A2 | 7/2013 |
| WO | 2014/103744 | 7/2014 |
| WO | 2014/115478 | 7/2014 |

OTHER PUBLICATIONS

Malinin, et al., "Validation of a VerifyNow-P2Y12 cartridge for monitoring platelet inhibition with clopidogrel," Methods and Findings in Experimental and Clinical Pharmacology, vol. 28, No. 5, Jun. 2006, pp. 315-322.

European Search Report in corresponding application No. 20175351.4 dated Sep. 21, 2020.

Petitioner's Power of Attorney filed on Apr. 24, 2019 for PGR2019-00047.

Petition for Post-Grant Review of U.S. Pat. No. 10,031,144 filed on Apr. 24, 2019 for PGR2019-00047.

Declaration of Frank LaDuca PH.D, FAHA filed on Apr. 24, 2019. Exhibit 1002 to PGR2019-00047.

Certificate of Correction for U.S. Pat. No. 10,031,144 filed on Apr. 24, 2019. Exhibit 1003 to PGR2019-00047.

Provisional Application for Patent Cover Sheet filed on Apr. 24, 2019. Exhibit 1004 to PGR2019-00047.

(56) References Cited

OTHER PUBLICATIONS

U.S. Patent Publication No. 2014/0154520 Schubert et al. Jun. 24, 2010. Exhibit 1005 to PGR2019-00047.
Ganter, M. et al. Coagulation Monitoring: Current Techniques and Clinical Use of Viscoelastic Point-of-Care Coagulation Devices, 2008. Exhibit 1007 to PGR2019-00047.
Hanecke, P. et al. Thrombelastography Today: Practicability and Analytical Power. Transfusion Medicine and Hemotherapy, 2007 ; 34:421-428. Exhibit 1008 to PGR2019-00047.
510(k) Summary, Pentapharm GmbH ROTEM Delta Thrombelastography System filed on Apr. 24, 2019. Exhibit 1009 to PGR2019-00047.
510(k) Substantial Equivalence Determination Decision Summary filed on Apr. 24, 2019 Exhibit 1010 to PGR2019-00047.
User Manual TEG 5000 Thrombelastograph Hemostasis System filed on Apr. 24, 2019. Exhibit 1011 to PCR2019-00047.
U.S. Pat. No. 6,537,819, Cohen el al. Mar. 25, 2003. Exhibit 1012 to PGR2019-00047.
Viola, F. et al. A novel ultraound-based method to evaluate hemostatic function of whole blood. Clinica Chimica Acta 411, 2010: 106-113. Exhibit 1013 to PGR2019-00047.
Park IP Translations filed Apr. 24, 2019. Exhibit 1016 to PGR2019-00047.
Nielsen, V. A Comparison of of the Thrombelastograph and the ROTEM, 2007. Exhibit 1017 to PGR2019-00047.
Viola, F. et al. Sonorheometry: A Noncontact Method for the Dynamic Assessment of Thrombosis. Annals of Biomedical Engineering, vol. 32 May 5, 2004. pp. 696-705. Exhibit 1019 to PGR2019-00047.
Viola, F. et al. Sonorheometry: A New Method for Assessing Coagulation Potential, 2007. Exhibit 1020 to PGR2019-00047.
Lang, T. et al. Multi-centre investigation on reference ranges for ROTEM thromboelastometry, 2005. Exhibit 1026 to PGR2019-00047.
Rugeri, L. et al. Diagnosis of early coagulation abnormalities in trauma patients by rotation thromboelastometry. 5(2):289-295. 2007. Exhibit 1027 to PGR2019-00047.
Final Written Decision filed on Apr. 24, 2019. Exhibit 1028 to PGR2019-00047.
Final Written Decision filed on Apr. 24, 2019. Exhibit 1029 to PGR2019-00047.
Notice of Filing Date Accorded to Petition and Time for Filing Patent Owner Preliminary Response filed on Apr. 29, 2019 for PGR2019-00047.
Patent Owner's Power of Attorney filed on May 8, 2019 for PGR2019-00047.
Patent Owner's Mandatory Notices filed on May 8, 2019 for PGR2019-00047.
Patent Owner's Preliminary Response to Petition for Post-Grant Review of U.S. Pat. No. 10,031,144 filed on Jul. 29, 2019 for PGR2019-00047.
Declaration of James P. Landers in Support of Patent Owner's Preliminary Response to Petition for Post-Grant Review of U.S. Pat. No. 10,031,144 filed on Jul. 29, 2019. Exhibit 2001 to PGR2019-00047.
James P. Landers Curriculum Vita filed on Jul. 29, 2019. Exhibit 2002 to PGR2019-00047.
Pertinent Materials Reviewed and Considered by James P. Landers, Ph.D filed on Jul. 29, 2019. Exhibit 2003 to PGR2019-00047.
Colman, R. et al. Hemostasis and Thrombosis, 1994. Exhibit 2004 to PGR-00047.
Wolberg, A.S. Plasma and cellular contributions to fibrin network formation, structure and stability. Department of Pathology and Laboratory Medicine, University of North Carolina at Chapel Hill, NC. Haemophilia 2010. Exhibit 2005 to PGR2019-00047.
Kuntamukkula, M.S. et al. Rheological Studies of the Contractile Force Within Platlet-Fibrin Clots: Effects of Prostaglandin E1, Dibutyryl-cAMP and Dibutyryl-cGMP, 1978. Exhibit 2006 to PGR2019-00047.
Harrison, P. Assessment of Platelet Function in the Laboratory, 2009. Exhibit 2007 to PGR2019-00047.
Harris, N. et al. Coagulation Tests: A Primer on Hemostasis for Clinical Chemists, 2012. Exhibit 2008 to PGR2019-00047.
Plotkin, A. et al. A Reduction in Clot Formation Rate and Strength Assessed by Thrombelastography is Indicative of Transfusion Requirements in Patients with Penetrating Injuries. The Journal of Trauma Injury, Infection, and Critical Care. 2008. Exhibit 2009 to PGR2019-00047.
Evans, P.A. et al. Rheometry and associated techniques for blood cogaulation studies. Medical Engineering & Physics 30 (2008) 671-679. Exhibit 2010 to PGR2019-00047.
Van den Berg, A. et al. Micro Total Analysis Systems: Microfluidic Aspects, Integration Concept and Applications, 1998. Exhibit 2011 to PGR2019-00047.
Devices, Systems and Methods for Evaluation of Hemostasis filed on Jul. 29, 2019. Exhibit 2012 to PGR2019-00047.
Crochemore, T. et al. A new era of thromboelastrometry, 2017. Exhibit 2013 to PGR2019-00047.
Berney, H. et al. Impedance Measurement Monitors Blood Coagulation, 2008. Exhibit 2014 to PGR2019-00047.
Puckett, L. et al. Monitoring blood coagulation with magnetoelastic sersors. Biosensors and Bioelectornics 18 (2003) 675-681. Exhibit 2015 to PGR2019-00047.
Lo, R. et al. Integrated and reusable in-plane microfludic interconnects. Sensors and Actuators B 132 (2008) 531-539. Exhibit 2016 to PGR2019-00047.
Petition for Post-Grant Review of U.S. Pat. No. 9,977,039 filed on Feb. 21, 2019 for PGR2019-00033.
U.S. Pat. No. 9,977,039 Viola et al., May 22, 2018 Exhibit 1001 to PGR2019-00033.
Declaration of Frank M. LaDuca, Ph.D., FAHA filed on Feb. 21, 2019. Exhibit 1002 to PGR2019-00033.
U.S. Pat. No. 5,534,226 Gavin et al., Jul. 9, 1996. Exhibit 1004 to PGR2019-00033.
U.S. Patent Publication No. 2010/0154520 Schubert et al. Jun. 24, 2010. Exhibit 1005 to PGR2019-00033.
U.S. Pat. No. 6,016,712 Warden et al. Jan. 25, 2000. Exhibit 1006 to PGR2019-00033.
Park IP Translations filed on Feb. 21, 2019. Exhibit 1007 to PGR2019-00033.
Nielsen, V. A comparison of the thrombelastograph and the ROTEM, 2007. Exhibit 1008 to PGR2019-00033.
U.S. Pat. No. 6,225,126 Cohen et al., May 1, 2001. Exhibit 1009 to PGR2019-00033.
U.S. Patent Publication No. 2005/0233460 Clague et al., Oct. 20, 2005. Exhibit 1010 to PGR2019-00033.
Final Written Decision filed on Feb. 21, 2019. Exhibit 1011 to PGR2019-00033.
Final Written Decision filed on Feb. 21, 2019. Exhibit 1012 to PGR2019-00033.
Certificate of Correction for U.S. Pat. No. 9,977,039 filed on Feb. 21, 2019. Exhibit 1003 to PGR2019-00033.
Petitioner's Power of Attorney filed on Feb. 21, 2019 for PGR2019-00033.
Notice of Filing Date Accorded Petition and Time for Filing Patent Owner Preliminary Response filed on Feb. 27, 2019 for PGR2019-00033.
Patent Owner's Power of Attorney filed on Mar. 7, 2019 for PGR2019-00033.
Patent Owner's Mandatory Notices filed on Mar. 7, 2019 for PGR2019-00033.
Patent Owner's Preliminary Response to Petition for Post-Grant Review of U.S. Pat. No. 9,977,039 filed on May 28, 2019 for PGR2019-00033.
Declaration of James P. Landers in Support of Patent Owner's Preliminary Response to Petition for Post-Grant Review Post-Grant Review of U.S. Pat. No. 9,977,039 filed on Mar. 28, 2019. Exhibit 2001 to PGR2019-00033.
James P. Landers Curriculum Vitae filed on Mar. 28, 2019. Exhibit 2002 to PGR2019-00033.
Pertinent Materials Reviewed and Considered by James P. Landers, Ph.D.filed on Mar. 28, 2019. Exhibit 2003 to PGR2019-00033.

(56) References Cited

OTHER PUBLICATIONS

Colman, R. et al. Hemostatis and Thrombosis, 1994. Exhibit 2004 to PGR2019-00033.
Wolberg, A.S. Plasma and cellular contributions to fibrin network formation, structure and stability. Department of Pathology and Laboratory Medicine, University of North Carolina at Chapel Hill, NC. Haemophilia 2010. Exhibit 2005 to PGR2019-00033.
Kuntamukkula, M.S. et al. Rheological Studies of the Contractile Force Within Platlet-Fibrin Clots: Effects of Prostaglandin E1, Dibutyryl-cAMP and Dibutyryl-cGMP. 1978. Exhibit 2006 to PGR2019-00033.
Harrison, P. Assessment of Platelet Function in the Laboratory, 2009. Exhibit 2007 to PGR2019-00033.
Harris, N. et al. Coagulation Tests: A Primer on Hemostasis for Clinical Chemists, 2012. Exhibit 2008 to PGR2019-00033.
Plotkin, A. et al. A Reduction in Clot Formation Rate and Strength Assessed by Thrombelastography is Indicative of Transfusion Requirements in Patients with Penetrating Injuries. The Journal of Trauma Injury, Infection, and Critical Care. 2008. Exhibit 2009 to PGR2019-00033.
Ganter, M. et al. Coagulation Monitoring: Current Techniques and Clinical Use of Viscoelastic Point-of-Care Coagulation Devices, 2008. Exhibit 2010 to PGR2019-00033.
Berney, H. et al. Impedance Measurement Monitors Blood Coagulation, 2008. Exhibit 2011 to PGR2019-00033.
Puckett, L. et al. Monitoring blood coagulation with magnetoelastic sensors. Biosensors and Bioelectornics 18 (2003) 675-681. Exhibit 2012 to PGR2019-00033.
Van den Berg, A. et al. Micro Total Analysis Systems: Microfluidic Aspects, Integration Concept and Applications, 1998, Exhibit 2013 to PGR2019-00033.
Provisional Application for Patent Cover Sheet filed on May 28, 2019. Exhibit 2014 to PGR2019-00033.
Devices, Systems and Methods for Evaluation of Hemostasis, filed on May 28, 2019. Exhibit 2015 to PGR2019-00033.
Evans, P.A. et al. Rheometry and associated techniques for blood cogaulation studies. Medical Engineering & Physics 30 (2008) 671-679. Exhibit 2016 to PGR2019-00033.
Americas Styrenics Styron 666D Polystyrene (Unverified Data), 2019. Exhibit 2017 to PGR2019-00033.
Celanese CoolPoly E1201 Thermally Conductive Polypropylene, 2019. Exhibit 2018 to PGR2019-00033.
Lang, T. et al. Multi-centre investigation on reference ranges for ROTEM thromboelastometry, 2005. Exhibit 2019 to PGR2019-00033.
Alsberg, E. et al. Magnetically-Guided Self-Assembly of Fibrin Matrices with Ordered Nano-Scale Structure for Tissue Engineering. 2006. Exhibit 2020 to PGR2019-00033.
U.S. Patent Publication No. 2007/0059840, Cohen et al. Mar. 15, 2007. Exhibit 2021 to PGR2019-00033.
Liu, C. et al. Dual florescence/contactless conductivity detection for microfluidic chip. Analytica Chimca Acta 621 (2008) 171-177. Exhibit 2022 to PGR2019-00033.
Petitioner's Power of Attorney filed Apr. 20, 2018 for IPR2018-00950.
Petition for Inter Partes Review of U.S. Pat. No. 9,915,671 filed Apr. 20, 2018 for IPR2018-00950.
Declaration of Scott L. Diamond Ph.D. in Support of Hemosonics' Petition to Institute an Inter Partes Review of U.S. Pat. No. 9,915,671 filed on Apr. 20, 2018. Exhibit 1002 to IPR2018-00950.
Curriculum Vitae of Scott L. Diamond filed on Apr. 20, 2018. Exhibit 1003 to IPR2018-00950.
U.S. Pat. No. 5,629,209 Braun, Sr. et al. May 13, 1997. Exhibit 1004 to IPR2018-00950.
Korte, W. et al. Perioperative Gerinnungsstorungen aus hamostaseologischer sicht. 2006. Exhibit 1005 to IPR2018-00950.
Lang, T. et al. Possibilities and Limitations of thromboelastometry/thromboelastography. 2007. Exhibit 1007 to IPR2018-00950.
U.S. Pat. No. 5,204,525, Hillman et al. Apr. 20, 1993. Exhibit 1008 to IPR2018-00950.
U.S. Pat. No. 6,016,712, Warden et al. Jan. 25, 2000. Exhibit 1009 to IPR2018-00950.
Lang, T. et al. Multi-centre investigation on reference ranges for ROTEM thromboelastometry, 2005. Exhibit 1010 to IPR2018-00950.
U.S. Pat. No. 7,676,616, Farnam III, et al. Mar. 9, 2010. Exhibit 1011 to IPR2018-00950.
Wolberg, A.S. Plasma and cellular contributions to fibrin network formation, structure and stability. Department of Pathology and Laboratory Medicine, University of North Carolina at Chapel Hill, NC. Haemophilia 2010. Exhibit 1012 to IPR2018-00950.
Preliminary Amendment filed on Nov. 21, 2016. Exhibit 1013 to IPR2018-00950.
U.S. Patent Publication No. 2009/0130645, Schubert et al. May 21, 2009. Exhibit 1016 to IPR2018-00950.
Weiss, H. et al. The Effect of Salicylates on the Hemostatic Properties of Platlets in Man. The Journal of Clinical Investigation, vol. 47, 1968. Exhibit 1017 to IPR2018-00950.
Pertinent Materials Reviewed and Considered by Scott Diamond, Ph.D. filed on Apr. 20, 2018. Exhibit 1019 to IPR2018-00950.
Colman, R. et al. Hemostatic and Thrombosis, 1994. Exhibit 1020 to IPR2018-00950.
Confidential Pursuant to Protective Order Deposition of Frank Michael LaDuca, Ph.D. on Feb. 13, 2019. Exhibit 1026 to IPR2018-00950.
Reply Declaration of Scott L. Diamond, Ph.D. in Support of Hemosonics LLC's Petition for Inter Partes Review of U.S. Pat. No. 9,915,671 filed on Apr. 4, 2019. Exhibit 1027 IPR2018-00950.
Rotem Delta Targeted Therapy Stop the Bleeding. 2013. Exhibit 1028 to IPR2018-00950.
Petition for Post-Grant Review of U.S. Pat. No. 9,977,039 filed on Apr. 4, 2019. Exhibit 1029 to IPR2018-00950.
Declaration of Frank LaDuac, Ph.D filed on Apr. 4, 2019. Exhibit 1030 to IPR2018-00950.
Confidential Pursuant to Protective Order Deposition John Avila Feb. 5, 2019. Exhibit 1031 to IPR2018-00950.
Notice of Accord of Filing Date Accorded to Petition and Time for Filing Patent Owner Preliminary Response filed on May 8, 2018 for IPR2018-00950.
Patent Owner's Power of Attorney filed May 10, 2018 for IPR2018-00950.
Patent Owner's Mandatory Notices filed May 10, 2018 for IPR2018-00950.
Revised Power of Attorney filed on Jun. 1, 2018 for IPR2018-00950.
Patent's Owner's Updated Mandatory Notices filed on Jun. 8, 2018 for IPR2018-00950.
Patent Owner's Preliminary Response filed on Jul. 20, 2018 for IPR2018-00950.
Decision to Institute filed on Oct. 5, 2018 for IPR2018-00950.
Scheduling Order filed on Oct. 5, 2018 for IPR2018-00950.
Joint Request for Change of Oral Argument Location filed on Oct. 11, 2018 for IPR2018-00950.
Patent Owner's Notice of Deposition of Dr. Scott Diamond filed on Nov. 6, 2018 for IPR2018-00950.
Patent Owner's Response filed on Jan. 4, 2019 for IPR2018-00950.
Declaration of Frank M. LaDuca, Ph.D Exhibit 2001 to Patent Owner's Response filed on Jan. 4, 2019 for IPR2018-00950.
Frank M. LaDuca's Curriculum Vitae. Exhibit 2002 to Patent Owner's Response filed on Jan. 4, 2019 for IPR2018-00950.
Declaration of John Avila (Redacted). Exhibit 2003 to Patent Owner's Response filed on Jan. 4, 2019 for IPR2018-00950.
Declaration of John Avila (Non-Redacted). Exhibit 2003 to Patent Owner's Response filed on Jan. 4, 2019 for IPR2018-00950.
Decision Institution of Inter Partes Review. Exhibit 2006 to Patent Owner's Response filed on Jan. 4, 2010 for IPR2018-00950.
Decision Granting Patent Owner's Motion to Submit Supplemental Information filed on Jan. 4, 2019. Exhibit 2007 to IPR2018-00950.
Declaration of Dr. Scott Diamond, Ph.D. in Support of Hemosonics' Response to the Board's Decision to Institute an Inter Partes Review of U.S. Pat. No. 9,410,971 filed on Jan. 4, 2019. Exhibit 2009 to IPR2018-00950.

(56) References Cited

OTHER PUBLICATIONS

Petitioner's Reply to Patent Owner's Response filed on Jan. 4, 2019. Exhibit 2010 to IPR2018-00950.
Deposition of Scott Diamond on Nov. 15, 2018. Exhibit 2011 to IPR2018-00950.
Patent Owner's Motion to Seal filed on Jan. 7, 2019 for IPR2018-00950.
Jointly Proposed Protective Order filed on Jan. 8, 2019 for IPR2018-00950.
Panel Change Order filed on Jan. 10, 2019 for IPR2018-00950.
Petitioner's Notice of Deposition of John Avila filed on Jan. 25, 2019 for IPR2018-00950.
Petitioner's Notice of Deposition of Frank M. LaDuca Ph.D filed on Jan. 30, 2019 for IPR2018-00950.
Petitioner's Reply to Patent Owner's Response filed on Apr. 4, 2019 for IPR2018-00950.
Patent Owner's Notice of Deposition of Dr. Scott Diamond filed on Apr. 15, 2019 for IPR2018-00950.
Patent Owner's Sur-Reply filed on May 6, 2019 for IPR2018-00950.
Deposition of Scott Diamond on Apr. 26, 2019. Exhibit 2012 to IPR2018-00950.
Order Granting Patent Owner's Motion to Seal and Entering Jointly Propose Protective Order filed on May 15, 2019 for IPR2018-00950.
Patent Owner's Motion to Submit Supplemental Information filed on May 21, 2019 for IPR2018-00950.
Petitioner's Opposition to Patent Owner's Motion to Submit Supplemental Information filed on May 28, 2019 for IPR2018-00950.
Petitioner's Request for Oral Argument filed ion May 29, 2019 for IPR2018-00950.
Patent Owner's Request for Oral Argument filed on Jun. 3, 2019 for IPR2018-00950.
Order Trial Hearing filed on Jun. 5, 2019 for IPR2018-00950.
Decision Granting Patent Owner's Motion to Submit Supplemental Information filed on Jun. 12, 2019 for IPR2018-00950.
HGF, European Application No. 12865280.7, Feb. 18, 2019. Exhibit 2013 to IPR2018-00950.
Communication Pursuant to Article 94(3) EPC for European Application No. 12865280.7, Feb. 18, 2019. Exhibit 2014 to IPR2018-00950.
Claims for the Feb. 19, 2019 Response. Exhibit 2015 to IPR2018-00950.
Petitioner's Power of Attorney filed on Feb. 3, 2017 for IPR2017-00852.
Petition for Inter Partes Review of U.S. Pat. No. 9,272,280 filed on Feb. 3, 2017 for IPR2017-00852.
U.S. Pat. No. 9,272,280, Viola et al. Mar. 1, 2016. Exhibit 1001 to IPR2017-00852.
U.S. Pat. No. 9,410,971, Viola et al. Aug. 9, 2016. Exhibit 1002 to IPR2017-00852.
Declaration of Patrick Mize, Ph.D filed on Feb. 3, 2017. Exhibit 1003 to IPR2017-00852.
Patrick D. Mize, Ph.D. Curriculum Vitae, filed on Feb. 3, 2017. Exhibit 1004 to IPR2017-00852.
U.S. Pat. No. 6,221,672 Baugh et al. Apr. 24, 2001. Exhibit 1005 to IPR2017-00852.
U.S. Patent Publication No. 2010/0154520 Schubert et al. Jun. 24, 2010. Exhibit 1006 to IPR2017-00852.
U.S. Pat. No. 6,016,712 Warden et al. Jan. 25, 2000. Exhibit 1007 to IPR2017-00852.
Lang, T. et al. Different effects of abciximab and cytochalasin D on clot strength in thrombelastography. 2003. Exhibit 1008 to IPR2017-00852.
Issue Notification for U.S. Appl. No. 13/397,398, filed Feb. 3, 2017. Exhibit 1009 to IPR2017-00852.
Ex. 1010: Table of Prior Art Devices filed on Feb. 3, 2017. Exhibit 1010 to IPR2017-00852.
U.S. Patent Publication No. 2003/0113929 Baugh et al. Jun. 19, 2003. Exhibit 1011 to IPR2017-00852.
Patent Owner's Mandatory Notices filed on Feb. 23, 2017 for IPR2017-00852.
Power of Attorney for Patent Owner Hemosonics LLC filed on Feb. 22, 2017 for IPR2017-00852.
Notice of Filing Date Accorded to Petition and Time for Filing Patent Owner Preliminary Response filed on Mar. 6, 2017 for IPR2017-00852.
Patent Owner's Preliminary Response filed on Jun. 6, 2017 for IPR2017-00852.
Patent Owner's Updated Mandatory Notices filed on Jun. 8, 2017 for IPR2017-00852.
Patent Owner's Updated Mandatory Notices filed on Jun. 22, 2017 for IPR2017-00852.
Power of Attorney for Patent Owner Hemosonics LLC filed on Jun. 22, 2017 for IPR2017-00852.
Patent Owner's Updated Exhibit List filed on Jun. 30, 2017 for IPR2017-00852.
Order Conduct of the Proceeding filed on Jul. 10, 2017 for IPR2017-00852.
Correction Citations for the Petition filed on Jul. 27, 2017. Exhibit 1012 to IPR2017-00852.
Decision Institution of Inter Partes Review filed on Sep. 1, 2017 for IPR2017-00852.
Scheduling Order filed on Sep. 1, 2017 for IPR2017-00852.
Patent Owner's Objection to Evidence filed on Sep. 18, 2017 for IPR2017-00852.
Patent Owner's Notice of Deposition of Patrick D. Mize filed on Sep. 26, 2017 for IPR2017-00852.
Patent Owner's Response to the Decision to Institute Inter Partes Review of U.S. Pat. No. 9,272,280 filed on Dec. 1, 2017 for IPR2017-00852.
Patent Owner's Updated Exhibit List filed on Dec. 1, 2017 for IPR2017-00852.
Petitioner's Notice of Deposition of Dr. Scott Diamond filed on Jan. 9, 2018 for IPR2017-00852.
Petitioner's Reply to Patent Owner's Response filed on Mar. 1, 2018 for IPR2017-00852.
Petitioner's Updated Exhibit List filed on Mar. 1, 2018 for IPR2017-00852.
U.S. Pat. No. 9,915,671 Schubert et al. Mar. 13, 2016. Exhibit 1001 to IPR2018-00950.
U.S. Pat. No. 6,221,672 Baugh et al. Apr. 24, 2001. Exhibit 2008 to IPR2018-00950.
U.S. Pat. No. 9,410,971 Viola et al. Aug. 9, 2016. Exhibit 2005 to IPR2018-00950.
U.S. Patent Publication No. 2010/0154520 Schubert et al. Jun. 24, 2010. Exhibit 2004 to IPR2018-00950.
U.S. Pat. No. 7,179,652 Cohen et al. Feb. 20, 2007. Exhibit 1015 to IPR2018-00950.
U.S. Pat. No. 8,110,392 Battrell et al. Feb. 7, 2012. Exhibit 1014 to IPR2018-00950.
U.S. Pat. No. 7,674,616 Farnam III et al. Mar. 9, 2010. Exhibit 1011 to IPR2018-00950.
Decision Denying Institution of Post-Grant Review filed on Oct. 24, 2019 for PGR2019-00047.
U.S. Patent Publication No. 2007/0259348 Phadke et al. Nov. 8, 2017. Exhibit 1014 to PGR2019-00047.
U.S. Pat. No. 5,777,215 Calatzis et al. Jul. 7, 1998, Exhibit 1006 to PGR2019-00047.
U.S. Pat. No. 10,031,144 Viola et al. Jul. 24, 2018. Exhibit 1001 to PGR2019-00047.
U.S. Pat. No. 6,451,610 Gorman et al. Sep. 17, 2002. Exhibit 1025 to PGR2019-00047.
U.S. Pat. No. 5,091,304 La Duca et al. Feb. 25, 1992. Exhibit 1024 to PGR2019-00047.
U.S. Pat. No. 6,613,286 Braun Sr. et al. Sep. 2, 2003. Exhibit 1023 to PGR2019-00047.
U.S. Pat. No. 6,016,712 Warden et al. Jan. 25, 2000. Exhibit 1022 to PGR2019-00047.
U.S. Pat. No. 5,534,226 Gavin et al. Jul. 9, 1996 Exhibit 1021 to PGR2019-00047.
U.S. Patent Publication No. 2005/0148899 Walker et al. Jul. 7, 2005. Exhibit 1018 to PGR2019-00047.

(56) References Cited

OTHER PUBLICATIONS

U.S. Pat. No. 6,221,672 Baugh et al. Apr. 24, 2001. Exhibit 1015 to PGR2019-00047.

Hartert, "Blood Coagulation Studies with Thromboelastography—A New Research Method," Klin Wochanschrift, 28:577-583, Oct. 1948 [English translation].

Soria et al., Path. Biol. Suppl. 22.86 (1974): pp. 1355-1357 (English abstract only).

Soria et al., "Fibrin stabilizing factor (F XIII) and collagent polymerization," Experientia, 31(11). 1355-1357, Nov. 15, 1975.

Rodzynek et al., "The transfer test: a new screening procedure for thrombotic diseases," J Surg Res., 35(3):227-233, Sep. 1983.

Noon et al., "Reduction of blood trauma in roller pumps for long-term perfusion," World J. Surg. 9(1):65-71, Feb. 1985.

Novotny et al., "Platelets secrete a coagulation inhibitor functionally and antigenetically similar to the lipoprotein associated coagulation inhibitor," Blood, 72(6): 2020-2025, Dec. 1986.

Khurana et al., "Monitoring platelet glycoprotein lib/lila-fibrin Interaction with tissue factor-activated thromboelastography," J Lab Clin Med., 130(4): 401-411, Oct. 1997.

Calatzis et al., "Strategies to Assess Individual Susceptibility to abciximab Therapy using a New Function Assay," Annals of Hematology, (Berlin, DE) vol. 78, No. Suppl 1, p. A61, XP009097526, 1998.

Coiffic et al., "Inhibition of platelet aggregation by abciximab but not by aspirin can be detected by a new point-of-care test, the hemostatus," Thromb. Res. 95.2, pp. 83-91, 1999.

Filch et al., "Point-of-care and standard laboratory coagulation testing during cardiovascular surgery: balancing reliability and timeliness," J. Clin. Monit. Comp., 15.3-4, pp. 197-204, 1999.

Goltumukkala et al., "Assessing Platelet and Fibrinogen Contribution to Clot Strenth Using Modified Thromboelastography in Pregnant Women," Anesth. Analg. 89(1999):1453-1455.

Greilich et al., "Near-site monitoring of the antiplatelet drug abciximab using the Hemodyne analyzer and modified thrombelastograph," J Cardiothorac Vasc Anesth. 13(1) 58-64, Feb. 1999.

Shore-Lesserson et al., "Thromboelastography-guided transfusion algorithm reduces transfusions in complex cardiac surgery," Anesth Analg., 88(2): 312-319, Feb. 1999.

Holmes et al., "Novel, Bedside, Tissue Factor-Dependent Clotting Assay Permits Improved Assessment of Combination Antithrombotic and Antiplatelet Therapy," Circ. 102.17, pp. 2051-2057, 2000.

Nielsen et al., "Evaluation of the contribution of platelets to clot strength by thromboelastography in rabbits: the role of tissue factor and cytochalasin D," Anesth Analg., 91(1): 35-39, Jul. 2000.

Salooja and Perry, "Thromboelastography," Blood Coagul Fibrinolysis, 12(5):327-37, Jul. 2001.

Srinivasa et al., "Thromboelastography: Where is it and Where is it Heading?" Int'l Anaesthesiology Clinics, 39(1): 35-49, Winter 2001.

Nield et al., "MRI-based blood oxygen saturation measurements in infants and children with congenital heart disease," Pediatr Radiol., 32(7): 518-522. Epub Apr. 16, 2002.

Spannagi et al., "Point-of-Care Analysis of the Homeostatic System," Laboratoriumsmedizin, (Kirchhsim. DE), 26(1-2): 68-76, Feb. 2002.

Prisco and Panicola, "Point-of-Care Testing of Hemostasis in Cardiac Surgery," Thromb J., 1(1), May 6, 2003.

Lang et al., "Different effects of abciximab and cytochalasin D on clot strength in thrombelastography," J. Thromb. Haemostasis. 2(2004): 147-153.

Lang et al., "Multi-centre investigation on reference ranges for ROTEM thromboelastometry," Blood Coag. Fibrin. 16(2005): 301-310.

Chakroun et al., "The influence of fibrin polymerization and platelet-mediated contractile forces on citrated whole blood thromboealastography profile," Thromb Haemost., 95(5):822-828, May 2006.

Rugeri et al., "Diagnosis of early coagulation abnormalties in trauma patients by rotation thromboelastography," J Throm Haemost., 5(2):289-295, Epub Nov. 16, 2006.

Tucci et al., "Platelet function monitoring with the Sonoclot analyzer after in vitro tirofiban heparin administration," J. Thor. Cardiovasc. Surg. 131.6, pp. 1314-1322, 2006.

Kawasaki et al., "The effects of vasoactive agents, platelet agonists and anticoagulation on thromboelastography," Acta Anaesthesiol Scand., 51(9): 1237-1244, Oct. 2007.

ROTEMS® "When Minutes Count to Stop the Bleeding," Pentapharm GmbH, www.rotem.de, 6 pages, Jun. 2007 [brochure].

Rugeri et al., "Diagnosis of early coagulation abnormalities in trauma patients by rotation thrombelastography," J. Thromb. Haemost. 5(2007):289-295.

Tanaka et al., "Thrombin generation assay and viscoelastic coagulation monitors demonstrate differences in the mode of thrombin inhibition between unfractionaled heparin and bivallrudin," Anath Analg. 105(4): 933-939, Oct. 2007.

Granter et al., "Coagulation monitoring current techniques and clinical use of viscoelastic point-of-care coagulation devices," Anesth. Analg. 106.5, pp. 1366-1375, 2008.

Libgot-Calle et al., "High Frequency Ultrasound Device to Investigate the Acoustic Properties of Whole Blood During Coagulation," Ultrasound Med. Biol. 34.2, pp. 252-264, 2008.

ROTEM Management in Cardiac Surgery "Recommendations for using the ROTEM in the management of perioperative bleeding in Cardiac Surgery," 2008.

Huissoud et al., "Coagulation assessment by rotation thrombelastometry in normal pregnancy," Thromb. Haemostat. 101.4, pp. 755-761, 2009.

Theusinger et al., "Rotation thromboelastometry (ROTEM) stability and reproducibility over time," Eur. J. Cardio-Thor. Surg. 37.3, pp. 677-683, 2009.

Schoochi et al., "Use of rotation thromboelastometry (ROTEM) to achieve successful treatment of polytrauma fibrinogen concentrate and prothrombin complex concentrate," Anaesthesia, 65(2010):199-203.

Viola et al., "A Novel Ultrasound-Based Method to Evaluate Hemostatic Function of Whole Blood," Clin. Chim . Acta. 4111.1-2(2010):106-113.

Venema et al., "An assessment of clinical interchangeability of TEG and RoTEM thromboelastographic variables in cardiac surgical patients," Anesth. Analg. 111.2(2010):339-344.

Mauldin et al., "Adaptive force sonorheometry for assessment of whole blood coagulation," Clin. Chim. Acta. Int. J. Clin. Chem., 411.9-10 pp. 638-644, 2010.

Sinn et al., "Platelet aggregation monitoring with a newly developed quartz crystal microbalance system as an alternative to optical platelet aggregometry," Analyst. 135.11m pp. 2930-2938, 2010.

Lang T., et al., "Different effects of abciximab and cytochalssin D on clot strength in thromboelastography," J. Thromb Haemost. Jan. 2004 2(1): 147-153.

Rumbaul et al., "Platelet-Vessel Wall Interactions in Hemostasis and Thrombosis," San Rafael, CA: Morgan & Clapyool Life Scinces: 2010.

Anonymous: "ROTEM® delta Whole Blood Haemostasis System using Thromboelastometry US Operating Manual," [retrieved on Oct. 30, 2015], Retrieved from the Internet: URL:http://www.sfgh-poct.org/wp-content/uploads/2013/02/ROTEM-delta-US-Operating-Manual-Part-12.pdf, Sep. 2012.

HealthPACT, Rotational thromboelastometry (ROTEM)-targeted therapy for coagulation management in patients with massive bleeding, "Health Policy Advisory Committee on Technology", retrieved from the Internet: <URL: https://www.health.qld.gov.au/_data/assets/pdf_file/0023/427145/wp024.pdf>, 30 pages, Nov. 2012.

Lang et al., "Evaluation of the new device ROTEM platelet" [retrieved on Oct. 28, 2015],. Retrieved from the Interne: <URL: https://www.rotem.de/wp-content/uploads/2014/09/Lang-et-al-2014.pdf>, Jan. 1, 2014.

ROTEM® delta, "Targeted therapy stops the bleeding," 6 pages, Jan. 6, 2014 [brochure].

(56) References Cited

OTHER PUBLICATIONS

ROTEM® delta, "Whole Blood Haemostasis System using Thromboelastometry Operating Manual," 164 pages, Nov. 17, 2014 [brochure].
Office Action of corresponding Japanese Application No. 2016-13279214708706.8, filed Dec. 15, 2009, dated Jul. 21, 2017, 3 pages. English translation of Office Action is included, 4 pages.
European Search Report and Opinion for Application No. 15187347.8, dated Jun. 1, 2016, 16 pages.
International Search Report and Written Opinion for International Application No. PCT/US2016/064790, filed Feb. 15, 2017, 17 pages.
International Search Report and Written Opinion for International Application No. PCT/US2016/064797, dated Feb. 15, 2017, 16 pages.
International Search Report and Written Opinion for International Application No. PCT/US2016/064806, dated Feb. 15, 2017, 18 pages.
International Search Report and Written Opinion for International Application No. PCT/US2016/64800, dated Feb. 16, 2017, 14 pages.
Notification of Reasons for Refusal for Application No. 2015-237571, dated Nov. 7, 2016, 5 pages.
ROTEM®, "Targeted therapy for coagulation management in patients with massive bleeding," https://www.health.qld.gov.au/_data/assets/pdf_file/0023/427145/wp024.pdf, Nov. 2012, 30 pages, [brochure].
European Search Report in European Application No. 15174565.0, dated Nov. 17, 2015, 9 pages.
English translation of Korean Office Action for Application No. 1020167029191, dated Nov. 17, 2016.
European Office Action for Application No. 13167979.7, dated Nov. 15, 2016.
International Search Report and Written Opinion for PCT/IB2016/053860, dated Sep. 19, 2016.
English translation of Japanese Notification of Refusal for Application No. 2011-541392, dated Jun. 14, 2013.
English translation of Japanese Notification of Refusal for Application No. 2014-165975, dated Jul. 17, 2015.
English translation of Korean Office Action for Application No. 10-2011-7017187, dated Mar. 28, 2016.
European Office Action for Application No. 08172769.5, dated Jun. 1, 2011.
European Office Action for Application No. 12179576.09, dated May 22, 2013.
European Office Action for Application No. 13163014.7, dated Mar. 24, 2014.
European Extended Search Report for Application No. 13167983.9, dated Nov. 6, 2013.
International Preliminary Report for Application No. PCT/EP2009/067181, dated Jun. 29, 2011.
International Search Report and Written Opinion for Application No. PCT/EP2009/067181, dated Mar. 22, 2010.
English translation of Chinese Office Action for Application No. 200980151858.5, dated Feb. 14, 2014.
English translation of Chinese Office Action for Application No. 200980151858.5, dated May 21, 2013.
Chinese Office Action for Application No. 200960151858.5, dated Apr. 15, 2013.
European Search Report for EP 07121222, dated Apr. 9, 2008.
European Search Report for EP 08172769 completed May 18, 2009, 1 page.
European Search Report for EP 09150740 completed Jun. 30, 2009, 1 page.
International Preliminary Report and Written Opinion for PCT/EP2011/051803, dated Sep. 25, 2012.
International Preliminary Report on Patentability for PCT/EP2010/050454, dated Jul. 19, 2011, 4 pages.
International Preliminary Report and Written Opinion for PCT/EP2010/050454, dated Apr. 20, 2010, 6 pages.
International Search Report and Written Opinion for PCT/EP2011/051803.
Fatemi, et al., "Application of radiation force in noncontact measurement of the elastic parameters," Ultrasonic Imaging, vol. 21, No. 2, Apr. 1999 pp. 147-154.
Fatemi, et al., "Ultrasound-Stimulated Vibro-Acoustic Spectography," Science Magazine, vol. 280, No. 5360, 1998, pp. 82-85.
Ferraris, et al., "2011 Update to the Society of Thoracic Surgeons and the Society of Cardiovascular Anesthesiologists Blood Conservation Clinical Practice Guidelines," Annals of Thoracic Surgery, vol. 91, 2011, pp. 944-982.
Fertner, et al., "Comparison of Various Time Delay Estimation Methods by Computer Simulation," IEEE Transactions on Acoustics, Speech, and Signal Processing, vol. 34, No. 5, 1986, pp. 1329-1330.
Flax, et al., "Phase-Aberration Correction Using Signals from Point Reflectors and Diffuse Scatterers: Basic Principles," IEEE Transactions on Ultrasonics Ferroelectrics & Frequency Control, vol. 35, No. 6, Nov. 1988, pp. 758-767.
Gaetano, G. de, et al., "Effect of Platelets on Clot Structuration, a Thrombelastographic Study," Thrombosis Research, vol. 3, No. 4, pp. 425-435, 1973.
Ganter, et al., "Active, personalized, and balanced coagulation management saves lives in patients with massive bleeding," Anesthesiology, vol. 133, No. 5, Nov. 2010, pp. 1016-1018.
Gallippi, et al., "Adaptive clutter filtering via blind source," Ultrasonic Imaging, vol. 24, No. 4, 2002, pp. 193-214.
Gallippi, et al., "BSS-based filtering of physiological and ARFI induced tissue and blood motion," Ultrasound in Medicine and Biology, vol. 29, No. 11, 2003, pp. 1583-1592.
Gallippi, et al., "Complex blind source separation for acoustic radiation force impulse imaging in the peripheral vasculature, in vivo," IEEE Ultrasonics Symposium, vol. 1, 2004, pp. 596-601.
Gauss, et al., "Adaptive Imagining in the Thyroid Using Fundamental and Harmonic Echo Data," presented at IEEE Ultrasonics Symposium, 1999, pp. 1515-1519.
Gauss, et al., "Wavefront Estimation in the Human Breast," presented at SPIE Medical Imaging, vol. 4325, 2001, pp. 172-180.
Giunta, et al., "Estimation of Global Motion Parameters by Complex Linear Regression," IEEE Transactions on Image Processing, vol. 8, No. 11, 1999, pp. 1652-1657.
Glidden, Paul F., et al., "Thromboelastograph Assay for Measuring the Mechanical Strength of Fibrin Sealant Clots," Clinical and Applied Thombosis / Hemostasis, vol. 6, No. 4, Oct. 2000, pp. 226-233.
Greilich, Philip E., et al., "A Modified Thromboelastographic Method for Monitoring c7E3 Fab in Heparinized Patients," Anesth Analg, vol. 84, 1997, pp. 31-38.
Gurbel, et al., "Platelet function monitoring in patients with coronary artery disease," Journal of the American College of Cardiology, vol. 50, No. 19, Nov. 2007, pp. 1822-1834.
Hardisty R. M. et al., "Fibrinogen as a Co-factor in the Reaction of Platelets with Kaolin," May 7, 1966, Nature Publishing Group, Edition 210, vol. 644 (http://www.nature.com/nature/journal/v210/n5036/abs/210644a0.html).
Hartley, et al., "Characteristics of Acoustic Streaming Created and Measured by Pulsed Doppler Ultrasound," IEEE Transactions on Ultrasonics, Ferroelectrics, and Frequency Control, vol. 44, No. 6, Nov. 1997, pp. 1278-1285.
Hartley, et al., "Doppler Measurement of Acoustic Streaming," IEEE Ultrasonics Symposium Proceedings, 1995, pp. 1537-1540.
Hirsh, et al., "Management of deep vein thrombosis and pulmonary embolism. A statement for healthcare professionals," Council on Thrombosis (in consultation with the Council on Cardiovascular Radiology), American Heart Association, vol. 93, 1996, 55 pages.
Huang, et al.,"Characterization of Blood Properties from Coagulating Blood of Different Hematocrits Using Ultrasonic Backscatter and Attenuation", Japanese Journal of Applied Physics, vol. 45, No. 9A, 2006, pp. 7191-7196.
Huang, et al., "Detection of blood coagulation and clot formation using quantitative ultrasonic parameters," Ultrasound in Medicine and Biology, vol. 31, No. 11, Nov. 2005, pp. 1567-1573.

(56) References Cited

OTHER PUBLICATIONS

Ivandic et al., "Determination of Clopidogrel Resistance by Whole Blood Platelet Aggregometry and Inhibitors of the P2Y12 Receptor". Clinical Chemistry, vol. 52, No. 3, Mar. 2006, pp. 383-388. PubMed P.M.I.D.: 16423907.
Jacovitti, et al., "Discrete Time Techniques for Time Delay Estimation," IEEE Transactions on Signal Processing, vol. 41, No. 2, Feb. 1993, pp. 525-533.
Jensen, "A New Method for Estimation of Velocity Vectors," IEEE Transactions on Ultrasonics, Ferroelectrics and Frequency Control, vol. 45, No. 3, 1998, pp. 837-851.
Jensen, et al., "Calculation of pressure fields from arbitrarily shaped, apodized, and excited ultrasound transducers," IEEE Transactions on Ultrasonics, Ferroelectrics, and Frequency Control, vol. 39, 1992, pp. 262-267.
Kadi, et al., "On the performance of regression and step-initialized IIR Clutter Filters," IEEE Transactions on Ultrasonics, Ferroelectrics, and Frequency Control, vol. 42, 1995, pp. 827-837.
Kasai, et al., "Real-time Two-Dimensional Blood Flow Imaging Using an Autocorrelation Technique," IEEE Ultrasonics Symposium, vol. 32, No. 3, 1985, pp. 458-464.
Katori, et al., "The effects of platelet count on clot retraction and tissue plasminogen activator-induced fibrinolysis on thrombelastography," Anesthesia and Analgesia, vol. 100, No. 6, Jun. 2005, pp. 1781-1785.
Keresztes, et al., "The PFA-100: analysis and interpretation of a platelet function measurement," The Journal of Cardiovascular Nursing, vol. 20, No. 6, 2005, pp. 405-407.
Kettner, S.C., et al., "Use of abciximab-Modified Thrombelatography in Patients Undergoing Cardiac Surgery," Anesth Analg, vol. 89, 1999, pp. 580-584.
Kruse, et al., "A new high-resolution color flow system using an eigendecomposition-based adaptive filter for clutter rejection," IEEE Transactions on Ultrasonics, Ferroelectrics, and Frequency Control, vol. 49, No. 10, 2007, pp. 1384-1399.
Ledoux, et al., "Reduction of the clutter component in Doppler ultrasound signals based on singular value decomposition: a simulation study," vol. 19, No. 1, 1997, pp. 1-18.
Lerner, et al., "Sono-elasticity: medical elasticity images derived from ultrasound signals in mechanically vibrated targets," Ultrasound in Medicine & Biology, vol. 16, 1998, pp. 317-327.
Vig, et al., "Thromboelastography: a reliable test?" Blood Coagulation and Fibrinolysis, vol. 12, No. 7, Oct. 2001.
Viola, et al., "A Comparison between spline-based and phase domain time-delay estimators," IEEE Transactions on Ultrasonics, Ferroelectrics, and Frequency Control, vol. 53, No. 3, 2006, pp. 515-517.
Viola, et al., "A comparison of the performance of time-delay estimators in medical ultrasound," IEEE Transactions on Ultrasonics Ferroelectrics & Frequency Control., vol. 50, 2003, pp. 392-401.
Viola, et al., "A Spline Based Algorithm for Continuous Time Delay Estimation Using Sampled Data," IEEE Transactions on Ultrasonics Ferroelectrics & Frequency Control, in press, 2005, pp. 80-93.
Viola, et al., "Analysis of Clot Formation with Acoustic Radiation Force," SPIE Proceedings, vol. 4689, 2002, pp. 235-242 and pp. 1-2.
Viola, et al., "Comparison of Time Delay Estimators in Medical Ultrasound," IEEE Ultrasonics Symposium, vol. 2, 2001, pp. 1485-1488.
Viola, et al., "Efficient and Accurate Spline-Based Time Delay Estimation," IEEE Ultrasonics Symposium, vol. 2, 2004, pp. 870-873.
Viola, et al., "Imaging Viscoelastic Properties of the Vitreous," Ultrasonics Symposium, vol. 2, 2001, pp. 1623-1626.
Viola, et al., "Radiation Force Imaging of Viscoelastic Properties with Reduce Artifacts," IEEE Transactions on Ultrasonics, Ferroelectrics, and Frequency Control, vol. 50, No. 6, 2003, pp. 736-742.
Viola, et al., "Ultrasound echo decorrelation due to acoustic radiation force," IEEE Ultrasonics Symposium Proceedings, vol. 2, 2002, pp. 1903-1906.
Voleišis, A., et al., "Ultrasonic method for the whole blood coagulation analysis," Ultrasonics, vol. 40, May 2002, pp. 101-107.
Walker, et al., "A Fundamental Limit on Delay Estimation Using Partially Correlated Speckle Signals," IEEE Transactions on Ultrasonics, Ferroelectrics and Frequency Control, vol. 42, 1995, pp. 301-308.
Walker, et al., "A Fundamental Limit on the Accuracy of Speckle Signal Alignment," IEEE Ultrasonics Symposium Proceedings, vol. 3, 1994, pp. 1787-1791.
Walker, et al., "A Method of Imagining Viscoelastic Parameters with Acoustic Radiation Force," Physics in Medicine and Biology, vol. 45, No. 6, 2000, pp. 1437-1447.
Walker, et al., "Application of Acoustic Radiation Force in Ophthalmic Ultrasound," Proc. IEEE Ultrason. Symp., vol. 2, 1997, pp. 1291-1295.
Walker, et al., "Real-Time Imaging of Tissue Vibration Using a Two-Dimensional Speckle Tracking System," IEEE Ultrason. Symp., 1993, pp. 873-877.
Walker, et al., "The Significance of Correlation in Ultrasound Signal Processing," SPIE Proceedings, vol. 4325, 2001, pp. 159-171.
Westbrook, et al., "Protocol based on thromboelastograph (TEG) out-performs physician preference using laboratory coagulation tests to guide blood replacement during and after cardiac surgery: a pilot study," Heart, Lung, and Circulation, vol. 18, No. 4, Aug. 2009, pp. 277-288.
Whitten, et al., "Thromboelastography: past, present, and future," Anesthesiology, vol. 92, No. 5, May 2000, pp. 1223-1225.
Yu, et al., "Single-Ensemble-Based Eigen-Processing Methods for Color Flow Imaging," IEEE Transactions on Ultrasonics, Ferroelectrics, and Frequency Controls, vol. 55, No. 3, 2008, pp. 573-587.
Azar et al., "Abciximab in Primary Coronary Angioplasty for Acute Myocardial Infarction Improves Short-and Medium-Term Outcomes", J. Am. Coll. Cardiol., Dec. 1998; 32 (7): 1996-2002. PubMed P.M.I.D.: 9857884.
Born, G.V., "Aggregation of Blood Platelets by Adenosine Diphosphate and its Reversal". Nature, Jun. 9, 1962; 194: 927-9. PubMed P.M.I.D.: 13871375.
Callé et al., "Evaluation of the Sensitivity of an in vitro High Frequency Ultrasound Device to Monitor the Coagulation Process: Study of the Effects of Heparin Treatment in a Murine Model". Ultrasound Med. Biol., Feb. 2010; 36 (2): 295-305. PubMed P.M.I.D.: 20045589.
Delhaye et al., Temperature corrected thromboelastometry in hypothermic trauma patients: 6AP24. European Journal of Anaesthesiology, May / Jun. 2008, 25:84.
Dorn-Beineke et al., "Evaluation of the Automated Coagulation Analyzer Sysmex CA—7000". Thromb. Res., 2005; 116 (2): 171-9. PubMed P.M.I.D.: 15907533.
Eikelboom et al., "Monitoring Unfractionated Heparin with the aPTT: Time for a Fresh Look". Thromb. Haemost. Nov. 2006; 96 (5): 547-52. Review. PubMed P.M.I.D.: 17080209.
Flanders et al., "Evaluation and Performance Characteristics of the STA-R Coagulaton Analyzer". Clin Chem., Sep. 2002; 48 (9): 1622-1624. PubMed P.M.I.D.: 12194955.
Ganter et al., "Kaolin-Based Activated Coagulation Time Measured by Sonoclot in Patients Undergoing Cardiopulmonary Bypass." J. Cardiothorac. Vasc. Anesth. Aug. 2007; 21 (4): 524-8. PubMed P.M.I.D.: 17678778.
Gosselin et al., "Monitoring Oral Anticoagulant Therapy with Point-of-Care Devices: Correlations and Caveats", Clin. Chem., Sep. 1997; 43 (9): 1785-6. PubMed P.M.I.D.: 9299978.
Harrison, P. Platelet Function Analysis, Blood Rev. Mar. 2005; 19 (2): 111-23, Review. PubMed P.M.I.D.: 15603914.
Jobes et al., "Increased Accuracy and Precision of Heparin and Protamine Dosing Reduces Blood Loss and Transfusion in Patients Undergoing Primary Cardiac Operations". J. Thorac. Cardiovasc. Surg. Jul. 1995; 110 (1): 36-45. PubMed P.M.I.D.; 7609566.
Kereiakes et al., "Time Course, Magnitude, and Consistency of Platelet Inhibition by Abciximab, Tirofiban, or Eptilibatide in Patients

(56) References Cited

OTHER PUBLICATIONS with Unstable Angina Pectoris Undergoing Percutaneous Coronary Intervention", Am. J. Cardiol., Aug. 15, 1999; 84 (4): 391-5 .PubMed P.M.I.D.: 10468074.

Koster et al., "Evaluation of Post-Cardiopulmonary Bypass Coagulation Disorders by Differential Diagnosis with a Multichannel Modified Thromboelastogram: A Pilot Investigation". J. Extra. Corpor. Technol., Sep. 2001; 33 (3): 153-8. PubMed P.M.I.D.: 11680728.

Li et al., "The Xylum Clot Signature Analyzer: A Dynamic Flow System that Simulates Vascular Injury". Thromb. Res., Dec. 15, 1998; 92 (6 Suppl. 2): S67-77. PubMed P.M.I.D.: 9886913.

Machado et al., "Evaluation of an Ultrasonic Method Applied to the Measurement of Blood Coagulation Time". Physiol. Meas., May 1997; 18 (2): 129-43. PubMed P.M.I.D.: 9183807.

Motovska et al., "Benefits and Risks of Clopidogrel Use in Patients with Coronary Artery Disease: Evidence from Randomized Studies and Registries". Clin. Ther., 2008; 30 Pt. 2: 2191-202. J. Clinthera., 2008.12.001. Review. PubMed P.M.I.D.: 19281914.

Mueller et al., "Utility of the PFA-100 Instrument and the Novel Multiplate Analyzer for the Assessment of Aspirin and Clopidogrel Effects on Platelet Function in Patients with Cardiovascular Disease". Clin. Appl. Thromb. Hemost., Dec. 2009; 15 (6): 652-9. PubMed P.M.I.D.: 18805846.

Nam et al., "Evaluation of the Roche CoaguChek XS Handheld Coagulation Analyzer in a Cardiac Outpatient Clinic". Ann. Clin. Lab. Sci., 2008 Winter; 38 (1): 37-40. PubMed P.M.I.D.: 18316780.

Price et al., "Prognostic Significance of Post-Clopidogrel Platelet Reactivity Assessed by a Point-of-Care Assay on Thrombotic Events after Drug-Eluting Stent Implantation", Eur. Heart Apr. 2008; 29 (8): 992-1000. PubMed P.M.I.D.: 18263931.

Ruzicka, K., et al. Evaluation of Bedside Prothrombin Time and Activated Partial Thromboplastin Time Measurement by Coagulation Analyzer COAGUCHECK PLUS in Various Clinical Settings. Throm. Res., 87 (5) 1997 pp. 431-440. See also, Hillman, R., 1988 U.S. Pat. No. 4,756,884, Capillary Fill Device.

Kozek-Langenecker, S. Intensive Care Medicine, Annual Update 2007, Monitoring of Hemostasis in Emergency Medicine, pp. 847-860, Springer New York.

Scharbert et al., "Evaluation of the Platelet Mapping Assay on Rotational Thromboelastometry ROTEM". Platelets. Mar. 2009; 20 (2): 125-30. PubMed P.M.I.D. 19235055.

Taborski et al., "Analytical Performance of the New Coagulation Monitoring System INRatio for the Determination of INR Compared with the Coagulation Monitor Coaguchek S and an Established Laboratory Method" J. Thromb. Thrombolysis. Oct. 2004; 18 (2): 103-7. PubMed P.M.I.D.: 15789176.

Tripodi et al., "International Sensitivity Index Calibration of the Near-Patient Testing Prothrombin Time Monitor, Pro Time". Am. J. Clin. Pathol., Feb. 2003; 119 (2): 241-5. PubMed P.M.I.D.: 12579994.

Versteeg et al., "New Fundamentals in Hemostasis", Physiol. Rev. Jan. 2013; 93 (1): 327-58. Review. PubMed P.M.I.D.: 23303912.

Wolff et al., "Aspirin for the Primary Prevention of Cardiovascular Events: an Update of the Evidence for the U.S. Preventive Services Task Force". Ann. Intern. Med., Mar. 17, 2009; 150 (6): 405-10. Review. PubMed P.M.I.D.: 19293073.

Fricke, W., Kouides, P., Kessler, C., Schmaier, A.H., Krijanovski, Y., Jagadeesen, K., Joist, J., A multicenter clinical evaluation of the Clot Signature Analyzer. J. Thromb. Hasemostasis. 2004; 2: 763-8.

Shore-Lesseron., Evidence Based Coagulation Monitors: Heparin Monitoring, Thromboelastography, and Platelet Function. Sem. Cardiothoracic Vasc. Anesthesia., Mar. 2005; 9 (1): 42-52.

Tomauiolo, M., Brass, L.F., Stalker, T.J., Regulation of Platelet Activation and Coagulation and Its Role in Vascular Injury and Arterial Thrombosis. Interv. Cardiol. Clin. Jan. 2017; 6 (1): 1-12.

International Search Report & Written Opinion of the International Searching Authority, received in corresponding application No. PCT/US2010/049342, dated Nov. 16, 2010.

International Search Report & Written Opinion of the International Searching Authority, received in corresponding application No. PCT/US2011/031832, dated Dec. 15, 2011.

International Search Report, dated Sep. 30, 2013, in connection with International Application No. PCT/US2012/025270.

International Search Report, dated Aug. 20, 2013, in connection with International Application No. PCT/US2012/025278.

International Search Report, dated Jan. 2, 2013, in connection with International Application No. PCT/US2012/038553.

International Preliminary Report on Patentability & Written Opinion, dated Oct. 8, 2013, in connection with International Application No. PCT/US2012/025270.

International Preliminary Report on Patentability & Written Opinion, dated Aug. 27, 2013, in connection with International Application No. PCT/US2012/025278.

International Preliminary Report on Patentability & Written Opinion, dated Nov. 18, 2013, in connection with International Application No. PCT/US2012/038553.

International Preliminary Report on Patentability & Written Opinion, dated Oct. 9, 2012, in connection with International Application No. PCT/US2011/031832.

International Preliminary Report on Patentability & Written Opinion, dated Mar. 20, 2012, in connection with International Application No. PCT/US2010/049342.

Communication pursuant to Rule 114(2) EPC issued in European Patent Application No. 12865280.7, dated Dec. 13, 2016, 5 pages.

Communication pursuant to Rule 94(3) EPC issued in European Patent Application No. 12865280.7, dated Jul. 3, 2017, 3 pages.

Communication pursuant to Rule 94(3) EPC dated Apr. 3, 2018 in co-pending Application EP 12865280.7.

Communication pursuant to Rule 94(3) EPC, issue for European Application No. 12865280.7, dated Oct. 8, 2018, 17 pages.

Communication pursuant to Rule 94(3) EPC issued for European Patent Application No. 12865280.7, dated Mar. 18, 2019, 7 pages.

Extended European Search Report issued in European Patent Application No. 11766842.6, dated Oct. 21, 2015, 10 pages.

Extended Search Report issued in European Patent Application No. 12865280, dated Oct. 24, 2016, 5 pages.

EP Extended Search Report, dated Oct. 24, 2016, in co-pending International Application No. PCT/US2012/025270.

*Instrumentation Laboratory Co.* v. *HemoSonics LLP*, IPR201700852, Paper No. 47 (PTAB Feb. 13, 2019) ("852 FWD"), 25 pages.

*Instrumentation Laboratory Co.* v. *HemoSonics LLP*, IPR201700855, Paper No. 55 (PTAB Feb. 13, 2019) ("971 FWD"), 55 pages.

Examination Report issued in European Application No. 12865280.7, dated Apr. 3, 2018, 3 pages.

Examination Report issued in European Application No. 12865280.7, dated Mar. 7, 2017, 3 pages.

Examination Report issued in Australian Application No. 2012364908, dated Jun. 27, 2017, 5 pages.

Examination Report issued in Australian Application No. 2012364908, dated Jul. 23, 2016, 4 pages.

Examination Report issued for Australian Application No. 2017248548, dated Jul. 9, 2018.

Advisory Action received in co-pending U.S. Appl. No. 15/202,059, dated Sep. 21, 2017.

Office Action received in U.S. Appl. No. 15/357,492, dated Jun. 22, 2017.

Office Action received in co-pending U.S. Appl. No. 15/202,059, dated Oct. 4, 2016.

Office Action received in co-pending U.S. Appl. No. 15/202,059, dated Jul. 13, 2017.

Office Action received in co-pending U.S. Appl. No. 15/202,059, dated Jan. 12, 2018.

Office Action received in co-pending U.S. Appl. No. 15/644,124, dated Sep. 7, 2017.

Office Action received in co-pending U.S. Appl. No. 15/644,124, dated Nov. 29, 2017.

Office Action received in co-pending U.S. Appl. No. 15/644,124, dated Feb. 6, 2018.

Office Action issued for U.S. Appl. No. 15/904,984, dated Jul. 12, 2018.

(56) References Cited

OTHER PUBLICATIONS

Office Action issued for Canadian Application No. 2,823,729, dated Mar. 9, 2018.
Office Action issued for Canadian Application No. 2823729, dated Nov. 14, 2018, 4 pages.
Office Action issued for Chinese Application No. 2017101635956, dated Jul. 17, 2018.
Notice of Allowance issued for U.S. Appl. No. 15/991,677, dated Nov. 2, 2018.
Notice of Allowance issued for U.S. Appl. No. 15/202,059, dated May 23, 2018.
Corrected Notice of Allowance issued for U.S. Appl. No. 15/202,059, dated Jun. 22, 2018.
Trial Board Order for Inter Partes Review of U.S. Pat. No. 9,272,280 B2, 13 pages.
Trial Board Order for Inter Partes Review of U.S. Pat. No. 9,410,971 B2, 27 pages.
Trial Paper for Inter Partes Review of U.S. Pat. No. 9,272,280 B2 dated Jul. 11, 2018 10 pages.
Trial Paper for Inter Partes Review of U.S. Pat. No, 9,410,971 dated Jul. 11, 2018, 10 pages.
Trial Paper for Inter Partes Review of U.S. Pat. No. 9,410,971 dated Aug. 28, 2018, 3 pages.
Trial Paper for Inter Partes Review of U.S. Pat. No. 9,410,971 dated Oct. 2, 2017, 11 pages.
Trial Paper for Inter Partes Review of U.S. Pat. No. 9,410,971 dated Dec. 1, 2017, 4 pages.
Patent Owner's Response for Inter Partes Review of U.S. Pat. No. 9,915,671, dated Jan. 4, 2019, 37 pages.
Patent Owner's Response to the Decision to Institute Inter Partes Review of U.S. Pat. No. 9,272,280, dated Dec. 1, 2017, 39 pages.
Patent Owner's Response to the Decision to Institute Inter Partes Review of U.S. Pat. No. 9,410,971, entered Dec. 1, 2017, 59 pages.
Third party observation filed to European Patent Application No. 11766842.6, dated Mar. 6, 2016, 10 pages.
Third party observation filed in U.S. Appl. No. 15/202,059, filed Nov. 30, 2016, 40 pages.
Declaration of U.S. Pat. No. 9,272,280, 67 pages.
Declaration of U.S. Pat. No. 9,410,971, 124 pages.
Japanese Office Action in International Application No. JP2015191180, dated Nov. 17, 2017, (9 pages including English Translation).
Loupas, et al., "An axial Velocity Estimator for Ultrasound Blood flow imaging, by means of a two-dimensional autocorrelation approach," IEEE Transactions on Ultrasonics, Ferroelectrics, and Frequency Control, vol. 42, No. 4, pp. 672-668.
Lubinski, et al., "Adaptive strain estimation using retrospective processing medical US elasticity imaging," IEEE Transactions on Ultrasonics Ferroelectrics & Frequency Control, vol. 46, 1999, pp. 97-107.
Mahla, et al., "Thromboelastography for monitoring prolonged hypercoagulability after major abdominal surgery," Anesthesia and Analgesia, vol. 92, No. 3, Mar. 2001, pp. 572-577.
Mauldin, et al., "Robust Principal Component Analysis and Clustering Methods for Automated Classification of Tissue Response to ARFI Excitation," Ultrasound in Medicine & Biology, vol. 34, No. 2, 2008, pp. 309-325.
Ng, et al., "A Comparative Evaluation of Several Algorithms for Phase Aberration Correction," IEEE Transactions on Ultrasonics Ferroelectrics & Frequency Control, vol. 41, No. 5, Sep. 1994, pp. 631-643.
McAleavey, et al., "Estimates of echo correlation and measurement bias in acoustic radiation force impulse imaging," IEEE Transactions on Ultrasonics Ferroelectrics & Frequency Control, vol. 50, 2003, pp. 631-641.
Nielson, et al., "Effects of coagulation factor deficiency on plasma coagulation kinetics determined via thrombelastography: critical roles of fibrinogen and factors II, VII, X and XII," Acta Anesthesiologica Scandanavia, vol. 49, No. 2, Feb. 2005, pp. 222-231.

Nightingale, et al., "Shear-Wave Generation Using Acoustic Radiaton Force: In Vivo and EX Vivo Results," Ultrasound in Medicine & Biology, vol. 29, No. 12, 2003, pp. 1715-1723.
Nightingale, et al., "Acoustic Radiation Force Impulse Imaging: In Vivo Demonstration of Clinical Feasibility," Ultrasound in Medicine & Biology, vol. 28, 2002, pp. 227-235.
Nightingale, et al., "Acoustic remote palpation: initial in vivo results," presented at IEEE Ultrasonics Symposium, 2000, pp. 1553-1558.
Oberhardt, et al., "Dry reagent technology for rapid, convenient measurements of blood coagulation and fibrinolysis," Clinical Chemistry, vol. 37, No. 4, Apr. 1991, pp. 520-526.
O'Donnell, et al., "Role of the Thrombelastograph as an adjunctive test in thrombophilia screening," Blood Coagulation and Fibrinolysis, vol. 15, No. 3, Apr. 2004, pp. 207-211.
O'Donnell, et al., "Internal Displacement and Strain Imaging using Ultrasonic Speckle Tracking," IEEE Transactions on Ultrasonics, Ferroelectrics and Frequency Control, vol. 41, 1994, pp. 314-325.
Ophir, et al., "Elastography: A Quantitative Method for Imaging the Elasticity of Biological Tissues," Ultrasonic Imaging, vol. 13, No. 2, 1991, pp. 111-134.
Packham, M., "Role of platelets in thrombosis and hemostasis," Canadian Journal of Physiology and Pharmacology, vol. 72, No. 3, Mar. 1994, pp. 278-284.
Palmeri, et al., "Ultrasonic tracking of acoustic radiation force-induced displacements in homogeneous media," IEEE Transactions on Ultrasonics, Ferroelectrics, and Frequency Control, vol. 53, No. 7, 2006, pp. 1300-1313.
Parsons, et al., "Age Determiniation of Experimental Venous Thrombi by Ultrasonic Tissue Characterization," Journal of Vascular Surgery, vol. 17, 1993, 470-478.
Patil, et al., "3D prostate elastography: algorithm, simulations and experiments," Physics in Medicine & Biology, vol. 52, No. 12, 2007, pp. 3643-3663.
Perry, et al., "Point-of-care testing in haemostasis," British Journal of Haematology, vol. 150, No. 5, Sep. 2010, pp. 501-514.
Pivalizza, et al., "Perioperative thromboelastography and sonoclot analysis in morbidly obese patients," Canadian Journal of Anaesthesia, vol. 44, No. 9, Sep. 1997, pp. 942-945.
Rao, G., "Need for a point-of-care assay for monitoring antiplatelet and antithrombotic therapies," Stroke, vol. 40, No. 6, Jun. 2009, pp. 2271-2272.
Riou, Chonavel et al., "Fast adaptive eigenvalue decomposition: a maximum likelihood approach," Signal Processing, 83, 2003, pp. 307-324.
Rubin, et al., "Clinical application of sonographic elasticity imaging for aging of deep venous thrombosis: preliminary findings," Journal of Ultrasound in Medicine, vol. 22, 2003, pp. 443-448.
Sakharov, et al., "Acceleration of Fibrinolysis by High-Frequency Ultrasound: The Contribution of Acoustic Streaming and Temperature Rise," Thrombosis Research, vol. 100, No. 4, 2000, pp. 333-340.
Sarvazyan, et al., "Shear Wave Elasticity Imagining—A New Ultrasonic Technology of Medical Diagnostics," Ultrasound in Medicine and Biology, vol. 24, 1998, pp. 1419-1436.
Schmitt, C., et al., "Characterization of blood clot viscoelasticity by dynamic ultrasound elastography and modeling of the rheological behavior," Journal of Biomechanics, vol. 44, No. 4, 2011, pp. 622-629.
Shi, Quantitative Investigation of Acoustic Streaming in Blood, J. Acoust. Soc. Am. 111, Feb. 2002, pp. 1110-1121.
Shi, et al., "Color Doppler Detection of Acoustic Streaming in a Hematoma Model," Ultrasound in Medicine and Biology, vol. 27, No. 9, 2001, pp. 1255-1264.
Shi, et al., "Color Doppler imaging of acoustic streaming in blood and clot," IEEE Ultrasonics Symposium, vol. 2, 1999, pp. 1315-1318.
Shi, et al., "Experimental Investigation and Finite Element Simulation of Streaming in Blood in Cylindrical Models," IEEE Ultrasonics Symposium, vol. 2, 2000, pp. 1509-1512.

(56) References Cited

OTHER PUBLICATIONS

Shih, C-C, et al., "In Vitro Assessments of Viscoelastic Properties of Fibrin Clot by Using Acoustic Radiation Force on a Solid Sphere," International Ultrasonics Symposium Proceedings, IEEE, 2010, pp. 479-482.
Shung, et al., "Ultrasonic characterization of blood during coagulation," Journal of Clinical Ultrasound, vol. 12, No. 3, 1984, pp. 147-153.
Skovoroda, et al., "Tissue elasticity reconstruction based on ultrasonic displacement and strain images," IEEE Transactions on Ultrasonics, Ferroelectrics, and Frequency Control, vol. 42, No. 4, 1995, pp. 747-765.
Spiel, A. O. et al,, "Validation of rotation thrombelastography in a model of systemic activation of fibrinolysis and coagulation in humans", Journal of Thrombosis and Haemostasis, 2006; 4: 411-416.
Srinivasan, et al., "Elastographic imaging using staggered strain estimates," Ultrasonic Imaging, vol. 24, 2002, pp. 229-245.
Strobach, P., "Low-rank adaptive filters," IEEE Trans Signal Process, vol. 44, No. 12, 1996, pp. 2932-2947.
Sugimoto, et al., "Tissue Hardness Measurement Using the Radiation Force of Focused Ultrasound," Proc. IEEE Ultrason. Symp., 1990, pp. 1377-1380.
Sumino, et al., "Measurements of ultrasonic pulse arrival time differences produced by abdominal wall specimens," Journal of the Acoustical Society of America, vol. 90, No. 6, 1991, pp. 2924-2930.
Thuerlemann, et al., "Monitoring thrombin generation by electrochemistry: development of an amperometric biosensor screening test for plasma and whole blood," Clinical Chemistry, vol. 55, No. 3, Mar. 2009, pp. 505-512.
Toner, et al., "Blood-on-a-chip," Annual Review of Biomedical Engineering, vol. 7, 2005, pp. 77-103.
Torr, "The Acoustic Radiation Force," Am. J. Phys., vol. 52, 1984, pp. 402-408.
Trahey, et al., "Synthetic receive aperture imaging with correction for motion and for tissue inhomogeneities. II. Effects of and correction for motion," IEEE Transactions on Ultrasonics, Ferroelectrics, and Frequency Control, vol. 39, No. 4, 1992, pp. 496-501.
Petition for Inter Partes Review of U.S. Pat. No. 10,746,750 dated Dec. 14, 2020, 79 pages.
Janus TJ, Lewis SD, Lorand L, Shafer JA, Promotion of thrombin-catalyzed activation of factor XIII by fibrinogen. Biochemistry. Dec. 20, 1983;22(26):6269-72. doi: 10.1021/bi00295a035. PMID: 6661434.
Plotkin AJ, Wade CE, Jenkins DH, Smith KA, Noe JC, Park MS, Perkins JG, Holcomb JB. A reduction in clot formation rate and strength assessed by thrombelastography is indicative of transfusion requirements in patients with penetrating injuries. J Trauma. Feb. 2008;64(2 Suppl):S64-8. doi: 10.1097/TA.0b013e318160772d. PMID: 18376174.
Weisel JW. The mechanical properties of fibrin for basic scientists and clinicians. Biophys Chem. Dec. 20, 2004;112(2-3):267-76. doi: 10.1016/j.bpc.2004.07.029. PMID: 15572258.
Kuntamukkula MS, McIntire LV, Moake JL, Peterson DM, Thompson WJ. Rheological studies of the contractile force within platelet-fibrin clots: effects of prostaglandin E1, dibutyryl-cAMP and dibutryl-cGMP. Thromb Res. Dec. 1978;13(6):957-69. doi: 10.1016/0049-3848(78)90225-6. PMID: 219559.
Wolberg AS. Plasma and cellular contributions to fibrin network formation, structure and stability. Haemophilia May 2010;16 Suppl 3:7-12. doi: 10.1111/j.1365-2516.2010.02253.x. PMID: 20586795.
Fayed, Nirmeen et al. "Preoperative Thromboelastometry as a Predictor of Transfusion Requirements during Adult Living Donor Liver Transplantation." Transfusion medicine and hemotherapy : offizielles Organ der Deutschen Gesellschaft fur Transfusionsmedizin und Immunhamatologie vol. 42,2 (2015): 99-108. doi:10.1159/000381733.
Hemostasis and Thrombosis: Basic Principles and Clinical Practice Third edition. Edited by Robert W. Colman et al., 1827 pp. 1-25, illustrated. Philadelphia, Lippincott Company, 1994.

Evans PA, Hawkins K, Lawrence M, Williams RL, Barrow MS, Thirumalai N, Williams PR. Rheometry and associated techniques for blood coagulation studies. Med Eng Phys. Jul. 2008;30(6):671-9, doi: 10.1016/j.medengphy.2007.08.005. Epub Sep. 27, 2007. PMID: 17900965.
Weiss, H J et al. "The effect of salicylates on the hemostatic properties of platelets in man." The Journal of clinical investigation vol. 47,9 (1968): 2169-80. doi:10.1172/JCI105903.
Lang, T. & Depka, M.. (2006), Possibilities and limitations of thromboelastometry/thromboelastography. Hamostaseologie. 26. S21-S29. 10.1055/s-0037-1617078.
Lang T, von Depka M. Diagnostische Möglichkeiten und Grenzen der Thrombelastometrie/-graphie [Possibilities and limitations of thrombelastometry/-graphy]. Hamostaseologie. Aug. 2006;26(3 Suppl 1):S20-9. German. PMID: 16953288.
Lang T, von Depka M. Diagnostische Möglichkeiten und Grenzen der Thrombelastometrie/-graphie [Possibilities and limitations of thrombelastometry/-graphy]. Hamostaseologie, Aug. 2006;26(3 Suppl 1);S20-9. English Translation, with Declaration. PMID: 16953288.
Rotem Delta Targeted Therapy Stop the Bleeding. 2013. Exhibit 1027 to IPR2021-00293.
Declaration of Keith B. Neeves, Ph.D, filed on Dec. 14, 2020. Exhibit 1002 to IPR2021-00293.
Keith B. Neeve, Curriculum Vitæ, Sep. 1, 2020, (25 pages). Exhibit 1003 to IPR2021-00293.
Pertinent Materials Reviewed and Considered by Keith Neeves, Ph.D. filed on Dec. 14, 2020 Exhihit 1019 to IPR2021-00293
Definition of "Cavity". Merriam-Webster's Collegiate Dictionary. 2020. Exhibit 1018 to IPR2021-00293.
Final Written Decision filed on Oct. 2, 2019. Exhibit 1011 to IPR2018-00950.
Deposition of Frank Michael LaDuca, Ph.D. on Feb. 13, 2019. Exhibit 1026 to IPR2021-00293.
File History of U.S. Appl. No. 16/146,333, dated Jul. 29, 2020, (156 pages). Exhibit 1013 to IPR2021-00293.
Decision Denying Patent Owner's Request for Rehearing of Final Decision filed on Dec. 5, 2019. Exhibit 1014 to IPR2018-00950.
Hirsh, et al., "How we diagnose and treat deep vein thrombosis," Blood, vol. 99, 2002, pp. 3102-3110.
Beer: Center for Reproductive Immunology & Genetics, "Thrombophilia: Inherited and Acquired," 6 pages, http://repro-med.net/papers/thromb.php. Mar. 30, 2005.
Freedman, et al., "A Meta-Analysis of Thromboembolic Prophylaxis Following Elective Total Hip Arthroplasty," Journal of Bone and Joint Surgery, vol. 82-A, 2000, pp. 929-938.
Hett, et al., "Sonoclot Analysis," British Journal of Anaesthesia, vol. 75, No. 6, Dec. 1995, pp. 771-778. Review. PubMed P.M.I.D.: 8672329.
Hirsh et al., "Oral anticoagulants Mechanism of Action, Clinical Effectiveness, and Optimal Therapeutic Range". Chest. Oct. 1992; 102 (4 Suppl.): 312S-326S. Review. PubMed P.M.I.D.: 1345417.
Euroanaesthesia 2004: Joint Meeting of the European Society of Anaesthesiologists and European Academy of Anaesthesiology Lisbon, Portugal, Jun. 5-8, 2001. (2004). European Journal of Anaesthesiology, 21(S32), 1-221. doi:10.1017/S0265021504000419.
Koepke, J., "Point-of-Care Coagulation Testing," Laboratory Medicine, vol. 31, No. 6, Jun. 2000, pp. 343-346.
Traverso C, Arcelus JI, Gomez E, Luna D, Lopez-Cantarero M, Garcia JM. "Prospective assessment of the risk of deep vein thrombosis in elective abdominal surgery. Predictive role of [Thrombelastograph® analysis]." Thromb Haemorrh Disorders. 1993; 71: 9-15.
Gorlinger et al., "Recommendations for using the ROTEM® in the management of perioperative bleeding in Cardiac Surgery" Recommendations from the ROTEM® Expert Meeting Working Group, Munich 2007, 10 pages.
Peeters et al., "Ultrasonic Measurements of Coagulation and Fibrinolysis". J. Clin. Pathol., May 1964; 17: 320-3. PubMed P.M.I.D.: 14159472; PubMed Central P.M.C.I.D.: PMC480759.
Webster, Medical Instrumentation: Application and Design, New York: John Wiley & Sons, 1998, 6 pages.

(56) References Cited

OTHER PUBLICATIONS

Moake J Overview of Hemostasis. Merck Manuals 2016 http://www.merckmanuals.com/professional/hematology-and-oncology/hemostasis/overview-of-hemostasis.
Lang, T. et al. "Possibilities and limitations of thromboelastometry/thromboelastography" Hamostaseologie 2006: 26 (Suppl 1): S29. (Year: 2006).
Final Office Action received in U.S. Appl. No. 16/201,522, dated Jan. 22, 2021, (20 pages).
Harris, et al., "Evaluation of recurrent thrombosis and hypercoagulability," American Family Physician, vol. 56, No. 6, Oct. 1997, pp. 1591-1596, pp. 1601-1602.
Ickx, Brigitte, "Point-of-Care Monitoring of Haemostasis in the OR and the ICU," European Society of Anaesthesiologists. Jun. 5, 2004, pp. 79-83.
Jensen, Estimation of Blood Velocities Using Ultrasound, 1996, pp. 195-225.
Jolliffe, IT., "Principal Component Analysis," Springer Series in Statistics, 2nd edition, Springer, NY, 2002.
Khurana, Sandeep, et al., "Thromboelastography Can Rapidly Bioassay Fibrinogen," Anesthesiology, vol. 85, No. 3A, Sep. 1996, p. A457.
Freedman, et al., "A Meta-Analysis of Thromboembolic Prophylaxis Following Elective Total Hip Anthroplasty," Journal of Bone and Joint Surgery, vol. 82-A, 2000, pp. 929-938.
Pallister CJ, Watson MS (2010). Haematology. Scion Publishing. pp. 336-347. ISBN 1-904842-39-9.
Petitioner's Reply to Patent Owner's Response of U.S. Pat. No. 9,272,280 dated Mar. 1, 2018, 17 pages.
Petitioner's Reply to Patent Owner's Response of U.S. Pat. No. 9,410,971 dated Mar. 1, 2018, 25 pages.
Amukele, et al., "Comparison of plasma with whole blood prothrombin time and fibrinogen on the same instrument," American Journal of Clinical Pathology, vol. 133, No. 4, Apr. 2010, pp. 550-556.
Anderson, "Multi-Dimensional Velocity Estimation with Ultrasound Using Spatial Quadrature," IEEE Transactions on Ultrasonics Ferroelectrics & Frequency Control, vol. 45, No. 3, 1998, pp. 852-861.
Anderson, "Preventing Deep Vein Thrombosis and Pulmonary Embolism," Center for Outcomes Research, UMass Med Center, 1998, 23 pages.
Becker, R., "Cell-based models of coagulation: a paradigm in evolution," Journal of Thrombosis and Thrombolysis, vol. 20, No. 1, Aug. 2005, pp. 65-68.
Bell, et al., "Thrombelastographic evaluation of coagulation in transurethral prostatectomy," British Journal of Urology, vol. 78, No. 5, 1996, pp. 737-741.
Bercoff et al., "In vivo breast tumor detection using transient elastography," Ultrasound in Medicine & Biology, vol. 29, No. 10, 2003, pp. 1387-1396.
Bercoff, et al., "Supersonic Shear Imaging: A New Technique for Soft Tissue Elasticity Mapping," IEEE Transactions on Ultrasonics Ferroelectrics & Frequency Control, vol. 51 , No. 4, 2004, pp. 396-409.
Bilgen, et al., "Error analysis in acoustic elastography. II. Strain estimation and SNR analysis", Journal of the Acoustical Society of America, vol. 101, 1997, pp. 1147-1154.
Bohs, et al., "A Real Time System for Quantifying and Displaying Two-Dimensional Velocities using Ultrasound," Ultrasound in Medicine & Biology, vol. 19, No. 9, Jul. 1993, pp. 751-761.
Bombeli, et al., "Updates in perioperative coagulation: physiology and management of thromboembolism and haemorrhage" British Journal of Anesthesia; vol. 93, No. 2, Aug. 2004, pp. 275-287.
Bonnefous, et al., "Time Domain Formulation of Pulse—Doppler Ultrasound and Blood Velocity Estimation by Cross Correration," Ultrasonic Imaging 8, 1986, pp. 73-85.
Brock, et al., "Assessing Thrombin Generation at the Point of Care," Clinical Chemistry, vol. 55, No. 3, Mar. 2009, pp. 398-399.
Carr, M., "In vitro assessment of platelet function," Transfusion of Medicine Reviews, vol. 11, No. 2, Apr. 1997, pp. 106-115.
Carroll, et al., "Measurement of functional fibrinogen levels using the Thrombelastograph" Journal of Clinical Anesthesia, vol. 20, No. 3, May 2008, pp. 186-190.
Carter, G., "Coherence and time delay estimation," Proc IEEE, vol. 75, No. 2, 1987, pp. 236-255.
Chandler, et al., "Development of a rapid emergency hemorrhage panel," Tranfusion, vol. 50, No. 12, Dec. 2010, pp. 2547-2552.
Chandler, et al., "Estimating the rate of thrombin and fibrin generation in vivo during cardiopulmonary bypass," Blood, vol. 101, No. 11, Jun. 2003, pp. 4355-4362.
Chaturvedi, et al., "Testing the limitations of 2-D companding for strain imaging using phantoms," IEEE Transactions on Ultrasonics Ferroelectrics & Frequency Control, vol. 45, 1998, pp. 1022-1031.
Chavez, J., "A novel thrombelastograph tissue factor / kaolin assay of activated clotting times for monitoring heparin anticoagulation during cardiopulmonary bypass," Anesthesia and Analgesia; vol. 99, No. 5 Nov. 2004, pp. 1290-1294.
Cohn et al., "An elasticity microscope. Part I: Methods," IEEE Transactions on Ultrasonics Ferroelectrics & Frequency Control, vol. 44, 1997, pp. 1304-1319.
Cohn et al., "An elasticity microscope. Part II: Experimental Results," IEEE Transactions on Ultrasonics Ferroelectrics & Frequency Control, vol. 44, 1997, pp. 1320-1331.
Craft, et al., "A novel modification of the Thrombelastograph assay, isolating platelet function, correlates with optical platelet aggregation," The Journal of Laboratory and Clinical Medicine, vol. 143, No. 5, May 2004, pp. 301-309.
Curry, et al., "Convention and near-patient tests of coagulation," British Journal of Anesthesia, vol. 7, No. 2, Apr. 2007, pp. 45-50.
Dahlback, B., "Blood Coagulation," Lancet, vol. 355, No. 9215, May 2000, pp. 1627-1632.
Despotis, et al., "Monitoring of hemostasis in cardiac surgical patients: impact of point-of-care testing on blood loss and transfusion outcomes," Clinical Chemistry, vol. 43, No. 9, Sep. 1997, pp. 1684-1696.
Embree, et al., "Volumetric Blood Flow via Time-Domain Correlation: Experimental Verification," IEEE Transactions on Ultrasonics Ferroelectrics & Frequency Control, vol. 37, No. 2, May 1990, pp. 176-189.
Emelianov et al., "Ultrasound Elasticity Imaging of Deep Venous Thrombosis," Proc. IEEE Ultrasonics Symp., 2000, pp. 1791-1794.
Fatemi et al., "C-Scan Imaging by Radiation Force Stimulated Acoustic Emission Method," Proc. IEEE Ultrasonics Symp., 1996, pp. 1459-1462.
Deposition of Scott Diamond on Jan. 18, 2018. Exhibit 1063 to IPR2017-00852.
Patent Owner's Request for Oral Argument filed on Apr. 10, 2018 for IPR2017-00852.
Petitioner's Request for Oral Argument filed on Apr. 23, 2018 for IPR2017-00852.
Conduct of the Proceeding filed on Apr. 26, 2018 for IPR2017-00852.
Petitioner's Supplemental Reply in View of Apr. 26, 2018 Institution of Previously Non-Instituted Grounds filed on May 18, 2018 for IPR2017-00852.
Before Jo-Anne M. Kokoski, Kristina M. Kalan, and Jeffrey W. Abraham, Administrative Patent Judges. Transcript from May 4, 2018 Telephone Conference with Patent Trial and Appeal Board. Exhibit 1064 to IPR2017-00852.
Petitioner's Motion to Submit Supplemental Information filed on May 22, 2018 for IPR2017-00852.
Patent Owner's Opposition to Petitioner's Motion to Submit Supplemental Information filed on May 30, 2018 for IPR2017-00852.
Revised Power of Attorney filed on Jun. 1, 2018 for IPR2017-00852.
Order Trial Hearing filed on Jun. 4, 2018 for IPR2017-00852.
Updated Power of Attorney for Patent Owner Hemosonics LLC filed on Jun. 5, 2018 for IPR2017-00852.
Patent Owner's Updated Mandatory Notices filed on Jun. 5, 2018 for IPR2017-00852.
Petitioner's Objections to Patent Owner's Demonstratives filed on Jun. 5, 2018 for IPR2017-00852.

(56) References Cited

OTHER PUBLICATIONS

Petitioner's Updated Mandatory Notices filed on Jun. 8, 2018 for IPR2017-00852.
Decision Granting Patent Owner's Motion to Submit Supplemental Information filed on Jul. 11, 2018 for IPR2017-00852.
Record of Oral Hearing, Jun. 12, 2018 for IPR2017-00852.
Petitioner's Supplemental Request for Oral Argument filed on Aug. 2, 2018 for IPR2017-00852.
Petition for Inter Partes Review of U.S. Pat. No. 9,915,611 filed on Apr. 20, 2018. Exhibit 1065 to IPR2017-00852.
Declaration of Scott L. Diamond, Ph.D in Support of Hemosonics' Petition to Institute an Inter Partes Review of U.S. Pat. No. 9,915,671 filed on May 22, 2018. Exhibit 1066 to IPR2017-00852.
U.S. Pat. No. 9,915,671 Schubert et al. Mar. 13, 2018. Exhibit 1067 to IPR2017-00852.
Ex. 1069 Events Relating to Motion to Submit Supplemental Information filed on May 28, 2018 Exhibit 1069 to IPR2017-00852.
Jeffrey W. Abraham, Jo-Anne Kokoski, and Kristina M. Kalan, Administrative Patent Judges. Hearing Transcript May 22, 2018. Exhibit 1070 to IPR2017-00852.
Patent Owner's Request for Supplemental Oral Hearing filed on Aug. 3, 2018 for IPR2017-00852.
Order Supplemental Trial Hearing filed on Aug. 6, 2018 for IPR2017-00852.
Patent Owner's Objections to Petitioner's Demonstrative Exhibits filed on Aug. 10, 2018 for IPR2017-00852.
Petitioner's Objections to Patent Owner's Demonstratives filed on Aug. 10, 2018 for IPR2017-00852.
Grant of Good Cause Extension filed on Aug. 28, 2016 for IPR2017-00852.
Order Extending One-Year Pendency for Good Cause filed on Aug. 28, 2018 for IPR2017-00852.
Record of Oral Hearing Aug. 14, 2018 for IPR2017-00852.
Final Written Decision Feb. 13, 2019 for IPR2017-00852.
Petition for Inter Partes Review of U.S. Pat. No. 9,272,280 filed on Mar. 6, 2017. Exhibit 2001 to IPR2017-00852.
Declaration of Patrick Mize, Ph.D. filed on Mar. 6, 2011. Exhibit 2002 to IPR2017-00852.
Deposition of Motion for Leave to filed on Jun. 26, 2017. Exhibit 2003 to IPR2017-00852.
Deposition of Patrick D. Mize Oct. 5, 2017. Exhibit 2004 to IPR2017-00852.
Declaration of Dr. Scott Diamond Ph.D. in support of Hemosonics' Response to the Board's Decision to Institute an Inter Partes Review of U.S. Pat. No. 9,272,280 filed on Dec. 1, 2017. Exhibit 2005 to IPR2017-00852.
Curriculum Vitae of Scott Diamond filed on Dec. 1, 2017. Exhibit 2006 to IPR2017-00852.
Pertinent Materials Reviewed and Considered by Scott Diamond, Ph.D. filed on Dec. 1, 2017. Exhibit 2007 to IPR2017-00852.
Colman, R. Hemostasis and Thrombosis, 1994. Exhibit 2008 to IPR2017-00852.
Wolberg, A.S. Plasma and Cellular Contributions to Fibrin Network Formation, Structure, Stability, Haemophilia 2010. Exhibit 2009 to IPR2017-00852.
Janas, T. et al. Promotion and Thrombin-Catalyzed Activation of Factor XIII by Fibrinogen. Biochemistry 1983, 22, 6269-6272. Exhibit 2010 to IPR2017-00852.
Niewiarowski, S. et al. ADP, thrombin and Bothrops atrox thrombin-like enzyme in platelet-dependent fibrin retraction. vol. 229, No. 3, 1975. Exhibit 2011 to IPR2017-00852.
Janmey, P. Kinetics of Fibrin Oligomer Formation Observed by Electron Microscopy. Biochemistry, 1983. Exhibit 2012 to IPR2017-00852.
Cuisset, T. et al. Clopidogrel response: Head-to-head comparison of different platelet assays to identify clopidogrel non responder patients after coronary stenting. 2009. Exhibit 2013 to IPR2017-00852.
Multiple Analyzer: Powerful Analysis of Platelet Function. Roche Diagnostics International Ltd. 2013. Exhibit 2014 to IPR2017-00852.

Verify Now System . Accriva Diagnostics. VerifyNow Reference Guide. 2014. Exhibit 2015 to IPR2017-00852.
Kuntamukkula, M.S. et al. Rheological Studies of the Contractile Force Within Platelet-Fibrin Clots: Effects of Prostglandin E1, Dibutyryl-cAMP and Dibutyryl-cGMP. 1978. Exhibit 2016 to IPR2017-00852.
Plotkin, A. et al. A Reduction in Clot Formation Rate and Strength Assessed by Thrombelastography is Indicative of Transfusion Requirements in Patients with Penetrating Injuries. The Journal of Trauma Injury, Infection, and Critical Care 2008. Exhibit 2017 to IPR2017-00852.
Evans, P.A. et al. Rheometry and associated techniques for blood coagulation studies. Medical Engineering & Physics 30 (2008) 671-679. Exhibit 2018 to IPR2017-00852.
Petitioner's Power of Attorney filed on Feb. 4, 2017 for IPR2017-00855.
Petition for Inter Partes Review filed on Feb. 4, 2017 for IPR2017-00855.
Patent Owner's Mandatory Notices filed on Feb. 23, 2017 for IPR2017-00855.
Power of Attorney for Patent Owner Hemosonics LLC filed on Feb. 22, 2017 for IPR2017-00855.
Notice of Filing Date Accorded to Petition and Time for Filing Patent Owner Preliminary Response filed on Mar. 9, 2017 for IPR2017-00855.
Order Conduct of the Proceeding filed on Mar. 5, 2017 for IPR2017-00855.
Response to Notice of Filing for Inter Partes Review of U.S. Pat. No. 9,410,971 filed on May 5, 2017 for IPR2017-00855.
Patent Owner's Preliminary Response filed on Jun. 7, 2017 for IPR2017-00855.
Patent Owner's Updated Mandatory Notices filed on Jun. 8, 2017 for IPR2017-00855.
Patent Owner's Updated Mandatory Notices filed on Jun. 22, 2017 for IPR2017-00855.
Power of Attorney for Patent Owner's Hemosonics LLC filed on Jun. 20, 2017 for IPR2017-00855.
Patent Owner's Updated Exhibit List filed on Jun. 30, 2017 for IPR2017-00855.
Order Conduct of the Proceeding filed Jul. 10, 2011 for IPR2017-00855.
Decision Institution Inter Partes Review filed Sep. 1, 2017 for IPR2017-00855.
Scheduling Order filed on Sep. 1, 2017 for IPR2017-00855.
Petitioner's Request for Rehearing filed on Sep. 15, 2017 for IPR2017-00855.
Patent Owner's Objection to Evidence filed on Sep. 18, 2017 for IPR2017-00855.
Patent Owner's Notice of Deposition of Patrick D. Mize filed on Sep. 26, 2017 for IPR2017-00855.
Decision Denying Petitioner's Request for Rehearing filed on Nov. 3, 2017 for IPR2017-00855.
Patent Owner's Response to the Decision to Institute Inter Partes Review of U.S Pat. No. 9,410,971 filed on Dec. 1, 2017 for IPR2017-00855.
Patent Owner's Updated Exhibit List filed on Dec. 1, 2017 for IPR2017-00855.
Petitioner's Notice of Deposition of Dr. Scott Diamond filed on Jan. 9, 2018 for IPR2017-00855.
Petitioner's Reply to Patent Owner's Response filed on Mar. 1, 2018 for IPR2017-00855.
Petitioner's Updated Exhibit List filed on Mar. 1, 2018 for IPR2017-00855.
Patent Owner's Request for Oral Argument filed on Apr. 10, 2018 for IPR2017-00855.
Petitioner's Request for Oral Argument filed on Apr. 23, 2018 for IPR2017-00855.
Conduct of the Proceeding filed on Apr. 28, 2018 for for IPR2017-00855.
Petitioner's Supplemental Reply in View of Apr. 26, 2018 Institution of Previously Non-Instituted Grounds filed on filed on May 18, 2018 for IPR2017-00855.

(56) References Cited

OTHER PUBLICATIONS

Petitioner's Motion to Submit Supplemental Information filed May 22, 2018 for IPR2017-00855.
Order Conduct of the Proceeding filed on May 24, 2018 for IPR2017-00855.
Patent Owner's Opposition to Petitioner's Motion to Submit Supplemental Information filed on May 30, 2018 for IPR2017-00855.
Revised Power of Attorney filed on Jun. 1, 2018 for IPR2017-00855.
Petitioner's Motion to Withdraw Grounds filed on Jun. 1, 2018 for IPR2017-00855.
Order Trial Hearing filed on Jun. 4, 2018 for IPR2017-00855.
Updated Power of Attorney for Patent Owner Hemosonics LLC filed on Jun. 5, 2018 for IPR2017-00855.
Patent Owner's Updated Mandatory Notice filed on Jun. 5, 2018 for IPR2017-00855.
Patent Owner's Opposition to Petitioner's Motion to Withdraw Obviousness Grounds filed on Jun. 8, 2018 for IPR2017-00855.
Petitioner's Objections to Patent Owner's Demonstratives filed on Jun. 8, 2018 for IPR2017-00855.
Petitioner's Updated Mandatory Notices filed on Jun. 8, 2018 for IPR2017-00855.
Petitioner's Reply to Patent Owner's Opposition to Petitioner's Motion to Withdraw Grounds filed on Jun. 15, 2018 for IPR2017-00855.
Decision Denying Petitioner's Motion to Withdraw Grounds filed on Jul. 11, 2018 for IPR2017-00855.
Decision Granting Patent Owner's Motion to Submit Supplemental Information filed on Jul. 11, 2018 for IPR2017-00855.
Record of Oral Hearing Jun. 12, 2018 for IPR2017-00855.
Petitioner's Supplemental Request for Oral Argument filed on Aug. 2, 2018 for IPR2017-00855.
Patent Owner's Request for Supplemental Oral Hearing filed on Aug. 3, 2018 for IPR2017-00855.
Order Supplemental Trial Hearing filed on Aug. 6, 2018 for IPR2017-00855.
Patent Owner's Objections to Petitioner's Demonstratives Exhibits filed on Aug. 10, 2018 for IPR2017-00855.
Petition's Objections to Patent Owner's Demonstratives filed on Aug. 10, 2018 for IPR2017-00855.
Grant of Good Cause Extension filed on Aug. 28, 2018 for IPR2017-00855.
Order Extending One-Year Pendency for Good Cause filed on Aug. 28, 2018 for IPR2017-00855.
Record of Oral Hearing filed on Aug. 14, 2018 for IPR2017-00855.
Final Written Decision filed on Feb. 13, 2019 for IPR2017-00855.
U.S. Pat. No. 9,272,280 Viola et al. Mar. 1, 2016. Exhibit 1001 to IPR2017-00855.
U.S. Pat. No. 9,410,971 Viola et al. Aug. 9, 2016. Exhibit 1002 to IPR2017-00855.
Declaration of Patrick Mize, Ph.D. filed Feb. 4, 2017. Exhibit 1003 to IPR2017-00855.
Patrick Mize, Ph.D. Curriculum Vitae filed on Feb. 4, 2017. Exhibit 1004 to IPR2017-00855.
U.S. Pat. No. 6,221,672 Braugh et al. Apr. 24, 2001. Exhibit 1005 to IPR2017-00855.
U.S. Patent Publication No. 2010/0154520 Schubert et al. Jun. 24, 2010. Exhibit 1006 to IPR2017-00855.
U.S. Pat. No. 6,016,712 Warden et al. Jan. 25, 2000. Exhibit 1007 to IPR2017-00855.
Lang, T. et al., Different effects of abciximab and cytochalasin D on clot strength in thrombelastography. 2003. Exhibit 1008 IPR2017-00855.
Issue Notification for U.S. Pat. No. 9,272,280, filed on Feb. 3, 2017. Exhibit 1009 to IPR2017-00855.
Exhibit 1010: Table of Prior Art Devices filed on Feb. 4, 2017. Exhibit 1010 to IPR2017-00855.
U.S. Patent Publication No. 2003/0113929 Baugh et al. Jun. 19, 2003. Exhibit 1011 to IPR2017-00855.

Viola, F. et al. A novel ultraound-based method to evaluate hemostatic function of whole blood. Clinica Chimica Acta 411, 2010: 106-113. Exhibit 1012 to IPR2017-00855.
U.S. Pat. No. 5,504,011 Gavin et al. Apr. 2, 1996. Exhibit 1013 to IPR2017-00855.
U.S. Pat. No. 6,613,286 Braun, Sr. et al. Sep. 2, 2009. Exhibit 1014 to IPR2017-00855.
U.S. Pat. No. 5,888,826 Ostgaard et al. Mar. 30, 1999. Exhibit 1015 to IPR2017-00855.
U.S. Pat. No. 6,046,051 Jina et al. Apr. 4, 2000. Exhibit 1016 to IPR2017-00855.
U.S. Patent Publicaiton No. 2003/0199082 Miller et al. Oct. 23, 2004. Exhibit 1017 to IPR2017-00855.
U.S. Patent Publication No. 2005/0015001 Lee et al. Jan. 20, 2005. Exhibrt 1018 to IPR2017-00855.
Gottumukkala, V. et al. Assesing Platelet and Fibrinogen Contribution to Clot Strength Using Modified Thromboelastography in Pregnant Women. Anesth Analg 1999. Exhibit 1019 to IPR2017-00855.
Corrected Citations for the Petition filed on Jul. 27, 2017. Exhibit 1020 to IPR2017-00855.
Deposition of Scott L. Diamond on Jan. 18, 2018. Exhibit 1068 to IPR2017-00855.
Before Jo-Anne M. Kokoski, Kristina M. Kalana, and Jeffrey W. Abraham, Administrative Patent Judges. Transcript from May 4, 2018 Telephone Conference with Patent Trial and Appeal Board. Exhibit 1069 to IPR2017-00855.
Petition for Inter Partes Review of U.S. Pat. No. 9,915,671 filed on Apr. 20, 2018. Exhibit 1070 to IPR2017-00855.
Declaration of Scott L. Diamond, Ph.D. in Support of Hemsonics' Petition to Institute an Inter Partes Review of U.S. Pat. No. 9,915,671 filed on Apr. 20, 2018. Exhibit 1071 to IPR2017-00855.
U.S. Pat. No. 9,915,671 Schubert et al. Mar. 13, 2018. Exhibit 1072 to IPR2017-00855.
Exhibit 1074 Events Relating to Motion to Submit Supplemental Information filed on May 22, 2018. Exhibit 1074 to IPR2017-00855.
Before Jeffrey W. Abraham, Jo-Anne M. Kokoski, and Kristina M. Kalana, Administrative Patent Judges. Hearing Transcript May 22, 2018 Exhibit 1075 to IPR2017-00855.
America's Best-Selling Dictionary. Merriam-Webster's Collegiate Dictionary. Eleventh Addition. 2014. Exhibit 2001 to IPR2017-00855.
Petition for Inter Partes Review of U.S. Pat. No. 9,410,971 filed on Jun. 7, 2017. Exhibit 2002 to IPR2017-00855.
Declaration of Patrick Mize, Ph.D. filed on Jun. 7, 2017. Exhibit 2003 to IPR2017-00855.
Deposition of Motion for Leave to File Jun. 26, 2017. Exhibit 2004 to IPR2017-00855.
Deposition of Patrick D. Mize, Oct. 5, 2017. Exhibit 2005 to IPR2017-00855.
Declaration of Dr. Scott Diamond, Ph.D., in Support of Hemosonics' Response to the Board's Decision to Institute an Inter Partes Review of U.S. Pat. No. 9,410,971 filed on Dec. 1, 2017. Exhibit 2006 to IPR2017-00855.
Curriculum Vitae Scott L. Diamond filed on Dec. 1, 2017. Exhibit 2007 to IPR2017-00855.
Pertinent Materials Reviewed and Considered by Scott Diamond, Ph.D. filed on Dec. 1, 2017. Exhibit 2008 to IPR2017-00855.
Colman R. et al. Hemostasis and Thrombosis,1994. Exhibit 2009 to IPR2017-00855.
Wolberg, A.S. Plasma and cellular contributions to fibrin network formation, structure and stability. Department of Pathology and Laboratory Medicine, University of North Carolina at Chapel Hill, NC. Haemophilia 2010. Exhibit 2010 to IPR2017-00855.
Janus, T. et al. Promotion and Thrombin-Catalyzed Activation of Factor XIII by Fibrinogen. Biochemistry 1983, 22, 6269-6272 Exhibit 2011 for IPR2017-00855.
Niewiarowski, S. et al. ADP, thrombin, and Bothrops atrox thrombin-like enzyme in platelet-dependent fibrin retraction. vol. 229, No. 3, 1975. Exhibit 2012 to IPR2017-00855.

(56) References Cited

OTHER PUBLICATIONS

Janmey, P. Kinetics of Fibrin Oligomer Formation Observed by Electron Microscopy. Biochemistry, 1983. Exhibit 2013 to IPR2017-00855.
Blattler, W. et al. Effect of In Vivo Produced Fibrinogen-Fibrin Intermediates on Viscosity of Human Blood. vol. 4, 787-801, 1974. Exhibit 2014 to IPR2017-00855.
Weisel, J. The mechanical properties of fibrin for basic scientists and clinicians. Biophysical Chemistry 112 (2004). Exhibit 2015 to IPR2017-00855.
Cuisset, T. et al. Clopidogrel response: Head-to-head comparison of different platelet assays to identify clopidogrel non responder patients after coronary stenting. 2009. Exhibit 2016 to IPR2017-00855.
Multiple Analyzer: Powerful Analysis of Platelet Function. Roche Diagnostics International Ltd. 2013. Exhibit 2017 to IPR2017-00855.
Verify Now System . Accriva Diagnostics. VerityNow Reference Guide. 2014. Exhibit 2018 to IPR2017-00855.
Evans, P.A. et al. Rheometry and associated techniques for blood coagralation studies. Medical Engineering & Physics 30 (2008) 671-679. Exhibit 2019 to IPR2017-00855.
Kuntamukkola, M.S. et al. Rheological Studies of the Contractile Force Within Platelet-Fibrin Clots: Effects of Prostglandin E1, Dibutyryl-cAMP and Dibutyryl-cGMP. 1978. Exhibit 2020 to IPR2017-00855.
Plotkin, A. et al. A Reduction in Clot Formation Rate and Strength Assessed by Thrombelastography is Indicative of Transfusion Requirements in Patients with Penetrating Injuries. The Journal of Trauma Injury, Infection, and Critical Care 2008. Exhibit 2021 to IPR2017-00855.
Ozkaya, N. et al. Fundamentals of Biomechanics Equilibrium, Motion and Deformation, 2nd Edition. 1999. Exhibit 2022 to IPR2017-00855.
Liptak, B. Process Measurement and Analysis vol. 1. Instrument Engineers' Handbook, Fourth Edition. 2003. Exhibit 2023 to IPR2017-00855.
Thurston, G.B. Viscoelasticity of Human Blood. Biophysical Journal, vol. 12. 1972. Exhibit to IPR2017-00855.
Ozkaya, N. et al. Fundamentals of Biomechanics Equilibrium, Motion and Deformation, 3rd Edition 2012. Exhibit 2025 to IPR2017-00855.
Stony Brook Portable Field Viscometer for a Quick 'Pass' or 'Fail' decision filed on Dec. 1, 2017. Exhibit 2026 Ozkaya, N. et al. Fundamentals of Biomechanics Equilibrium, Motion and Deformation, 2nd Edition.1999. Exhibit 2026 to IPR2017-00855.
Petition for Inter Partes Review of U.S. Pat. No. 9,410,971 filed on Nov. 30, 2017 for IPR2018-00264.
Petitioner's Power of Attorney filed on Nov. 30, 2011 for IPR2018-00264.
Notice of Filing Date Accorded to Petition and Time for Filing Patent Owner Preliminary Response filed on Dec. 12, 2017 for IPR2018-00264.
Power of Attorney for Patent Owner Hemosonics LLC filed on Dec. 13, 2017 for IPR2018-00264.
Patent Owner's Mandatory Notices filed on Dec. 13, 2017 for IPR2018-00264.
Patent Owner's Preliminary Response to Petition Requesting Inter Partes Review of U.S. Pat. No. 9,410,971 filed on Feb. 14, 2018 for IPR2018-00264.
Order Conduct of the Proceeding filed on Mar. 9, 2018 for IPR2018-00264.
Decision Denying Institution of Inter Partes Review filed on May 10, 2018 for IPR2018-00264.
Petition's Request for Refund filed on May 26, 2018 for IPR2018-00264.
Notice of Refund filed on Jun. 4, 2018 for IPR2018-00264.
U.S. Pat. No. 9,272,280 Viola et al. Mar. 1, 2016. Exhibit 1001 to IPR2018-00264.
U.S. Pat. No. 9,410,971 Viola et al. Aug. 9, 2016. Exhibit 1002 to IPR2018-00264.
Declaration of Patrick Mize, Ph.D. filed on Nov. 30, 2017. Exhibit 1003 to IPR2018-00264.
Patrick D. Mize Ph.D. Curriculum Vitae filed on Nov. 30, 2017. Exhibit 1004 to IPR2018-00264.
U.S. Pat. No. 6,221,672 Baugh et al. Apr. 24, 2001. Exhibit 1005 to IPR2018-00264.
U.S. Patent Publication No. 2010/0154520 Schubert et al. Jun. 24, 2010. Exhibit 1006 to IPR2018-00264.
U.S. Pat. No. 6,016,712 Warden et al. Jan. 25, 2000. Exhibit 1007 to IPR2018-00264.
Lang, T. et al. Different effects of abciximab and cytochalasin D on clot strength in thrombelastography. 2003. Exhibit 1008 IPR2018-00264.
Issue Notification for U.S. Pat. No. 9,272,280, filed on Nov. 30, 2017. Exhibit 1009 to IPR2018-00264.
Exhibit 1010: Table of Prior Art Devices filed on Nov. 30, 2017. Exhibit 1010 to IPR2018-00264.
U.S. Patent Publication No. 2003/0113929 Baugh et al. Jun. 19, 2003. Exhibit 1011 to IPR2018-00264.
Viola, F. et al. A novel ultraound-based method to evaluate hemostatic function of whole blood. Clinica Chimica Acta 411, 2010: 106-113. Exhibit 1012 to IPR2018-00264.
U.S. Pat. No. 5,504,011 Gavin et al. Apr. 2, 1996. Exhibit 1013 to IPR2018-00264.
U.S. Pat. No. 6,613,286 Baugh, Sr. et al. Sep. 2, 2009. Exhibit 1014 to IPR2018-00264.
U.S. Pat. No. 5,888,862 Ostgaard et al. Mar. 30, 1999. Exhibit 1015 to IPR2018-00264.
U.S. Pat. No. 6,046,051 Jina et al. Apr. 4, 2000. Exhibit 1016 to IPR2018-00264.
U.S. Patent Publication No. 2003/0199082 Miller et al. Oct. 23, 2004. Exhibit 1017 to IPR2018-00264.
U.S. Patent Publication No. 2005/0015001 Lee et al. Jan. 20, 2005. Exhibit 1018 IPR2018-00264.
Gottumukkala, V. et al. Assesing Platelet and Fibrinogen Conhibution to Clot Strength Using Modified Thromboelastography in Pregnant Women. Anesth Analg 1999. Exhibit 1019 to IPR2018-00264.
Gorlinger, K. et al. Perioperative Coagulation Management and Control of Platelet Transfusion by Point-of-Care Platelet Function Analysis. Transfusion Medicine and Hemotherapy 2007. Exhibit 1020 to IPR2018-00264.
Rahe-Meyer, N. et al. Multicentric comparison of single portion reagents and liquid reagents for thromboelastometry, 2009. Exhibit 1021 to IPR2018-00264.
U.S. Patent Publication No. 2004/0072357 Stiene et al. Apr. 15, 2004. Exhibit 1022 to IPR2018-00264.
U.S. Pat. No. 6,318,191 Chen Nov. 20, 2001. Exhibit 1023 to IPR2018-00264.
Tonal, B.G. et al. Comparison of procoagulatory markers in function of anesthetic/analgesic technique used on the surgery of traumathology prosthesis replacement. Transfusion and haemostasis. 1981. Exhibit 1024 to IPR2018-00264.
Douning, L. et al. Hypothermic Patients. Temperature Corrected Thrombelastography in Hypothermic Patients. Anesth Anal 1995. Exhibit 1025 to IPR2018-00264.
Faulds, D. et al. Abciximab (c7E3Fab). A review of its pharmacology and therapeutic potential in ischaemic heart disease, 1994. Exhibit 1026 to IPR2018-00264.
Decision Denying Institution of Post-Grant Review filed on Aug. 23, 2019 for PRG2019-00033.
Request for Rehearing and Request to Enter New Exhibits filed on Sep. 22, 2019 for PRG2019-00033.
Decision Denying Petitioner's Request for Rehearing filed on Nov. 8, 2019 for PRG2019-00033.
Gabriel Goldman Email to the Patent Trial and Appeal Boardon Jun. 3, 2019. Exhibit 1014 to PRG2019-00033.
Email from Trials@USPTO.gov to Gabriel Goldman on Jun. 5, 2019. Exhibit 1015 to PRG2019-00033.
Record of Oral Hearing on Jul. 9, 2019 for IPR2018-00950.
Judgment Final Written Decision Determining all Challenged Claims Unpatentable for IPR2018-00950 filed on Oct. 2, 2019.
Request for Rehearing filed on Nov. 1, 2019 for IPR2018-00950.

(56) References Cited

OTHER PUBLICATIONS

Decision Denying Patent Owner's Request for Rehearing of Final Decision filed on Dec. 5, 2019 for IPR2018-00950.
Patent Owner's Notice of Appeal filed on Feb. 4, 2020 for IPR2018-00950.
Order Granting Request for Ex Parte Reexamination of U.S. Pat. No. 11,061,038, issued Dec. 10, 2021, 15 pages.
Paper 10, Scheduling Order for IPR2021-00293 of U.S. Pat. No. 10,746,750, issued Jul. 11, 2021, 11 pages.
Paper 9, Decision Granting Institution of Inter Partes Review under 35 U.S.C. § 314 for IPR2021-00293 of U.S. Pat. No. 10,746,750, issued Jul. 1, 2021, 29 pages.
Patent Owner's Response to Petition under 37 C.F.R. §42.120 for IPR2021-00293 of U.S. Pat. No. 10,746,750, filed Sep. 24, 2021, 24 pages.
Patent Owner's Preliminary Response for IPR2021-00293 of U.S. Pat. No. 10,746,750, filed Apr. 22, 2021, 6 pages.
Petitioner's Reply to Patent Owner's Response under 37 C.F.R. §42.120 for IPR2021-00293 of U.S. Pat. No. 10,746,750, filed Dec. 16, 2021, 30 pages.
Exhibit 1004. Response to Non-Final Office Action for IPR2021-00293 of U.S. Appl. No. 16/146,333, filed Dec. 19, 2019, 10 pages.
Exhibit 2001. Statutory Terminal Disclaimer for IPR2021-00293 of U.S. Pat. No. 10,746,750, filed Apr. 22, 2021, 3 pages.
Exhibit 1031, Paper 21, Patent Owner's Sur-Reply for IPR2018-00950 of U.S. Pat. No. 9,915,671, filed May 6, 2019, 34 pages.
Exhibit 1030, Paper 19, Petitioner's Reply to Patent Owner's Response for IPR2018-00950 of U.S. Pat. No. 9,915,671, filed Apr. 4, 2019, 32 pages.
Exhibit 2003, Definition of "Duct" retrieved from Dictionary.com., for IPR2021-00293 of U.S. Pat. No. 10,746,750, filed Apr. 22, 2021, 8 pages.
Exhibit 1032, Request for Rehearing for IPR2018-00950 of U.S. Pat. No. 9,915,671, filed Nov. 1, 2019, 15 pages.
Exhibit 1029, Patent Owner's Response for IPR2018-00950 of U.S. Pat. No. 9,915,671, filed Jan. 4, 2019, 37 pages.
Request for Ex Parte Reexamination of U.S. Pat. No. 11,061,038 Filed by a Third Party Requester Nov. 3, 2021, 341 pages.
Appendix A of Request for Ex Parte Reexamination of U.S. Pat. No. 11,061,038 filed by a Third Party Requester, Nov. 3, 2021, 102 pages.
Appendix B of Request for Ex Parte Reexamination of U.S. Pat. No. 11,061,038 filed by a Third Party Requester, Nov. 3, 2021, 112 pages.
Appendix C of Request for Ex Parte Reexamination of U.S. Pat. No. 11,061,038 filed by a Third Party Requester, Nov. 3, 2021, 126 pages.
Appendix D of Request for Ex Parte Reexamination of U.S. Pat. No. 11,061,038 filed by a Third Party Requester, Nov. 3, 2021, 139 pages.
Exhibit 1001. U.S. Pat. No. 11,061,038, issued Jul. 13, 2021, of Request for Ex Parte Reexamination filed by a Third Party Requester, Nov. 3, 2021, 39 pages.
Exhibit 1002. File History of U.S. Pat. No. 11,061,038, issued Jul. 13, 2021, of Request for Ex Parte Reexamination filed by a Third Party Requester, Nov. 3, 2021, 417 pages.
Exhibit 1003. PTAB-IPR2018-00950 Declaration of Scott L. Diamond, of Request for Ex Parte Reexamination filed by a Third Party Requester, Nov. 3, 2021, 201 pages.
Exhibit 1004. U.S. Pat. No. 5,629,209, issued May 13, 1977, of Request for Ex Parte Reexamination filed by a Third Party Requester, Nov. 3, 2021, 39 pages.
Exhibit 1005. PTAB-IPR2018-00950 Lang 2006 (German), of Request for Ex Parte Reexamination filed by a Third Party Requester, Nov. 3, 2021, 14 pages.
Exhibit 1006. PTAB-IPR2018-00950 Lang 2006 (certified English translation), of Request for Ex Parte Reexamination filed by a Third Party Requester, Nov. 3, 2021, 28 pages.
Exhibit 1007. PTAB-IPR2018-00950 Lang 2006 (Supplemental English translation), of Request for Ex Parte Reexamination filed by a Third Party Requester, Nov. 3, 2021, 10 pages.
Exhibit 1008. IPR2021-00293 Statutory Disclaimer, of Request for Ex Parte Reexamination filed by a Third Party Requester, Nov. 3, 2021, 4 pages.
Exhibit 1009. U.S. Pat. No. 6,016,712, issued Jan. 25, 2000, of Request for Ex Parte Reexamination filed by a Third Party Requester, Nov. 3, 2021, 24 pages.
Exhibit 1010. U.S. Pat. No. 9,915,671, issued May 13, 2018, of Request for Ex Parte Reexamination filed by a Third Party Requester, Nov. 3, 2021, 25 pages.
Exhibit 1011. IPR2018-00950 Final Written Decision (Paper 30), of Request for Ex Parte Reexamination filed by a Third Party Requester, Nov. 3, 2021, 50 pages.
Exhibit 1012. IPR2021-00293 Petition for IPR of U.S. Pat. No. 10,746,750 (Paper 2), of Request for Ex Parte Reexamination filed by a Third Party Requester, Nov. 3, 2021, 80 pages.
Exhibit 1013. IPR2021-00293 Trial instituted Decision (Paper 9), of Request for Ex Parte Reexamination filed by a Third-Party Requester, Nov. 3, 2021, 30 pages.
Exhibit 1014. IPR2018-00950 Petition for IPR of U.S. Pat. No. 9,915,671 (Paper 2), of Request for Ex Parte Reexamination filed by a Third-Party Requester, Nov. 3, 2021, 77 pages.
Exhibit 1015. IPR2018-00950 Patent Owner's Response (Paper 13), of Request for Ex Parte Reexamination filed by a Third-Party Requester, Nov. 3, 2021, 38 pages.
Exhibit 1016. IPR2018-00950 General Order (Paper 34), of Request for Ex Parte Reexamination filed by a Third-Party Requester, Nov. 3, 2021, 7 pages.
Exhibit 1017. IPR2021-00293 Patent Owner's Response (Paper 11), of Request for Ex Parte Reexamination filed by a Third-Party Requester, Nov. 3, 2021, 25 pages.
Exhibit 1018. Dictionary.com online dictionary—cavity; ductwork; duct, of Request for Ex Parte Reexamination filed by a Third-Party Requester, Nov. 3, 2021, 22 pages.
Exhibit 1019. IPR2018-00950 Petitioner's Reply to Patent Owner's Response (Paper 19), of Request for Ex Parte Reexamination filed by a Third-Party Requester, Nov. 3, 2021, 33 pages.
Exhibit 1020. U.S. Patent Publication No. 2005220668A1, published Oct. 6, 2005, of Request for Ex Parte Reexamination filed by a Third Party Requester, Nov. 3, 2021, 18 pages.
Exhibit 1021. U.S. Pat. No. 6,613,286, issued Sep. 2, 2003, of Request for Ex Parte Reexamination filed by a Third Party Requester, Nov. 3, 2021, 20 pages.
Exhibit 1022. U.S. Patent Publication No. 20040189311A1, published Sep. 30, 2004, of Request for Ex Parte Reexamination filed by a Third Party Requester, Nov. 3, 2021, 91 pages.
Exhibit 1023. U.S. Patent Publication No. 20050233460A1, published Oct. 20, 2005, of Request for Ex Parte Reexamination filed by a Third Party Requester, Nov. 3, 2021, 32 pages.
Exhibit 1024. Straub et al., of Request for Ex Parte Reexamination filed by a Third Party Requester, Nov. 3, 2021, 8 pages.
Transmittal of Request for Ex Parte Reexamination of U.S. Pat. No. 11,061,038 Filed by a Third Party Requester Nov. 3, 2021, 3 pages.
Electronic Acknowledgment Receipt of Request for Ex Parte Reexamination of U.S. Pat. No. 11,061,038 Filed by a Third Party Requester Nov. 3, 2021, 7 pages.
Information Disclosure Statement accompanying Request for Ex Parte Reexamination of U.S. Pat. No. 11,061,038 Filed by a Third Party Requester Nov. 3, 2021, 2 pages.
Communication under Article 94(3) EPC for European patent application No. 20175351.4, dated Feb. 15, 2022, with English Summary, (4 pages).

* cited by examiner

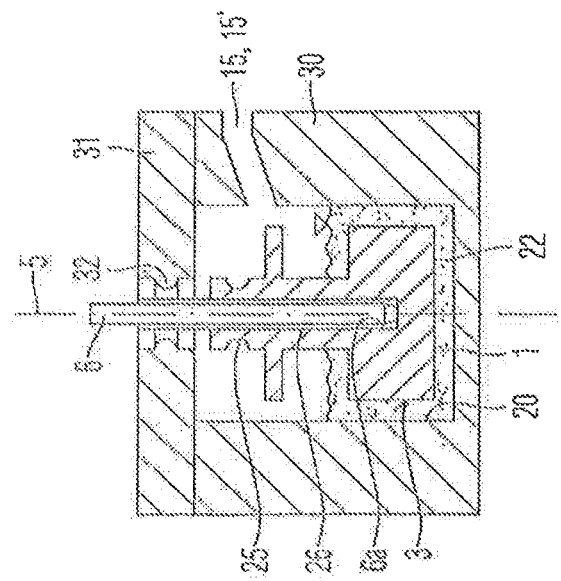
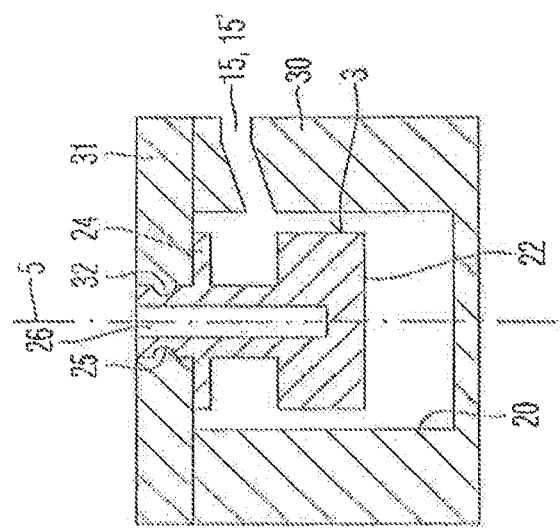
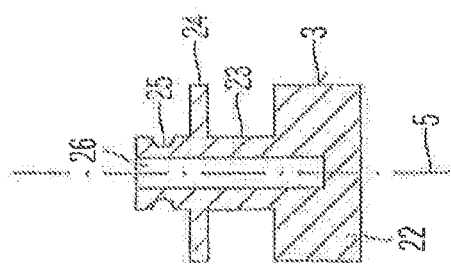

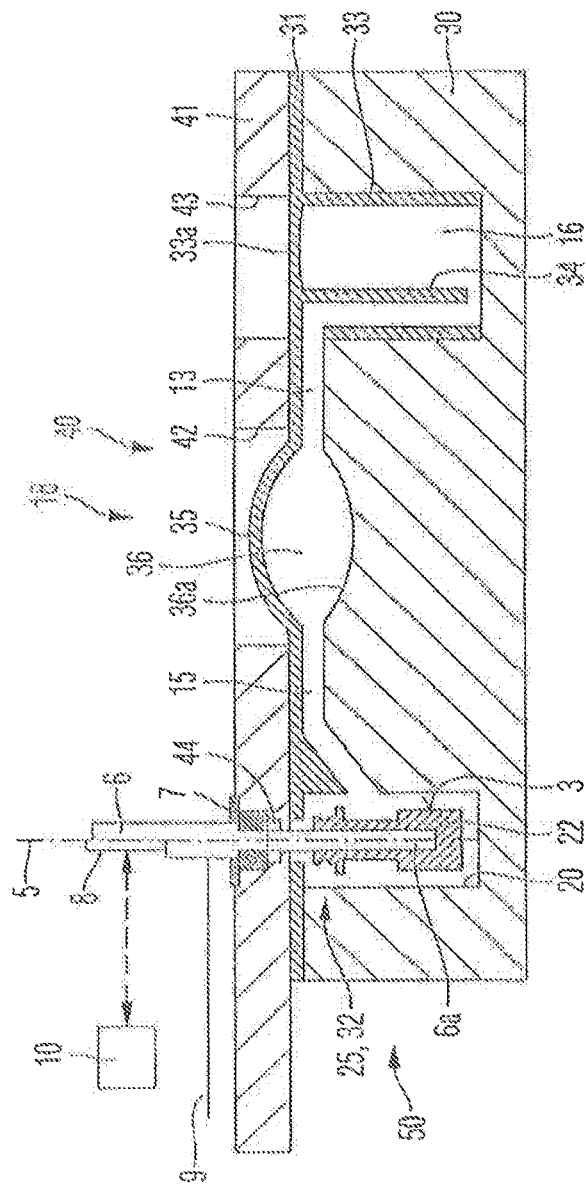

CARTRIDGE DEVICE FOR A MEASURING SYSTEM FOR MEASURING VISCOELASTIC CHARACTERISTICS OF A SAMPLE LIQUID, A CORRESPONDING MEASURING SYSTEM, AND A CORRESPONDING METHOD

CROSS REFERENCE TO RELATED APPLICATIONS

This application is a continuation application and claims the benefit of U.S. application Ser. No. 17/182,502 filed on Feb. 23, 2021 and to issue as U.S. Pat. No. 11,061,038 on Jul. 13, 2020, which is a continuation of and claims the benefit of U.S. patent application Ser. No. 16/520,004 filed Jul. 23, 2019, now U.S. Pat. No. 10,996,230 issued on May 4, 2021, which is a continuation of and claims the benefit of U.S. application Ser. No. 16/146,333, filed Sep. 28, 2018, now U.S. Pat. No. 10,746,750, which is a continuation of and claims the benefit U.S. application Ser. No. 15/869,782, filed Jan. 12, 2018, which is a continuation of and claims the benefit of U.S. application Ser. No. 15/357,492, filed Nov. 21, 2016, now U.S. Pat. No. 9,915,671, issued on Mar. 13, 2018, which is a continuation of and claims the benefit of U.S. application Ser. No. 15/066,605, filed Mar. 10, 2016, now U.S. Pat. No. 9,739,789, issued on Aug. 22, 2017, which is a continuation of and claims the benefit of U.S. application Ser. No. 13/895,034, filed on May 15, 2013, now U.S. Pat. No. 9,285,377, issued on Mar. 15, 2016, which is a continuation of and claims the benefit of U.S. application Ser. No. 12/640,376, filed on Dec. 17, 2009, now U.S. Pat. No. 8,448,499 issued on May 28, 2013, which claims priority to and the benefit of U.S. Provisional Application No. 61/140,344 filed on Dec. 23, 2008. This application is related to U.S. application Ser. No. 16/520,006 filed Jul. 23, 2019, U.S. application Ser. No. 13/895,053 filed on May 15, 2013, now U.S. Pat. No. 9,086,423, issued on Jul. 21, 2015, to U.S. application Ser. No. 13/895,002, filed on May 15, 2013, now U.S. Pat. No. 8,857,244 issued on Oct. 14, 2014, and to U.S. application Ser. No. 13/894,998, filed on May 15, 2013, now U.S. Pat. No. 9,110,084 issued on Aug. 18, 2015, which are continuation applications of and claim the benefit of U.S. application Ser. No. 12/640,376, filed on Dec. 17, 2009, now U.S. Pat. No. 8,448,499 issued on May 28, 2013, which claims priority to and the benefit of U.S. Provisional Application No. 61/140,344 filed on Dec. 23, 2008. The entire contents of each of the above patents and applications are incorporated herein in their entirety by reference for all purposes.

FIELD OF THE INVENTION

The present invention relates to a cartridge device for a measuring system for measuring viscoelastic characteristics of a sample liquid, in particular of a blood sample liquid. The present invention also relates to a corresponding measuring system and method.

It is essential for survival that a wound stops bleeding, i.e. that the body possesses an adequate mechanism for haemostasis. The process of blood clotting can be activated in the case of injuries or inflammations by either extrinsic or intrinsic factors, e.g. tissue factor (TF) or Hagemann factor (F XII), respectively. Both activation channels are continued in a common branch of the cascade resulting in thrombin formation. The thrombin itself finally initiates the formation of fibrin fibres which represent the protein backbone of blood clots.

The other main constituent of the final blood clot are the thrombocytes which are interconnected by the fibrin fibres and undergo a number of physiological changes during the process of coagulation. Within limits a lack of thrombocytes can be substituted by an increased amount of fibrin or vice versa. This is reflected in the observation that the thrombocyte counts as well as the fibrinogen concentration varies even within a healthy population.

Various methods have been introduced to assess the potential of blood to form an adequate clot and to determine the blood clots stability. Common laboratory tests such as thrombocyte counts or the determination of fibrin concentration provide information on whether the tested component is available in sufficient amount but lack in answering the question whether the tested component works properly under physiological conditions (e.g. the polymerisation activity of fibrinogen under physiological conditions can not be assessed by common optical methods). Besides that, most laboratory tests work on blood-plasma and therefore require an additional step for preparation and additional time which is unfavourable especially under POC (point of care) conditions.

Another group of tests which overcomes these problems is summarized by the term "viscoelastic methods". The common feature of these methods is that the blood clot firmness (or other parameters dependent thereon) is continuously determined, from the formation of the first fibrin fibres until the dissolution of the blood clot by fibrinolysis. Blood clot firmness is a functional parameter, which is important for haemostasis in vivo, as a clot must resist blood pressure and shear stress at the site of vascular injury. Clot firmness results from multiple interlinked processes: coagulation activation, thrombin formation, fibrin formation and polymerization, platelet activation and fibrin-platelet interaction and can be compromised by fibrinolysis. Thus, by the use of viscoelastic monitoring all these mechanisms of the coagulation system can be assessed.

A common feature of all these methods used for coagulation diagnosis is that the blood clot is placed in the space between a cylindrical pin and an axially symmetric cup and the ability of the blood clot to couple those two bodies is determined.

The first viscoelastometric method was called "thrombelastography" (Hartert H: Blutgerinnungsstudien mit der Thrombelastographie, einem neuen Untersuchungsverfahren. Klin Wochenschrift 26:577-583, 1948). As illustrated in FIG. 1, in the thromboelastography, the sample as a sample liquid 1 is placed in a cup 2 that is periodically rotated to the left and to the right by about 5°, respectively. A probe pin 3 is freely suspended by a torsion wire 4. When a clot is formed it starts to transfer the movement of the cup 2 to the probe pin 3 against the reverse momentum of the torsion wire 4. The movement of the probe pin 3 as a measure for the clot firmness is continuously recorded and plotted against time. For historical reasons the firmness is measured in millimeters.

The result of a typical measurement of this kind is illustrated in FIG. 2. One of the most important parameters is the time between the activator induced start of the coagulation cascade and the time until the first long fibrin fibres have been build up which is indicated by the firmness signal exceeding a defined value. This parameter will be called clotting time or just CT in the following. Another important parameter is the clot formation time (CFT) which gives a measure for the velocity of the development of a clot. The CFT is defined as the time it takes for the clot firmness to increase from 2 to 20 mm. The maximum firmness a clot reaches during a measurement, further on referred to as maximum clot firmness or just MCF, is also of great diagnostic importance.

Modifications of the original thromboelastography technique (Hartert et al. (U.S. Pat. No. 3,714,815) have been described by Cavallari et al. (U.S. Pat. No. 4,193,293), by Do et al. (U.S. Pat. No. 4,148,216), by Cohen (U.S. Pat. No. 6,537,819). A further modification by Calatzis et al. (U.S. Pat. No. 5,777,215) illustrated in FIG. 3 is known under the term thromboelastometry.

Contrary to the modifications mentioned above, thromboelastometry is based on a cup 2 fixed in a cup holder 12 while the probe pin 3 is actively rotated. For this purpose the probe pin 3 is attached to a shaft 6 which is suspended by a ball bearing 7 in a base plate 11 and has a spring 9 connected to it. An oscillating motion perpendicular to the drawing plane induced at the opposite end of the spring is transformed into a periodically rotation of the shaft 6 and the connected cup 2 around a rotation axis 5 by about 5° in each direction. As the sample liquid 1 begins to coagulate the motion amplitude of the shaft 6 which is detected by the deflection of a light beam from detecting means 10 and a mirror 9 starts to decrease.

During coagulation the fibrin backbone creates a mechanical elastic linkage between the surfaces of the blood-containing cup 2 and a probe pin 3 plunged therein. A proceeding coagulation process induced by adding one or more activating factor(s) can thus be observed. In this way, various deficiencies of a patient's haemostatic status can be revealed and can be interpreted for proper medical intervention.

A general advantage of viscoelastometric, e.g. thromboelastometric, techniques compared to other laboratory methods in this field therefore is that the coagulation process and the change of mechanical properties of the sample are monitored as a whole. This means that—in contrary to other laboratory methods mentioned above—thromboelastometry does not only indicate if all components of the coagulation pathways are available sufficient amounts but also if each component works properly.

To obtain detailed information on the correct amount and function of the thrombocytes as well as the fibrinogen and certain factors nowadays there is an increasing amount of compounds available which activate or inhibit certain components of the coagulation system. This allows determining at which point of the coagulation system a problem is located.

For practical reasons theses compounds are usually injected into the disposable plastic cup which later on is used for the measurement by using a pipette (either a manual or an automatic one). In the last preparation step, after the blood or plasma sample has been added, the whole amount of sample (blood/plasma and the additional chemicals) is mixed by drawing it into the pipette tip and dispensing it into the cup again.

The possibility to activate or to inhibit certain components of the coagulation system is especially useful in conjunction with state-of-the-art thromboelastometers such as the ROTEM (Pentapharm GmbH, Munich, Germany) which allows conducting four measurements in parallel. This allows detailed information on the current status of the coagulation-situation of a patient to be achieved and therefore allows an appropriate therapy within several minutes.

This is of particular importance in case of patients struck by massive blood loss as it often occurs in context with multiple traumata or major surgery. The blood of such patients often is diluted due to infusions which are administered to replace the loss in volume. This leads to a decrease of the concentration of thrombocytes as well as coagulation factors including fibrinogen.

Main advantages of thromboelastometry and thromboelastography are the possibility to perform several differential tests in parallel in order to precisely determine which kinds of blood products are the appropriate medication, the possibility to perform the measurement at or close to the point of care (POC) and—compared to other methods—the relatively small amount of time until valid results are available.

On the other hand the operator has to perform a significant number of steps in order to start the measurement (preparation of the reagents, attachment of the probe pin and the cup to the instrument, pipetting and mixing the blood sample and the reagents, adjustment of computer settings, etc.) on which the time spent is considerable, especially in the case of surgery being performed.

Furthermore this rather complex preparation also increases the risk of operating errors. There have been several approaches to simplify the usage of thromboelastometers. The Rotem-System (Pentapharm GmbH, Munich, Germany) e.g. is supplied with an automatic pipette which simplifies the handling to a large degree and thereby decreases the risk of operating errors.

WO 2008093216 describes the approach to provide the adequate amount of each of the reagents needed for one specific test in a ready-to-use mixture. In order to prevent the reaction of the reagents prior to the measurement, they are supplied in a lyophilisate state. This is additionally advantageous as the reagents can be stored at room temperature. Using this approach the preparation is reduced to the steps of adding the blood sample into the reagent container, mixing of blood with the reagent and transferring the mixture to the instrument.

US 2007/0059840 A1 describes a hemostasis analysis device and method. The device includes a container for holding a sample to be tested and a bobber configured to be buoyantly suspended on the sample. A magnet is secured to the bobber. The container can be driven in an oscillating motion. An external magnetic field is generated adjacent to the bobber. A magnetic field strength detector detects changes in the magnetic field as a result of movement of the bobber and magnet responsive to the oscillating motion of the container and clotting of the sample.

Such a new measuring system entails acceptability problems and uncertainties for a user. Moreover, that analysis device does not fit in existing measuring systems. Therefore new systems have to be completely designed.

All these modifications lead to a significant improvement of handling of modern thromboelastometers and thromboelastographs, however, no successful approach to develop a widely automated technique has been made since Hartert's invention 60 years ago. One of the two main reasons of that is the fact that the measurement requires two disposable parts (cup and pin) being moved in relation to each other and thus have to be reversibly attached to different parts of the measurement device. E.g. in FIG. 3, the probe pin 3 is attached to the shaft 6 and the cup 2 to the cup holder 12, respectively. The other main reason is that different tests are required to get comprehensive information of a current bleeding status of a patient. These different tests require different reagents which have to be mixed with the blood sample.

SUMMARY OF THE INVENTION

It is a problem underlying the presented invention to provide a cartridge device for a measuring system for measuring viscoelastic characteristics of a sample liquid, in particular a blood sample.

Directly connected to this invention is the problem to provide a corresponding measuring system for measuring viscoelastic characteristics of a sample liquid, in particular the coagulation characteristics of a blood sample liquid.

It is a further problem underlying the invention to provide a method for measuring viscoelastic characteristics of a sample liquid using said measuring system.

These problems are solved by the subject-matter of the independent claims. Preferred embodiments are set forth in the dependent claims.

In a first aspect, the present invention provides a cartridge device for a measuring system for measuring viscoelastic characteristics of a sample liquid, in particular a blood sample, comprising
a cartridge body having at least one measurement cavity formed therein and having at least one probe element arranged in said at least one measurement cavity for performing a test on said sample liquid; and
a cover being attachable on said cartridge body;
wherein said cover covers at least partially said at least one measurement cavity and forms a retaining element for retaining said probe element in a predetermined position within said at least one measurement cavity.

In a second aspect, the present invention provides a measuring system for measuring viscoelastic characteristics of a sample liquid, in particular a blood sample, comprising: at least one interface element; at least one shaft rotatably supported by the interface element to be rotated by drive means; at least one cartridge device fixed to the interface element for holding the sample liquid, the at least one cartridge device comprising a cartridge body with a cover and at least one probe element arranged in a measurement cavity formed in said cartridge body for cooperating with the at least one shaft; at least one detecting means cooperating with the shaft for measuring viscoelastic characteristics of the sample liquid; and control means to control the measuring system.

In a third aspect, the present invention provides a method for measuring viscoelastic characteristics of a sample liquid by means of said measuring system, comprising the following steps:

a) providing the cartridge device having at least one measurement cavity with at least one probe element arranged therein;
b) attaching the cartridge device to said interface element, said shaft being inserted into said probe element;
c) filling said measurement cavity of said cartridge device with sample liquid;
d) rotating said shaft in an oscillating motion around said rotation axis; and
e) measuring viscoelastic characteristics of said sample liquid by detecting the rotation of said shaft by said detecting means.

In a preferred embodiment the probe element comprises a probe pin to cooperate with the sample liquid and a connector section for a connection to the measuring system. The connector section is formed e.g. as a bore extending within the probe element and comprises frictional connection means which can be e.g. clip means or a thread. An insertion guide facilitates an insertion of a part, in particular a shaft, of a measuring system. Thereby the shaft can be connected securely to the probe element.

The at least one measurement cavity can comprise bearing or supporting means for the probe element to align or hold the probe element prior to insertion of the shaft.

After the shaft has been inserted into the connector section, the shaft can be lifted to position the probe element at a working position.

In an alternative preferred embodiment the probe element is formed as a detachably fixed component part of the cover. An operator only has to attach the cartridge device to the measuring system the shaft being inserted into the probe element will detach the probe element from the cover and hold it securely in a position ready to carry out a measurement. Therefore the probe element comprises a fixing section for detachably fixing the probe element at fixing means of the cover.

After a measurement the cartridge device can be detached from the measuring system wherein the shaft is removed from the probe element. Then the probe element will seal the measurement cavity against the cover by means of e.g. a flange adapted to form a sealing. The cover retains the probe element within the measurement cavity.

It is preferred that the fixing means of the cover comprises clip means cooperating with corresponding clip means of the fixing section of the probe element.

In an alternative embodiment the fixing section of the probe element is integrally formed with the cover, the fixing means of the cover comprising a perforation.

The cover can be fixed on the cartridge body either by bonding or welding. In an alternative embodiment the cover is integrally formed with the cartridge body, e.g. made of a plastic material. It is also possible that the cover is made of a material which is different from the cartridge body. That can be done for example by two- or more-component-moulding.

In a further preferred embodiment the cartridge device further comprises at least one receiving cavity formed therein for receiving the sample liquid; at least one reagent cavity for holding at least one reagent; a ductwork connecting said cavities and the at least one measurement cavity; and at least one pump means connected to the ductwork for transporting the sample liquid from the at least one receiving cavity to the at least one measurement cavity by means of the ductwork, wherein the cover covers and at least partially forms said cavities and said ductwork and forms at least partially the pump means.

In a further embodiment the at least one reagent cavity is integrally formed with the pump means or/and with the at least one measurement cavity or/and with one or more of the ductworks. The reagent cavity can be formed as a deep cavity or just a small place where reagent can be deposited. Thus the sample liquid being pumped through the ductwork and the pump means into the measurement cavity can be mixed with the reagent.

The pump means comprise at least one valve for a directed flow of the sample liquid in order to direct the pumped liquid into the measurement cavity.

In another embodiment the reagent or an additional reagent can be stored in at least one reagent receptacle which can be opened by external means.

In a further embodiment the at least one reagent receptacle storing a reagent is integrated in the cover.

In another embodiment the at least one reagent receptacle comprises a bottom part which can be opened by external means to discharge the reagent into the ductwork and/or into one of the cavities. The receptacle can be adapted as a blister receptacle, for example.

The at least one reagent can be stored within the cartridge device in pulverized, solid or liquid form.

The cartridge device can be further provided with at least one reagent stored therein.

Filling in sample liquid can be done directly into the measurement cavity if no receiving cavity is provided. To this end the sample liquid can be injected through the cover via an opening or passage hole in the interface element or through a ductwork by an operator or by a control apparatus.

In case of a receiving cavity the sample liquid can be filled into the receiving cavity and be pumped by the pump means to the measurement cavity.

To fill in sample liquid, operate the pump means, add reagents and/or open the reagent receptacle the measuring system is equipped with a control apparatus. The control apparatus has means to access the pump means through a pump access formed as a passage of the interface element. Further the control apparatus can inject sample liquid through an inlet opening in the interface element into the receiving cavity. The control apparatus comprises also operating means to inject or to add reagents into the cartridge device as well as to open reagent receptacles.

Further features and advantages of the present invention will be evident from a description of embodiments with reference to the figures.

BRIEF DESCRIPTION OF THE DRAWINGS

The figures are showing the following:

FIG. 7a is a schematic drawing of a first embodiment of a probe element.

FIG. 7b is a schematic drawing of the first embodiment of the probe element of FIG. 7a within a measuring cavity of the first or a second embodiment of the cartridge device according to the invention before use.

FIG. 7c is a schematic drawing of the first embodiment of the probe element of FIG. 7a within a measuring cavity of the first or the second embodiment of the cartridge device according to the invention in use.

FIGS. 8a-c are technical drawings of the preferred probe element of FIG. 7a.

FIG. 9b is a sectional view B-B of the cartridge device of FIG. 9a.

FIG. 9c is a sectional view C-C of the cartridge device of FIG. 9a.

FIG. 9d is a sectional view D-D of the cartridge device of FIG. 9a.

FIG. 10a is a top view of the cartridge device of FIG. 9a.

FIG. 10b is a sectional view E-E of the cartridge device of FIG. 10a.

FIG. 11a is a sectional view of a pump means of the cartridge device of FIG. 9a.

FIG. 12 is a schematic top view of the pump means of FIG. 11a.

FIG. 13b is a top view of the measuring system of FIG. 13a.

FIG. 13c is a sectional view H-H of the measuring system of FIG. 13b.

DESCRIPTION OF EXEMPLARY EMBODIMENTS

Figure 1:
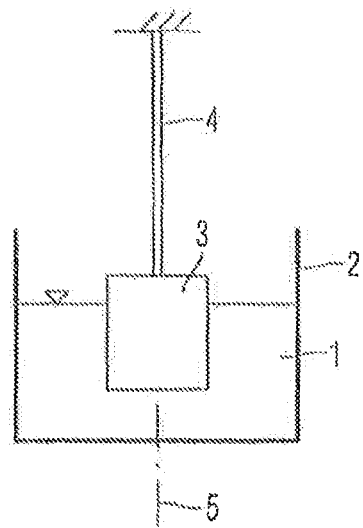
FIG. 1 is a schematic drawing of the principle of thromboelastography according to Hartert.
Figure 2:
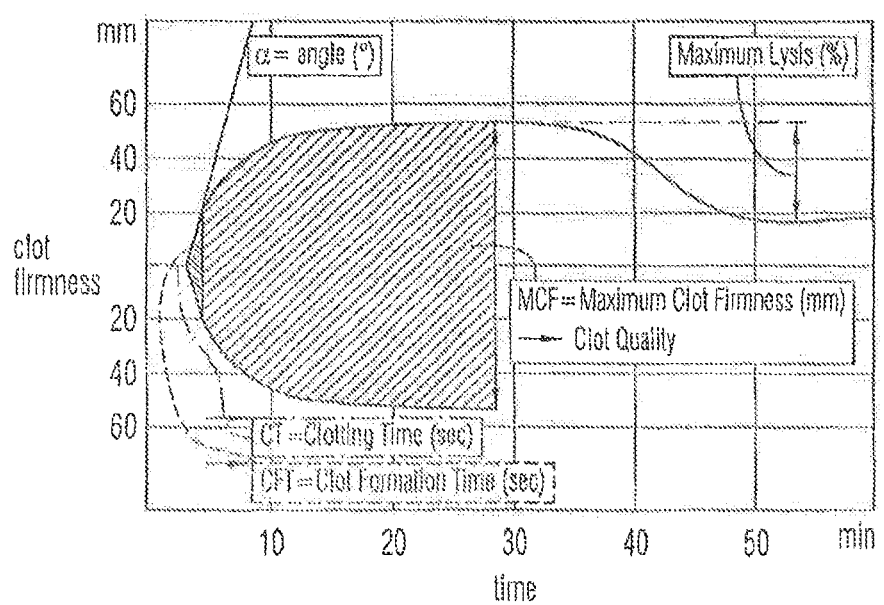
FIG. 2 is an exemplary diagram showing a typical thromboelastometric measurement.

Parts and components having same functions are depicted with same references.

Prior to a detailed description of the preferred embodiments the basic features and a basic practical implementation are summoned as follows. All embodiments refer to a cartridge device 50 (see FIG. 13c) which can be formed in a first embodiment (see FIGS. 4, 5 and 6), in a second embodiment (see FIGS. 7b, 7c and 15) or in a third embodiment (see FIGS. 9 to 10). The cartridge device 50 contains all parts coming into contact with a sample liquid 1 to be tested. These can be also reagents the sample liquid has to be mixed with for a measurement. The cartridge device 50 is part of a measuring system 40 (see FIG. 13c) to which the cartridge device 50 is attached before measurement. The measuring system 40 also comprises a control apparatus (not shown) which has been adapted to interact with the cartridge device 50 by electrical and/or mechanical means to control flow of sample liquid 1 (see FIG. 7c) and measurements as well as collect data. Furthermore this apparatus contains mechanical and electronic parts required for measurement, data analysis and user interaction. The present invention is not only suitable for thromboelastometry, thromboelastography and platelet aggregometry but also for other blood tests usually performed regarding surgery.

A first embodiment of a cartridge device 50 of the invention will be described with reference to FIGS. 4 and 5. The cartridge device 50 for the measuring system 40 for measuring medical relevant, e.g. viscoelastic, characteristics like coagulation or platelet function of a sample liquid 1, particularly a blood sample, comprises a receiving cavity 16 for receiving the sample liquid 1, pump means 18 for pumping the sample liquid, a reagent cavity 19 for storing a reagent 21, a measurement cavity 20 for measuring the sample liquid 1 and a ductwork connecting said cavities. The ductwork comprises an inlet duct 13 from the receiving cavity 16 to the pump means 18, an intermediate duct from the pump means 18 to the reagent cavity 19 and an outlet duct 15 from the reagent cavity 19 to the measurement cavity 20. In a variation said cavities and ducts can be arranged in different ways one of which is shown in FIG. 5, wherein pump means 18 and reagent cavity 19 are changed.

Figure 10A:
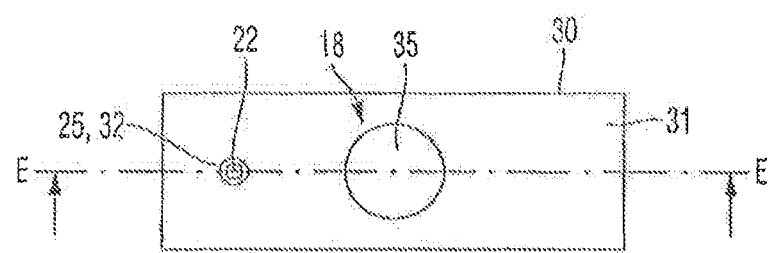
Figure 10B:
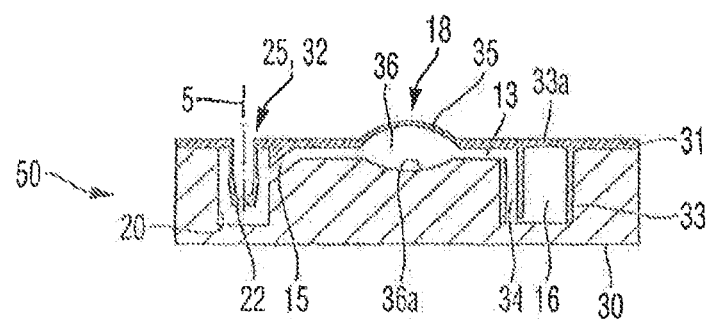

In this embodiment the receiving cavity 16 consists of a cavity within the cartridge device 50. The sample liquid 1 can be applied by means of a syringe, pipette etc, e.g.

through a self sealing cap shown as a receiving cavity cover 330a in FIG. 10b. By operating the pump means 18, e.g. by means of the control apparatus mentioned above, the sample liquid is transported to the reagent cavity 19, where the reagent 21 required for measurement is mixed with the sample liquid 1. Further pumping the sample liquid 1 will transfer it into the measurement cavity 20 in which the measurement (described below) is carried out.

In an alternative embodiment the reagent cavity 19 is integral formed with the pump means 18 and/or with the measurement cavity 20 and/or with the ductwork. The transport of the sample liquid 1 can be controlled by said control apparatus.

Figure 6:
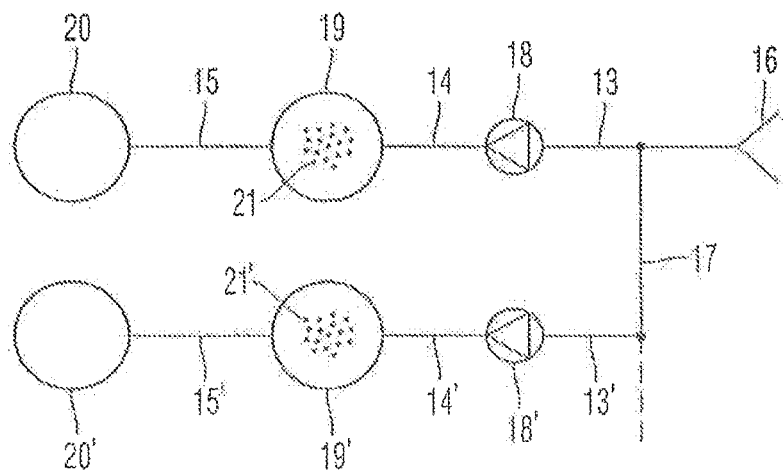
FIG. 6 is a schematic drawing of another variation of the first embodiment of the cartridge device according to the invention.

FIG. 6 shows another variation of the first embodiment. Two arrangements of FIG. 4 with only one receiving cavity 16 are arranged in parallel, wherein a first inlet duct 13 communicates with a second inlet duct 13' connected to second pump means 18'. A second intermediate duct 14' leads to a second reagent cavity 19' storing a second reagent 21'. A second outlet duct 15' connects the second reagent cavity 19' to the second measurement cavity 20'. FIG. 6 shows only one possible variation of a plurality of different arrangements easily imagined. The sample liquid 1 is shared among the arrangements in parallel. Controlled by the external control apparatus the shared portions of the sample liquid 1 are mixed with different reagents 21, 21' during transport.

It is apparent to a person skilled in the art that in order to achieve a maximum benefit for a user different types of tests can be combined in one cartridge device 50.

Figure 4:
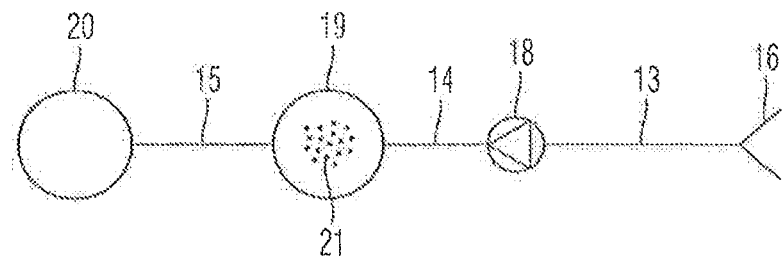
FIG. 4 is a schematic drawing of a first embodiment of a cartridge device according to the invention.
Figure 5:
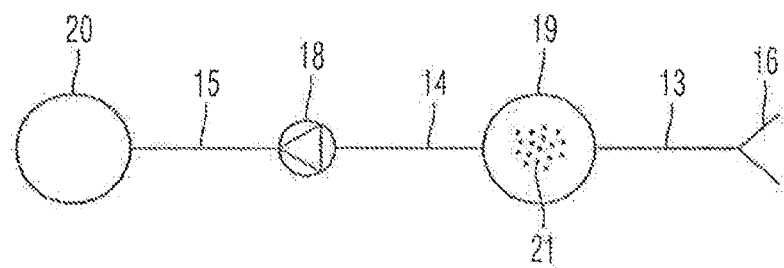
FIG. 5 is a schematic drawing of a variation of the first embodiment of the cartridge device according to the invention.

In a preferred embodiment the cartridge device 50 comprises four arrangements of FIG. 4 or 5 having 4 measurement cavities 20, 20'. Thus measurements can be done with different reagents on the same liquid sample or with same reagents as well to check plausibility.

Regarding e.g. blood coagulation there are different reagents available which activate or suppress different parts of the coagulation cascade. Pentapharm GmbH (Munich, Germany) for example amongst others provide tests for intrinsic and extrinsic activation of a blood sample (INTEM or EXTEM respectively), and also a test for extrinsic activation in which the thrombocyte function is suppressed by administration of cytochalasin D (FIBTEM). It is state of the art that it is possible by wise combination of such tests to be able to determine very precisely at which point within the coagulation cascade a problem occurs. This is of great importance in order to determine a proper medication. By comparison of the results on an EXTEM test of a pathologic sample to those of a FIBTEM test of the same sample it is possible to e.g. precisely determine if a coagulation disorder results from lack of fibrinogen or a malfunction of platelets. Generally, there are different typical medical scenarios in which coagulation disorders are very likely to occur. For example coagulation disorders occurring during liver transplantation are merely caused by lack of certain coagulation factors etc., while coagulation disorders during open heart surgery are most likely due to the influence of heparin. This means basically that different medical settings require different coagulation tests. Referring to FIG. 6 it is possible and worthwhile to provide different cartridge devices 50 for different typical operations. It is also possible to combine e.g. an INTEM, an EXTEM and a FIBTEM coagulation test with a platelet aggregometry test within one cartridge. Using such a cartridge the preparation of a measurement which provides almost overall information about the coagulation status of a patient merely requires the two steps of attaching the cartridge device 50 to the measuring system 40 with the external control apparatus and injecting the blood sample as one sample liquid 1. Considering the significance of more complex and time consuming preparation of several thromboelastography or thromboelastometry tests, it is evident that the invention is of great advantage for easier, safer and more accurate POC-tests.

It is important to note that the cartridge devices 50 of the described embodiments are suitable for different diagnostic tests like thromboelastometry, thromboelastography, platelet aggregometry and others. Depending on which type of test or tests the cartridge device 50 is designed for, there are different additional parts required which interact with the sample during measurement and/or an external control apparatus. Possible adaptations for thromboelastometry and platelet aggregometry are described below.

FIG. 7a is a schematic drawing of a first embodiment of a probe element 22 arranged in the measurement cavity 20 (see also FIGS. 10b and 13c). FIGS. 7b and 7c show a second embodiment of the cartridge device 50 in form of a cartridge body 30 which comprises only the measurement cavity 20. In the shown example this cavity 20 is accessible via a ductwork 15, 15' through a cavity wall. Alternatively the cavity 20 can be filled through a cover 31, e.g. by injection needles or the like.

Figure 3:
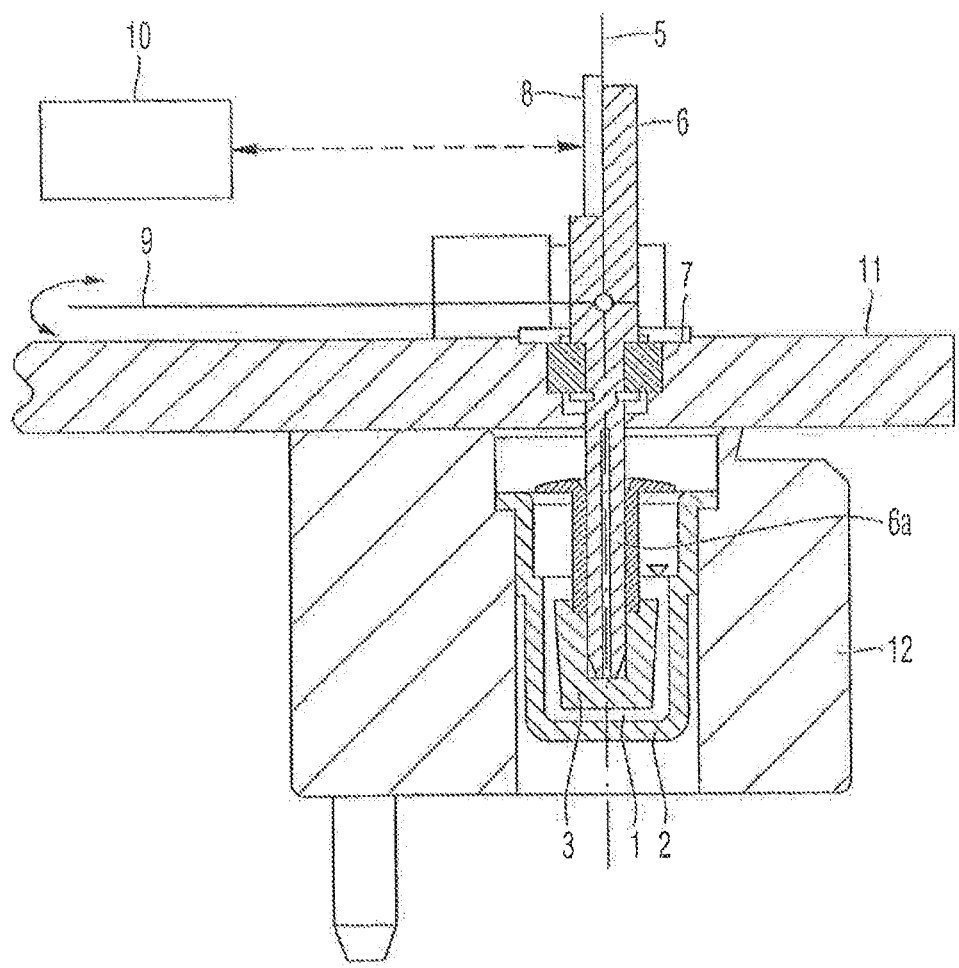
FIG. 3 is a schematic drawing of the thromboelastometry.

The probe element 22 comprises the probe pin 3 (see FIG. 1) which is connected to a flange 24 and a fixing section 25 via an intermediate section 23. The probe element 22 is formed as a rotational part and further comprises a connector section 26 formed as a bore extending within the probe element 22 along its longitudinal axis, which is the rotational axis 5 as well (see FIG. 3).

The probe element 22 is arranged in the measurement cavity 20 of the cartridge body 30 of the cartridge device 50 as shown in FIG. 7b. The measurement cavity 20 is covered by the cover 31 (see also FIGS. 10b and 13c). The cover 31 comprises an opening with fixing means 32 above the measurement cavity 20. The probe element 22 is arranged such that its fixing section 25 corresponding to the fixing means 32 engage with them. In this manner the probe element 22 is detachably fixed to the cover 31. The fixing means 32 in this example are equipped with a circular nose corresponding to a circular notch of the fixing section 25 of the probe element 22. Other fixing means e.g. clip means or the like are possible. The flange 24 is in contact to the inner side of the cover 31.

During attaching the cartridge device 50 to the measuring system 40 (see also FIG. 13c) the shaft 6 of the measuring system 40 (see FIG. 3 and FIGS. 13a . . . c) is inserted with its bottom portion, an insert section 6a, into the connector section 26. By insertion into the connector section 26 of the probe element 22 the probe element 22 will be detached from the cover 31 not before the insert section 6a is completely inserted in the connector section 26. Then the probe element 22 will be put into in a measuring position as shown in FIG. 7c and kept there. The insert section 6a of the shaft 6 is engaged with the connector section 26 of the probe element 22 e.g. by friction, clip means, thread or the like. In case of a thread the probe element 22 will be hold by the engagement with or perforation of the cover 31. The shaft 6 having a corresponding thread on its insert section 6a will be inserted into the connector section of the probe element 22 by rotation until the insert section 6a will be completely inserted into the connector section 26. Then the shaft 6 can be pushed down and/or rotated together with the fully engaged probe element 22 until the probe element 22 will be detached from the cover 31. FIG. 7c shows the sample liquid 1, which has been pumped into the measurement cavity 20.

The probe pin 3 of the probe element 22 is immersed in the sample liquid 1. A measurement as described above can be carried out. After the measurement the cartridge device 50 is detached from the measuring system 40, wherein the shaft 6 is drawn up together with the probe element 22 against the cover 31. The insert section 6a of the shaft 6 will be drawn out of the connector section 26 of the probe element 22 the flange 24 thereof contacting and sealing the opening of the cover 31. Instead of a flange 24 the upper end of the probe element 22 can have a larger diameter than the opening in the cover 31. It is preferred that the insert section 6a of the shaft 6 and the measurement cavity 20, 20' are formed symmetrically.

It is also possible to insert the insert section 6a of the shaft 6 into the connector section 26 of the probe element 22 and push the probe element 22 down until its bottom contacts the bottom of the measurement cavity 20, 20' ensuring that the insert section 6a is completely inserted into the connector section 26. Then the shaft 6 will be moved up into the measuring resp. working position of the probe element 22 as shown in FIG. 7c.

Figure 8A:
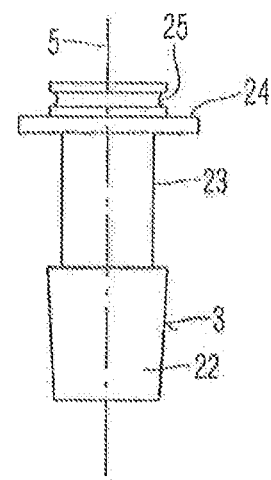
Figure 8B:
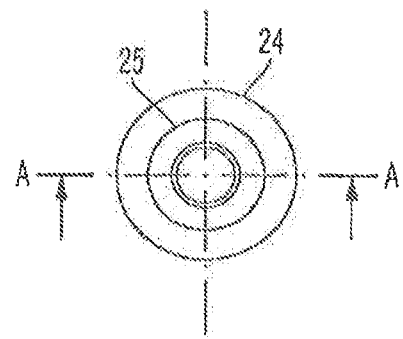
Figure 8C:
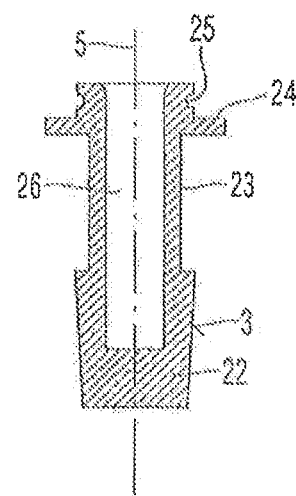

FIGS. 8a . . . c are technical drawings of a preferred embodiment of the probe element 22 of FIG. 7a. FIG. 8a shows a side view and FIG. 8b shows a top view of the probe element 22 parts of which have been described above regarding FIG. 7a. Finally, FIG. 8c illustrates a sectional view along rotational axis 5. The connector section 26 extends over more than about 75% of the length of the probe element 22.

Now a third embodiment of the cartridge device 50 will be described with reference to FIGS. 9a, . . . d and FIGS. 10a . . . b.

Figure 9A:
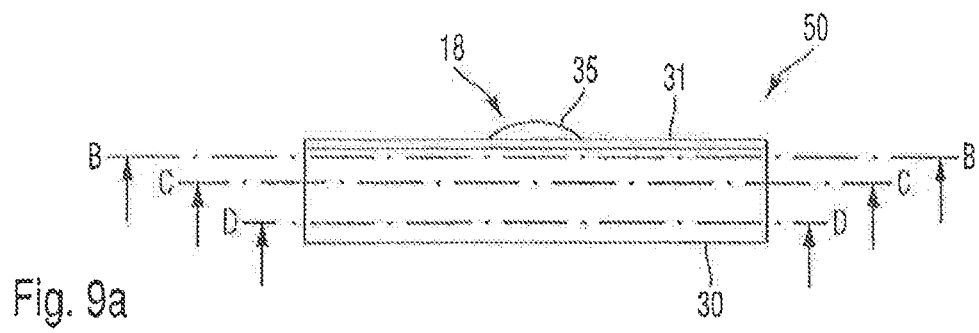
FIG. 9a is a side view of a third embodiment of a cartridge device according to the invention.
Figure 9B:
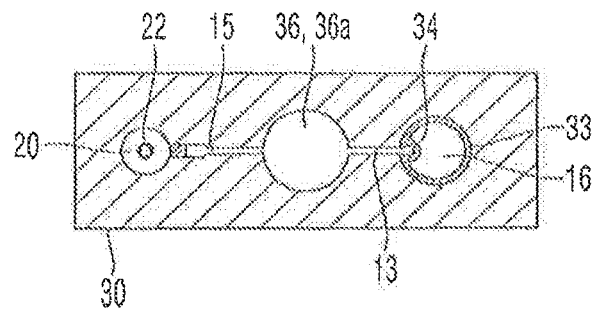
Figure 9C:
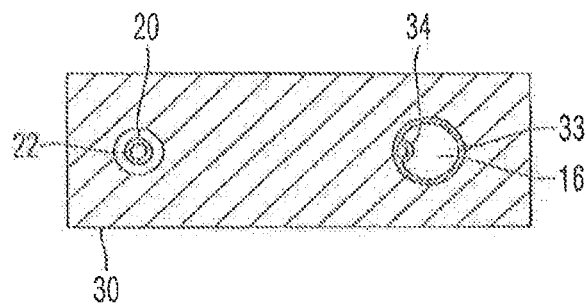
Figure 9D:
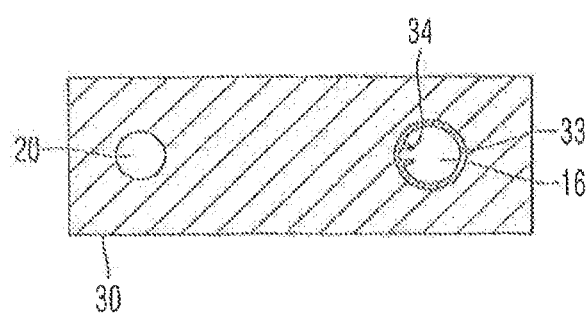

FIG. 9a is a side view of a second embodiment of a third embodiment of the cartridge device 50 according to the invention. FIG. 9b is a sectional view B-B of the cartridge device 50 of FIG. 9a. FIG. 9c is a sectional view C-C of the cartridge device of FIG. 9a. FIG. 9b is a sectional view D-D of the cartridge device of FIG. 9a. FIG. 10a is a top view of the cartridge device of FIG. 9a. FIG. 10b is a sectional view E-E of the cartridge device of FIG. 10a.

The cartridge device 50 of this example is equipped with the ductwork 13 and 15. The ducts are formed with an diameter of approximately 1 mm in this embodiment. The ductwork requires that the cartridge device 50 comprises two parts: the cartridge body 30 and the cover 31, which are glued or welded together to obtain a leak-proof device. The cartridge body 30 is relative rigid and the cover 31 is formed as an elastic part. So it is possible to integrate the pump means 18 into the cover 31. Moreover, the cover 31 covers the receiving cavity 16 with the receiving cavity cover 33a and forms a type of liner wall 33 and a separation wall 34 forming an inlet for the inlet duct 13 within the receiving cavity 16. The receiving cavity cover 33a might act as a self seal for injection of a sample liquid 1 by a syringe for example. The cover 31 forms top parts of the ductwork 13 an 15 and a cover of the measurement cavity 20 (see also FIGS. 7b . . . c). In this example the pump means 18 comprises a pump membrane 35 formed by the cover 31. The pump membrane 35 cooperates with a pump cavity 36 formed with a pump cavity bottom 36a in the cartridge body 30 below the pump membrane 35.

In this embodiment a reagent cavity 19, 19' is formed, e.g. by sections of the ductwork or/and the pump means 18, 18' in which the reagents can be stored resp. deposited, especially on the pump cavity bottom 36a, for example.

The pump means 18 will now be described with reference to FIGS. 11a . . . b and FIG. 12.

Figure 11A:
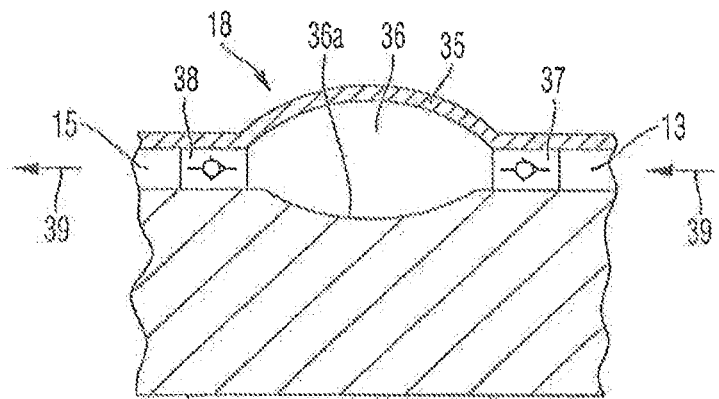
Figure 11B:
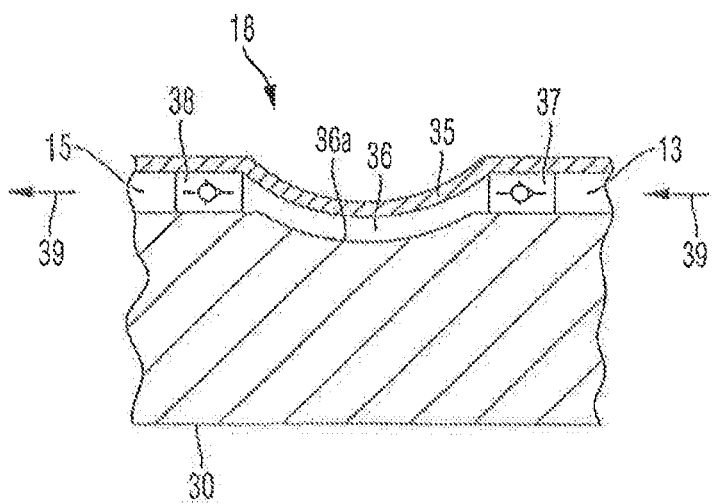
FIG. 11b is a sectional view of the pump means of FIG. 11a in operated position.
Figure 12:
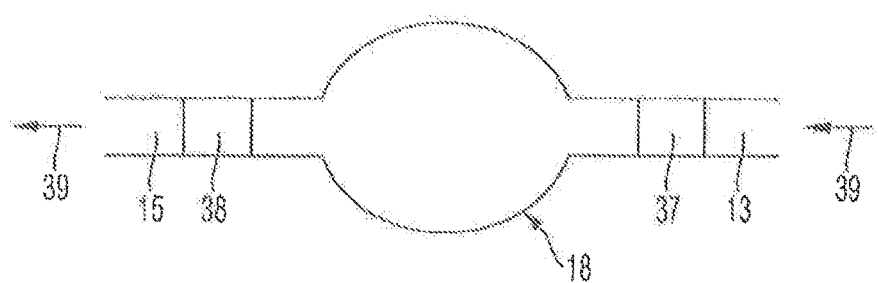

FIG. 11a is a sectional view of the pump means 18, 18' of the cartridge device 50, FIG. 11b is a sectional view of the pump means 18 of FIG. 11a In operated position, and FIG. 12 is a schematic top view of the pump means 18 of FIG. 11a.

In this example the pump cavity 36 is connected to the inlet duct 13 via an inlet valve 37 and to the outlet valve via an outlet valve 38. Actuation of the pump membrane 35 (shown in FIG. 11b in a working cycle) by an appropriate actuating means (not shown) of the control apparatus the pump means 18 will create a directed flow of the sample liquid 1 in a flow direction 39 depicted by the arrows. The pump membrane 35 being an integrated part of the cover 31 can be made of the cover material or a part made of another material integrally manufactured with the cover 31, e.g. two components manufacturing. The valves 37, 36 can be a type of non-return valve. FIG. 12 shows a top view of the pump means in a schematic way.

An external force exerted on the pump membrane 35 increase the pressure within the pump cavity 36 and opens outlet valve 38 and closes inlet valve 37. Releasing the external force the elastic pump membrane 35 returns into the position shown in FIG. 11a whereby outlet valve 38 will be closed and inlet valve 37 opened to let sample liquid 1 into the pump cavity 36. This mechanism is state of the art according to DE10135569. In context with the present invention the actuation means of the control apparatus activating the pump membrane 35 from outside has the advantage of strict separation between those parts coming into contact with the sample liquid 1 and the control apparatus. At the same time the total number of parts required for the cartridge device 50 being a disposable part as well is kept on a minimum.

Figure 13A:
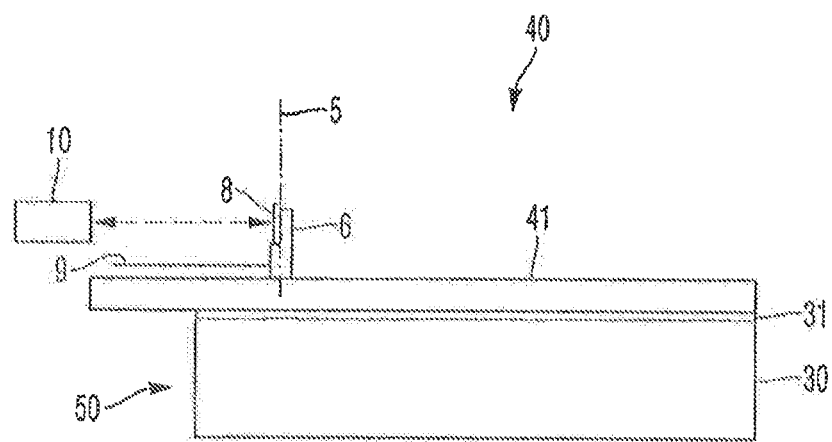
FIG. 13a is a side view of an embodiment of a measuring system according to the invention.

Now the measuring system 40 according to the invention is described in an embodiment with reference to FIGS. 13a . . . c.

Figure 13B:
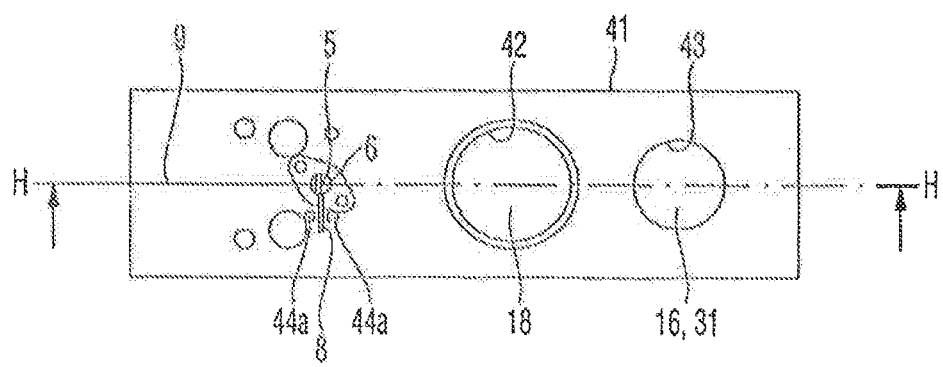

FIG. 13a, is a side view of an embodiment of the measuring system 40, FIG. 13b is a top view of the measuring system 40 of FIG. 13a, and FIG. 13c is a sectional view H-H of the measuring system 40 of FIG. 13b.

The measuring system 40 comprises an interface element 41 to which the cartridge device 50 is attached and fixed. The interface element 41 is shown in FIGS. 13a to 13c in way of example as a base plate. The function of the interface element 41 is to support the shaft 6 and to maintain its position and thus the position of the probe element 22 fixed to the insert section 6a in a measurement position. The interface element 41 can be connected to the whole cover 31 as shown in FIGS. 13a to 13c or only to parts of the cover 31, e.g. surrounding the rotation axis 5. The shaft 6 is rotatable supported in a bearing 7 within a shaft passage 44 (FIG. 13c) and can be rotated around the rotation axis 5 (see also FIG. 3) by driving the spring 9 via driving means (not shown). The detecting means 10 cooperate with the mirror 8 fixed on the shaft 3, also shown in FIG. 3. The control apparatus mentioned above is not shown as well, but easy to imagine. Its actuation and/or operating means can access the pump means 18 through an opening pump access 42 in the interface element 41. The receiving cavity 16 is accessible through another inlet opening 43. These and other different passages or passage ways of the interface element 41 to have access to the cartridge device 50 and/or its cover 31 are illustrated by FIG. 13b as a top view of the measuring system 40 of FIG. 13a. Passage holes 44a are arranged next to the rotational axis 5 to form an access to the cover 31 above the measurement cavity 20, 20', e.g. for injection of liquid sample or reagents. Additional access passage holes can be arranged in the interface element 41, e.g. above the ductwork to access said ductwork.

FIG. 13*c* illustrates a sectional view H-H of FIG. 13*b* showing the mounted cartridge device 50 and the measuring system 40. The shaft 6 with its insert section 6*a* is inserted into the probe element 22 and keeps it in a measurement position as mentioned above. This embodiment comprises only one measurement cavity 20, but it is apparent to a person skilled in the art that modifications and combinations of the invention can be carried out in different ways.

Figure 14:
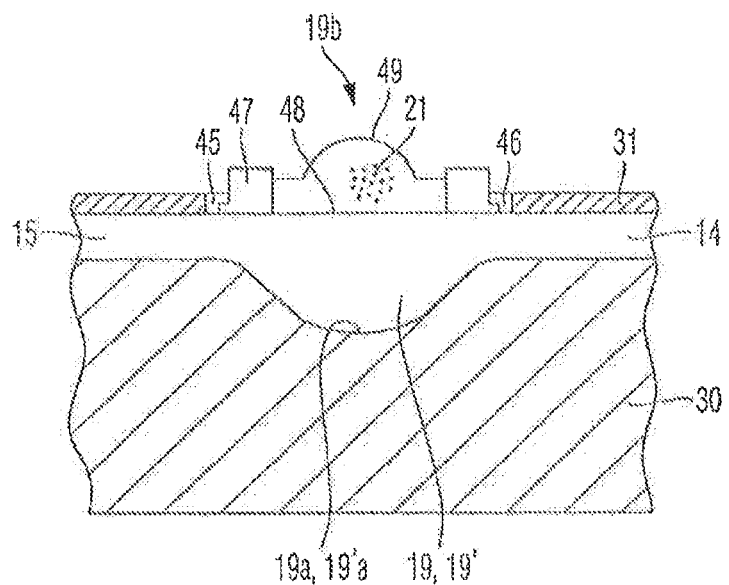
FIG. 14 is a sectional view of a reagent receptacle of a third embodiment of the cartridge device according to the invention.

Thus it is possible to e.g. arrange a reagent receptacle 19*b* in a blister receptacle e.g. as shown in FIG. 14 which is a sectional view of the reagent receptacle 19*b* of a third embodiment of the cartridge device 50 according to the invention. The receptacle 19*b* contains reagent 21 hold within a chamber defined by a blister cover 49, a bottom part 48 and a frame 47 hold in a retaining ring 46 within an reagent cover opening 45 in the cover 31 above the reagent cavity 19, 19' with a reagent cavity bottom 19*a*, 19*a*'. Upon exertion of a force by the control apparatus onto the blister cover 49 the bottom part 48 will open and discharge the reagent 21 into the reagent cavity 19, 19'. The receptacle 19*b* can be fixed to the cover by e.g. clip means as depicted. The frame 47 can be a reinforced ring. The blister cover 49 is reinforced so that it will not break when a force is exerted on it. Thus the leak-tightness of the cartridge device 50 will be ensured. In this way a unitized construction system can be made, wherein the respective reagents can be easily integrated into the cartridge device 50. It is also advantageous that the reagents can be designed as a small component being cooled resp. transported and supplied easily.

It is also possible to insert reagent receptacles into provided cavities being connected to the ductwork. The reagents can be designed as globules with an appropriate diameter so that they cannot flow through openings into the ductwork before being dissolved by the sample liquid.

Figure 15:
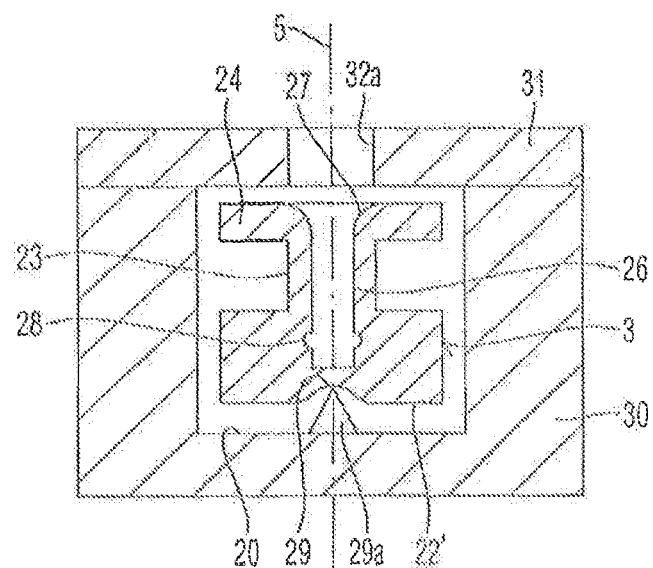
FIG. 15 is a schematic drawing of a second embodiment of the probe element.

FIG. 15 is a schematic drawing of a second embodiment of a probe element 22'. The probe element 22' is arranged in the measurement cavity 20. The probe pin 3 is provided with a dimple 29 at its bottom side. The dimple 29 forms with a nose 29*a* a toe bearing to support the probe element 22'. The probe element 22' is similar to the probe element 22 of FIG. 7*a*, but has no fixing section 25, only the flange 24. The connector section 26 comprises a top end formed with an insertion guide 27 for the insertion section 6*a* of the shaft. The probe element 22' is hold in the measurement cavity 20 in a specific manner so that the insertion section 6*a* of the shaft 6 can be inserted easily through an opening 32*a* of the cover 31 which has no fixing means. The insertion section 6*a* can engage with a groove 28 inside the connector section 26 of the probe element 22'. After that engagement which is supported by the toe bearing the shaft 6 will be drawn up together with the probe element 22' in the measuring position. It is a matter of fact that other engagement means can be used.

LIST OF REFERENCE NUMERALS

1 Sample liquid
2 Cup
3 Probe pin
4 Torsion wire
5 Rotation axis
6 Shaft
6*a* Insert section
7 Bearing
8 Mirror
9 Spring
10 Detecting means
11 Base plate
12 Cup holder
13, 13' Inlet duct
14, 14 Intermediate duct
15, 15' Outlet duct
16, 16' Receiving cavity
17 Branch duct
18, 18' Pump means
19, 19' Reagent cavity
19*a*, 19'*a* Regent cavity bottom
19*b* Reagent receptacle
20, 20' Measurement cavity
21, 21' Reagent
22, 22' Probe element
23 Intermediate section
24 Flange
25 Fixing section
26 Connector section
27 Insertion guide
28 Groove
29 Dimple
29*a* Nose
30 Cartridge body
31 Cover
32 Fixing means
32*a* Opening
33 Wall
33*a* Receiving cavity cover
34 Separation wall
35 Pump membrane
36 Pump cavity
36*a* Pump cavity bottom
37 Inlet valve
38 Outlet valve
39 Flow direction
40 Measuring system
41 Interface element
42 Pump access
43 inlet opening
44 Shaft passage
44*a* Passage hole
45 Reagent cover opening
46 Retaining ring
47 Frame
48 Bottom foil
49 Blister cover
50 Cartridge device

The invention claimed is:

1. A system comprising:
a cartridge comprising:
a first liquid transport path configured to receive a first portion of a blood sample via a first cavity, the first liquid transport path comprising a first reagent cavity containing a first reagent; a first testing cavity that is usable to measure a viscoelastic characteristic associated with a first liquid formed by mixing the first portion of the blood sample and the first reagent, and a first pathway from the first cavity to the first liquid transport path, the first pathway being configured to move the first portion of the blood sample from a bottom of the first cavity and into the first liquid transport path; and
a second liquid transport path configured to receive a second portion of a blood sample; the second liquid transport path comprising a second reagent cavity containing a second reagent, and a second testing cavity that is usable to measure a viscoelastic characteristic associated with a second liquid formed by mixing the second portion of the blood sample and the second reagent; and a control apparatus configured to control flow of liquid through the first liquid transport path and through the second liquid transport path, and to obtain data based on the first and second liquids, wherein at least one of the first reagent or the second reagent comprises globules having diameters that inhibit movement of the globules through the first liquid transport path or the second liquid transport path absent at least some dissolution of the globules.

2. The system of claim 1, wherein:

the first liquid transport path comprises a first duct for interconnecting at least the first reagent cavity and the first testing cavity, and a second duct for interconnecting at least the second reagent cavity and the second testing cavity; and each of the first and second reagent cavities comprises a reagent or combination of reagents comprising at least:
a first reagent to activate coagulation; and
a second reagent to activate coagulation.

3. The system of claim 2, wherein the first reagent and the second reagent activate different parts of a coagulation cascade.

4. The system of claim 3, wherein the cartridge comprises:
a third liquid transport path configured to receive a third portion of a blood sample, the third liquid transport path comprising a third reagent cavity containing a third reagent, and a third testing cavity that is usable to measure a viscoelastic characteristic associated with a third liquid formed by mixing the third portion of the blood sample and the third reagent; and
wherein the third reagent is different from the first reagent and the second reagent.

5. The system of claim 4, wherein:
the first reagent or the second reagent is for extrinsic activation of a portion of the test sample; and
the third reagent is for intrinsic activation of a portion of the test sample.

6. The system of claim 2, wherein the first liquid transport path comprises a first probe configured for measuring the viscoelastic characteristic associated with the first liquid; and
wherein the second liquid transport path comprises a second probe configured for measuring the viscoelastic characteristic associated with the second liquid.

7. The system of claim 6, further comprising:
a first detector to detect first information based on an output of the first probe, the first information being usable to determine the viscoelastic characteristic associated with the first liquid; and
a second detector to detect second information based on an output of the second probe, the second information being usable to determine the viscoelastic characteristic associated with the second liquid.

8. The system of claim 2, wherein the blood sample is received into the cartridge via a needle.

9. The system of claim 1, wherein the control apparatus is configured to interact at least one of electrically or mechanically with the cartridge to control the flow of liquid.

10. The system of claim 1, further comprising one or more pumps to implement pressure changes to control flow of liquids along the first liquid transport path and the second liquid transport path.

11. The system of claim 1, wherein the first reagent cavity comprises a first structure along the first liquid transport path where the first reagent is deposited; and
wherein the second reagent cavity comprises a second structure along the second liquid transport path where the second reagent is deposited.

12. The system of claim 1, wherein the first reagent cavity comprises a first cavity formed in the first liquid transport path where the first reagent is deposited; and
wherein the second reagent cavity comprises a second cavity formed in the second liquid transport path where the second reagent is deposited.

13. The system of claim 1, wherein the second liquid transport path comprises a second pathway to receive the second portion of the blood sample; and
wherein the first pathway is different from the second pathway.

14. A method of using the system of claim 1, the method comprising:
placing the cartridge in a measuring system comprising the control apparatus; and
after placing the cartridge in the measuring system, controlling pressure in the cartridge to draw the first portion of the blood sample into the first liquid transport path from the bottom of the first cavity.

15. The system of claim 1, wherein the globules have diameters that prevent movement of the globules into the first liquid transport path or the second liquid transport path absent at least some dissolution of the globules.

16. A system comprising:
a cartridge comprising:
a first liquid transport path configured to receive a first portion of a blood sample via a first cavity, the first liquid transport path comprising a first reagent cavity containing a first reagent, a first testing cavity that is usable to measure a viscoelastic characteristic associated with a first liquid formed by mixing the first portion of the blood sample and the first reagent, and a first pathway from the first cavity to the first liquid transport path, the first pathway being configured to move the first portion of the blood sample from a bottom of the first cavity and into the first liquid transport path; and
a second liquid transport path configured to receive a second portion of a blood sample; the second liquid transport path comprising a second reagent cavity containing a second reagent, and a second testing cavity that is usable to measure a viscoelastic characteristic associated with a second liquid formed by mixing the second portion of the blood sample and the second reagent; and
a control apparatus configured to control flow of liquid through the first liquid transport path and through the second liquid transport path, and to obtain data based on the first and second liquids;
wherein at least one of the first reagent or the second reagent comprises objects having dimensions that inhibit movement of the objects through the first liquid transport path or the second liquid transport path absent at least some dissolution of the objects.

17. The system of claim 16, wherein the control apparatus is configured to interact at least one of electrically or mechanically with the cartridge to control the flow of liquid.

18. The system of claim 16, further comprising one or more pumps to implement pressure changes to control flow of liquids along the first liquid transport path and the second liquid transport path.

19. The system of claim 16, wherein the first reagent cavity comprises a first structure along the first liquid transport path where the first reagent is deposited; and
wherein the second reagent cavity comprises a second structure along the second liquid transport path where the second reagent is deposited.

20. The system of claim 16, wherein the first reagent cavity comprises a first cavity formed in the first liquid transport path where the first reagent is deposited; and
wherein the second reagent cavity comprises a second cavity formed in the second liquid transport path where the second reagent is deposited.

21. The system of claim 16, wherein the second liquid transport path comprises a second pathway to receive the second portion of the blood sample; and
wherein the first pathway is different from the second pathway.

22. The system of claim 16, wherein:
the first liquid transport path comprises a first duct for interconnecting at least the first reagent cavity and the first testing cavity, and a second duct for interconnecting at least the second reagent cavity and the second testing cavity; and
each of the first and second reagent cavities comprises a reagent or combination of reagents comprising at least:
a first reagent to activate coagulation; and
a second reagent to activate coagulation.

23. The system of claim 22, wherein the first reagent and the second reagent activate different parts of a coagulation cascade.

24. The system of claim 23, wherein the cartridge comprises:
a third liquid transport path configured to receive a third portion of a blood sample, the third liquid transport path comprising a third reagent cavity containing a third reagent, a third testing cavity that is usable to measure a viscoelastic characteristic associated with a third liquid formed by mixing the third portion of the blood sample and the third reagent; and
wherein the third reagent is different from the first reagent and the second reagent.

25. The system of claim 24, wherein:
the first reagent or the second reagent is for extrinsic activation of a portion of the test sample; and
the third reagent is for intrinsic activation of a portion of the test sample.

26. The system of claim 16, wherein the first liquid transport path comprises a first probe configured for measuring the viscoelastic characteristic associated with the first liquid; and
wherein the second liquid transport path comprises a second probe configured for measuring the viscoelastic characteristic associated with the second liquid.

27. The system of claim 26, further comprising:
a first detector to detect first information based on an output of the first probe, the first information being usable to determine the viscoelastic characteristic associated with the first liquid; and
a second detector to detect second information based on an output of the second probe, the second information being usable to determine the viscoelastic characteristic associated with the second liquid.

28. The system of claim 16, wherein the blood sample is received into the cartridge via a needle.

29. The system of claim 16, wherein the objects have dimensions that prevent movement of the objects into the first liquid transport path or the second liquid transport path absent at least some dissolution of the objects.

* * * * *